(12) United States Patent
Peters et al.

(10) Patent No.: US 8,450,543 B2
(45) Date of Patent: May 28, 2013

(54) INTEGRATED METHODS OF PREPARING RENEWABLE CHEMICALS

(75) Inventors: Matthew W. Peters, Highlands Ranch, CO (US); Joshua D. Taylor, Evergreen, CO (US); David E. Henton, Midland, MI (US); Leo E. Manzer, Wilmington, DE (US); Patrick R. Gruber, Longmont, CO (US); Josefa M. Griffith, Parker, CO (US); Yassin Al Obaidi, Somerset, KY (US)

(73) Assignee: Gevo, Inc., Englewood, CO (US)

( * ) Notice: Subject to any disclaimer, the term of this patent is extended or adjusted under 35 U.S.C. 154(b) by 0 days.

(21) Appl. No.: 12/986,918

(22) Filed: Jan. 7, 2011

(65) Prior Publication Data
US 2011/0172475 A1 Jul. 14, 2011

Related U.S. Application Data

(60) Provisional application No. 61/293,459, filed on Jan. 8, 2010.

(51) Int. Cl.
*C07C 1/24* (2006.01)
(52) U.S. Cl.
CPC ........................................ *C07C 1/24* (2013.01)
USPC ........... 585/240; 585/242; 585/250; 585/252; 585/275; 585/257; 585/300; 585/241; 585/310; 585/314; 585/330; 585/379; 585/440
(58) Field of Classification Search
USPC .................... 585/14, 240, 254, 303, 310, 324, 585/640, 647, 241, 242, 250, 252, 257, 275, 585/300, 314, 330, 379, 440; 44/385, 398, 44/403, 437; 208/142–145
See application file for complete search history.

(56) References Cited

U.S. PATENT DOCUMENTS

| | | |
|---|---|---|
| 2,391,188 A | 12/1945 | Patterson |
| 2,391,646 A | 12/1945 | Schulze et al. |
| 2,529,061 A | 11/1950 | Vergnaud |

(Continued)

FOREIGN PATENT DOCUMENTS

| | | |
|---|---|---|
| GB | 1313083 | 4/1973 |
| JP | 10-237017 A | 9/1998 |

(Continued)

OTHER PUBLICATIONS

Young, "International Search Report," 2 pages, from PCT appl. No. PCT/US11/20549, United States Patent and Trademark Office, Alexandria, Virginia, United States (mailed Mar. 11, 2011).

(Continued)

*Primary Examiner* — In Suk Bullock
*Assistant Examiner* — Sharon Pregler
(74) *Attorney, Agent, or Firm* — Cooley LLP

(57) ABSTRACT

Isobutene, isoprene, and butadiene are obtained from mixtures of $C_4$ and/or $C_5$ olefins by dehydrogenation. The $C_4$ and/or $C_5$ olefins can be obtained by dehydration of $C_4$ and $C_5$ alcohols, for example, renewable $C_4$ and $C_5$ alcohols prepared from biomass by thermochemical or fermentation processes. Isoprene or butadiene can be polymerized to form polymers such as polyisoprene, polybutadiene, synthetic rubbers such as butyl rubber, etc. in addition, butadiene can be converted to monomers such as methyl methacrylate, adipic acid, adiponitrile, 1,4-butadiene, etc. which can then be polymerized to form nylons, polyesters, polymethylmethacrylate etc.

19 Claims, 5 Drawing Sheets

Integrated System to Convert Isobutanol to Renewable p-Xylene

U.S. PATENT DOCUMENTS

| | | |
|---|---|---|
| 2,554,054 A | 5/1951 | Owen |
| 2,813,119 A | 11/1957 | Taves |
| 2,894,978 A | 7/1959 | Katzschmann |
| 2,945,900 A | 7/1960 | Alexander et al. |
| 2,982,795 A | 5/1961 | Owen |
| 2,984,644 A | 5/1961 | Wheat |
| 3,002,035 A | 9/1961 | Hieronymus |
| 3,154,593 A | 10/1964 | Long |
| 3,301,906 A | 1/1967 | Besozzi et al. |
| 3,344,037 A | 9/1967 | Leavitt |
| 3,356,754 A | 12/1967 | Wofford |
| 3,445,521 A | 5/1969 | Callahan et al. |
| 3,509,237 A | 4/1970 | Aubrey |
| 3,513,193 A | 5/1970 | Katzschmann |
| 3,644,550 A | 2/1972 | Beuther et al. |
| 3,662,016 A | 5/1972 | Furuoya et al. |
| 3,686,341 A | 8/1972 | Eberly |
| 3,755,458 A | 8/1973 | Vrbaski et al. |
| 3,825,502 A | 7/1974 | Takenaka et al. |
| 3,827,968 A | 8/1974 | Givens et al. |
| 3,830,866 A | 8/1974 | D'Alessandro et al. |
| 3,832,418 A | 8/1974 | Bercik et al. |
| 3,836,603 A | 9/1974 | Connor, Jr. et al. |
| 3,850,981 A | 11/1974 | Trebellas et al. |
| 3,851,008 A | 11/1974 | Stowe et al. |
| 3,886,224 A | 5/1975 | Mitchell, Jr. |
| 3,887,612 A | 6/1975 | Shigeyasu et al. |
| 3,891,721 A | 6/1975 | Prudence |
| 3,959,400 A | 5/1976 | Lucki |
| 3,960,978 A | 6/1976 | Givens et al. |
| 3,997,621 A | 12/1976 | Brennan |
| 4,025,575 A | 5/1977 | Chang et al. |
| 4,096,340 A | 6/1978 | Fujii et al. |
| 4,100,220 A | 7/1978 | Bowman et al. |
| 4,112,011 A | 9/1978 | Kolombos |
| 4,129,600 A | 12/1978 | Childress et al. |
| 4,152,300 A * | 5/1979 | Riesser .................. 502/302 |
| 4,190,608 A | 2/1980 | Grasselli et al. |
| 4,197,185 A | 4/1980 | Le Page et al. |
| 4,225,743 A | 9/1980 | Hoshiyama et al. |
| 4,229,320 A | 10/1980 | Slaugh |
| 4,229,603 A | 10/1980 | Lyon |
| 4,241,220 A | 12/1980 | Itaya et al. |
| 4,244,806 A | 1/1981 | Le Page et al. |
| 4,266,958 A | 5/1981 | Cummings |
| 4,293,722 A | 10/1981 | Ward et al. |
| 4,304,948 A | 12/1981 | Vora et al. |
| 4,324,646 A | 4/1982 | Le Page et al. |
| 4,329,493 A | 5/1982 | Hashizume et al. |
| 4,331,823 A | 5/1982 | Wieder et al. |
| 4,342,876 A | 8/1982 | Klingman |
| 4,354,044 A | 10/1982 | Aoshima et al. |
| 4,385,157 A | 5/1983 | Auclair et al. |
| 4,393,259 A | 7/1983 | Ward et al. |
| 4,396,787 A | 8/1983 | Gluzek et al. |
| 4,398,920 A | 8/1983 | Guibet et al. |
| 4,423,267 A | 12/1983 | Dowling et al. |
| 4,448,643 A | 5/1984 | Lindner et al. |
| 4,456,779 A | 6/1984 | Owen et al. |
| 4,456,781 A | 6/1984 | Marsh et al. |
| 4,463,211 A | 7/1984 | Manning |
| 4,465,884 A | 8/1984 | Degnan et al. |
| 4,471,147 A | 9/1984 | Owen et al. |
| 4,499,316 A * | 2/1985 | Garska et al. .................. 585/415 |
| 4,504,692 A | 3/1985 | Arakawa et al. |
| 4,504,693 A | 3/1985 | Tabak et al. |
| 4,518,796 A | 5/1985 | Aoshima et al. |
| 4,531,014 A | 7/1985 | Gregory et al. |
| 4,542,251 A | 9/1985 | Miller |
| 4,544,792 A | 10/1985 | Smith et al. |
| 4,612,406 A | 9/1986 | Long et al. |
| 4,621,164 A | 11/1986 | Chang et al. |
| 4,642,369 A | 2/1987 | Modic et al. |
| 4,663,406 A | 5/1987 | Bronstert et al. |
| 4,698,452 A | 10/1987 | Le Van Mao et al. |
| 4,720,600 A | 1/1988 | Beech, Jr. et al. |
| 4,720,601 A | 1/1988 | Suzukamo et al. |
| 4,740,652 A | 4/1988 | Frame |
| 4,788,376 A | 11/1988 | Mazurek et al. |
| 4,806,701 A | 2/1989 | Shum |
| 4,808,763 A | 2/1989 | Shum |
| 4,855,528 A | 8/1989 | Young et al. |
| 4,864,068 A | 9/1989 | Shamshoum |
| 4,873,392 A | 10/1989 | Le Van Mao |
| 4,908,471 A | 3/1990 | Leuck et al. |
| 4,950,828 A | 8/1990 | Shum |
| 4,975,402 A | 12/1990 | Le Van Mao et al. |
| 5,026,938 A | 6/1991 | Shum |
| 5,087,789 A | 2/1992 | McDaniel et al. |
| 5,107,050 A | 4/1992 | Gaffney et al. |
| 5,130,458 A | 7/1992 | Wu |
| 5,135,861 A | 8/1992 | Pavilon |
| 5,386,071 A | 1/1995 | Kuchar et al. |
| 5,414,160 A | 5/1995 | Sato et al. |
| 5,519,101 A | 5/1996 | Nubel et al. |
| 5,550,306 A | 8/1996 | Chauvin et al. |
| 5,625,109 A | 4/1997 | Gupta |
| 5,672,800 A | 9/1997 | Mathys et al. |
| 5,693,793 A | 12/1997 | Ritz et al. |
| 5,753,474 A | 5/1998 | Ramey |
| 5,801,286 A | 9/1998 | Besson et al. |
| 5,856,604 A | 1/1999 | Stine et al. |
| 5,877,372 A | 3/1999 | Evans et al. |
| 5,895,830 A | 4/1999 | Stine et al. |
| 5,962,604 A | 10/1999 | Rath |
| 5,969,178 A | 10/1999 | Okamoto et al. |
| 5,990,367 A | 11/1999 | Stine et al. |
| 5,994,601 A | 11/1999 | Nierlich et al. |
| 6,111,160 A | 8/2000 | Powers et al. |
| 6,143,942 A | 11/2000 | Verrelst et al. |
| 6,239,321 B1 | 5/2001 | Mossman et al. |
| 6,300,536 B1 | 10/2001 | Verrelst et al. |
| 6,323,384 B1 | 11/2001 | Powers et al. |
| 6,331,580 B1 | 12/2001 | Molnar |
| 6,358,717 B1 | 3/2002 | Blaschek et al. |
| 6,376,731 B1 | 4/2002 | Evans et al. |
| 6,600,081 B2 | 7/2003 | Manzer et al. |
| 6,649,757 B2 | 11/2003 | Kuroda et al. |
| 6,660,898 B1 | 12/2003 | Pyhälahti et al. |
| 6,689,927 B1 | 2/2004 | Frame et al. |
| 6,770,791 B2 | 8/2004 | Mathys et al. |
| 6,875,899 B2 | 4/2005 | Martens et al. |
| 6,884,916 B1 | 4/2005 | Brown et al. |
| 7,002,053 B2 | 2/2006 | Nierlich et al. |
| 7,012,167 B2 | 3/2006 | Kahn |
| 7,038,101 B2 | 5/2006 | Nurminen et al. |
| 7,067,708 B2 | 6/2006 | Manzer et al. |
| 7,161,053 B2 | 1/2007 | Beckmann et al. |
| 7,169,588 B2 | 1/2007 | Burch et al. |
| 7,183,450 B2 | 2/2007 | Brown et al. |
| 7,238,844 B2 | 7/2007 | Mathys et al. |
| 7,271,304 B2 | 9/2007 | Du Toit |
| 7,304,196 B2 | 12/2007 | Purola et al. |
| 7,329,788 B2 | 2/2008 | Tiitta et al. |
| 7,345,212 B2 | 3/2008 | Beadle et al. |
| 7,439,409 B1 | 10/2008 | Jan et al. |
| 7,498,473 B2 | 3/2009 | Zhou et al. |
| 7,553,997 B2 | 6/2009 | Stark et al. |
| 7,682,811 B2 | 3/2010 | Leschine et al. |
| 7,833,778 B2 | 11/2010 | Butler, III |
| 8,193,402 B2 | 6/2012 | Gruber et al. |
| 2002/0183578 A1 | 12/2002 | Commereuc et al. |
| 2003/0055179 A1 | 3/2003 | Ota et al. |
| 2004/0044261 A1 | 3/2004 | Feng et al. |
| 2005/0069998 A1 | 3/2005 | Ballesteros Perdices et al. |
| 2005/0112739 A1 | 5/2005 | Golubkov |
| 2005/0176870 A1 | 8/2005 | Kulkarni et al. |
| 2005/0183325 A1 | 8/2005 | Sutkowski |
| 2005/0228203 A1 | 10/2005 | Manzer |
| 2005/0228204 A1 | 10/2005 | Manzer |
| 2006/0111599 A1 | 5/2006 | Lamprecht et al. |
| 2007/0039239 A1 | 2/2007 | Forester et al. |
| 2007/0092957 A1 | 4/2007 | Donaldson et al. |
| 2007/0135665 A1 | 6/2007 | Wiese et al. |
| 2007/0148751 A1 | 6/2007 | Griffin et al. |
| 2007/0191662 A1 | 8/2007 | Oikarinen et al. |
| 2007/0202062 A1 | 8/2007 | Workman et al. |

| | | | |
|---|---|---|---|
| 2007/0215519 | A1 | 9/2007 | Dierickx |
| 2007/0259410 | A1 | 11/2007 | Donaldson et al. |
| 2007/0259411 | A1 | 11/2007 | Bramucci et al. |
| 2007/0264697 | A1 | 11/2007 | Taguchi et al. |
| 2007/0292927 | A1 | 12/2007 | Donaldson et al. |
| 2008/0009656 | A1 | 1/2008 | D'Amore et al. |
| 2008/0015395 | A1* | 1/2008 | D'amore et al. ............... 568/697 |
| 2008/0015397 | A1 | 1/2008 | D'Amore et al. |
| 2008/0045754 | A1 | 2/2008 | D'Amore et al. |
| 2008/0057555 | A1 | 3/2008 | Nguyen |
| 2008/0124774 | A1 | 5/2008 | Bramucci et al. |
| 2008/0131948 | A1 | 6/2008 | Manzer et al. |
| 2008/0132730 | A1 | 6/2008 | Manzer et al. |
| 2008/0132732 | A1 | 6/2008 | Manzer et al. |
| 2008/0132741 | A1 | 6/2008 | D'Amore et al. |
| 2008/0138870 | A1 | 6/2008 | Bramucci et al. |
| 2008/0182308 | A1 | 7/2008 | Donaldson et al. |
| 2008/0220488 | A1 | 9/2008 | D'Amore et al. |
| 2008/0227940 | A1 | 9/2008 | Wilson et al. |
| 2008/0234523 | A1 | 9/2008 | Manzer et al. |
| 2008/0248540 | A1 | 10/2008 | Yang |
| 2008/0261230 | A1 | 10/2008 | Liao et al. |
| 2008/0274525 | A1 | 11/2008 | Bramucci et al. |
| 2008/0312482 | A1 | 12/2008 | Jan et al. |
| 2008/0312485 | A1 | 12/2008 | Takai et al. |
| 2009/0030239 | A1 | 1/2009 | D'Amore et al. |
| 2009/0061492 | A1 | 3/2009 | Benning et al. |
| 2009/0068714 | A1 | 3/2009 | Leschine et al. |
| 2009/0099401 | A1 | 4/2009 | D'Amore et al. |
| 2009/0155869 | A1 | 6/2009 | Buelter et al. |
| 2009/0171129 | A1 | 7/2009 | Evanko et al. |
| 2009/0182163 | A1 | 7/2009 | Foo et al. |
| 2009/0215137 | A1 | 8/2009 | Hawkins et al. |
| 2009/0226990 | A1 | 9/2009 | Hawkins et al. |
| 2009/0226991 | A1 | 9/2009 | Feldman et al. |
| 2009/0239009 | A1 | 9/2009 | Tanaka |
| 2009/0240068 | A1 | 9/2009 | Rajendran |
| 2009/0247799 | A1 | 10/2009 | Myllyoja et al. |
| 2009/0299109 | A1 | 12/2009 | Gruber et al. |
| 2010/0108568 | A1 | 5/2010 | De Klerk |
| 2010/0137647 | A1 | 6/2010 | Bradin |
| 2010/0216958 | A1 | 8/2010 | Peters et al. |
| 2011/0087000 | A1 | 4/2011 | Peters et al. |
| 2011/0288311 | A1 | 11/2011 | Frost et al. |
| 2011/0288352 | A1 | 11/2011 | Peters et al. |
| 2012/0171741 | A1 | 7/2012 | Peters et al. |
| 2012/0238787 | A1 | 9/2012 | Gruber et al. |

FOREIGN PATENT DOCUMENTS

| | | |
|---|---|---|
| JP | 2001-2600 A | 1/2001 |
| JP | 2006-306731 A | 11/2006 |
| JP | 2007-61763 A | 3/2007 |
| WO | WO 03/053570 A1 | 7/2003 |
| WO | WO 03/070671 A1 | 8/2003 |
| WO | WO 2005/065393 A2 | 7/2005 |
| WO | WO 2005/073172 A1 | 8/2005 |
| WO | WO 2005/092821 A1 | 10/2005 |
| WO | WO 2007/091862 A1 | 8/2007 |
| WO | WO 2008/058664 A1 | 5/2008 |
| WO | WO 2008/113492 A1 | 9/2008 |
| WO | WO 2009/038965 A1 | 3/2009 |
| WO | WO 2009/039000 A2 | 3/2009 |
| WO | WO 2009/039333 A1 | 3/2009 |
| WO | WO 2009/039335 A1 | 3/2009 |
| WO | WO 2009/039347 A1 | 3/2009 |

OTHER PUBLICATIONS

Young, "Written Opinion of the International Searching Authority," 9 pages, from PCT appl. No. PCT/US11/20549, United States Patent and Trademark Office, Alexandria, Virginia, United States (mailed Mar. 11, 2011).

"International Preliminary Report on Patentability," 10 pages, International Patent Appl. No. PCT/US2010/025234, United States Patent and Trademark Office (issued Aug. 30, 2011).

"International Search Report," 2 pages, from International Appl. No. PCT/US2010/051641, United States Patent and Trademark Office, Alexandria, Virginia, USA (mailed Dec. 2, 2010).

"International Search Report," 2 pages, International Patent Appl. No. PCT/US2011/035769, United States Patent and Trademark Office (Aug. 17, 2011).

"International Search Report," 2 pages, International Patent Appl. No. PCT/US2011/058766, United States Patent and Trademark Office (Feb. 17, 2012).

"International Search Report," 4 pages, International Patent Application No. PCT/US2008/085423, United States Patent and Trademark Office, Alexandria, Virginia, United States (mailed Jul. 15, 2009).

"International Search Report," 5 pages, International Patent Appl. No. PCT/US2010/025234, United States Patent and Trademark Office (mailed Jun. 15, 2010).

"Part 2, Oxidative Dehydrodimerization of Alkenes", Catalysis Today, (1992), 343-393.

"Written Opinion of the International Searching Authority," 5 pages, International Patent Appl. No. PCT/US2011/035769, United States Patent and Trademark Office (Aug. 17, 2011).

"Written Opinion of the International Searching Authority," 5 pages, International Patent Appl. No. PCT/US2011 /058766, United States Patent and Trademark Office (Feb. 17, 2012).

"Written Opinion of the International Searching Authority," 6 pages, International Patent Application No. PCT/US2008/085423, United States Patent and Trademark Office, Alexandria, Virginia, United States (mailed Jul. 15, 2009).

"Written Opinion of the International Searching Authority," 7 pages, from International Appl. No. PCT/US10/51641, United States Patent and Trademark Office, Alexandria, Virginia, USA (mailed Dec. 2, 2010).

"Written Opinion of the International Searching Authority," 9 pages, International Patent Appl. No. PCT/US2010/025234, United States Patent and Trademark Office (mailed Jun. 15, 2010).

Amin et al., "Dealuminated ZSM-5 Zeolite Catalyst for Ethylene Oligomerization to Liquid Fuels", Journal of Natural Gas Chemistry 2002, 11, 79-86.

Angermayr et al., "Energy Biotechnology with Cyanobacteria" Current Opinion in Biotechnology Jun. 2009, vol. 20, pp. 257-263.

ASTM International, "Standard Specification for Automotive Spark-Ignition Engine Fuel," Designation D4814-11, 31 pages (Jul. 2011).

ASTM International, "Standard Specification for Aviation Gasolines," Designation D910-11, 8 pages (May 2011).

ASTM International, "Standard Specification for Aviation Turbine Fuels," Designation D1655-11a, 16 pages (Aug. 2011).

ASTM International, "Standard Specification for Diesel Fuel Oils," Designation D975-11, 25 pages (Apr. 2011).

ASTM test method D 6866-05, "Determining the Biobased Content of Natural Range Materials Using Radiocarbon and Isotope Ratio Mass Spectrometry Analysis" 14 pages, 2005.

Atsumi "Direct photosynthetic recycling of carbon dioxide to isobutyraldehyde" Nature Biotechnology, Nov. 15, 2009, vol. 27, pp. 1177-1182.

Atsumi et al., "Non-fermentative Pathways for Synthesis of Branched-Chain Higher Alcohols as Biofuels", Nature, 2008, 451, p. 86-89.

Atsumi et al., Online Supplementary Information of "Non-fermentative Pathways for Synthesis of Branched-Chain Higher Alcohols as Biofuels", Nature, 2008, pp. 1-8.

Batist et al. "The catalytic oxidation of 1-butene over bismuth molybdate catalysts: II. Dependence of activity and selectivity on the catalyst composition" Journal of Catalysis, Feb. 1966, vol. 5, pp. 55-64.

Bekker and Prinsloo, "Butene Oligomerization over Phosphoric Acid: Structural Characterization of Products," Ind. Eng. Chem. Res. 48(22):10156-10162 (2009).

Bezergianni et al., "Catalytic Hydrocracking of Fresh and Used Cooking Oil," Ind. Eng. Chem. Res. 48:8402-8406 (2009).

Busca, "Acid Catalysts in Industrial Hydrocarbon Chemistry" Chemical Reviews, 2007, 107, 5366-5410.

Buyanov et al. "Catalysts and Processes for Paraffin and Olefin Dehydrogenation," Kinetics and Catalysis, Jan. 2001, vol. 42, pp. 64-75.

Čejka et al., "Acid-Catalyzed Sythesis of Mono- and Dialkyl Benzenes over Zeolites: Active Sites, Zeolite Topology, and Reaction Mechanisms", Catalysis Review 2002, 44(3), 375-421.

Chen and Yan, "M2 Forming—A Process for Aromatization of Light Hydrocarbons", Ind. Eng. Chem. Process Des. Dev., 25 (1986), 151-155.

Connor et al. "Engineering of an *Escherichia coli* Strain for the Production of 3-Methyl-l-Butanol" Applied Envirionmental Microbiology, Sep. 2008, vol. 74, pp. 5769-5775.

de Klerk, "Can Fischer-Tropsch Syncrude Be Refined to On-Specification Diesel Fuel?" Energy Fuels 23:4593-4604 (2009).

de Klerk, "Distillate Production by Oligomerization of Fischer-Tropsch Olefins over Solid Phosphoric Acid," Energy Fuels 20:439-445 (2006).

de Klerk, "Fischer-Tropsch Refining," Title page and pp. i-xi, Ph.D. Thesis, University of Pretoria (Feb. 2008).

de Klerk, "Fischer-Tropsch refining: technology selection to match molecules," Green Chem. 10:1249-1279 (2008).

Delhomme et al. "Succinic acid from renewable resources as a C4 building-block chemical—a review of the catalytic possibilities in aqueous media" Green Chemistry, Jan. 2009, vol. 11(1), pp. 13-26.

Dexter et al. "Metabolic Engineering of Cyanobacteria for Ethanol Production" Energy & Environmental Science, Aug. 2009, vol. 2(8), pp. 857-864.

Dhaliwal et al. "Measurement of the Unsaturation of Butyl Rubbers by the Iodine Index Method" Rubber Chemistry and Technology, 1994, vol. 67, pp. 567-581.

Frame et al., "High Octane Gasoline from Field Butanes by the UOP Indirect Alkylation (InAlk) Process", Erdöl, Erdgas Kohle, 114(7-8) (1998), 385-387.

Genomatica, Inc. press release, 10 pages (2008/2009).

Gnep et al., "Conversion of Light Alkanes to Aromatic Hydrocarbons; II. Role of Gallium Species in Propane Transformation on GaHZSM5 Catalysts", Applied Catalysis 1988, 43, 155-166.

Guisnet et al., "Aromatization of short chain alkanes on zeolite catalysts," Appl. Catal. A, 1992, 89, p. 1-30.

Hileman et al., "Near-Term Feasibility of Alternative Jet Fuels," 152 pages, RAND Corporation, 2009.

Hobbie et al., "Intramolecular, compound-specific, and bulk carbon isotope patterns in $C_3$ and $C_4$ plants: a review and synthesis," New Phytologist, 2004, 161, p. 371-385.

Jung et al. "Oxidative Dehydrogenation of $C_4$ Raffinate-3 to 1,3-Butadiene in a Dual-bed Reaction System Comprising $ZnFe_2O_4$ and $Co_9Fe_3Bi_1Mo_{12}O_{51}$ Catalysts: A Synergistic Effect of $ZnFe_2O_4$ and $Co_9Fe_3Bi_1Mo_{12}O_{51}$ Catalysts" Catalysis Letters, Jul. 2008 vol. 123, pp. 239-245.

Kamath "Process Analysis for Dimerization of Isobutene by Reactive Distillation" Industrial & Engineering Chemistry Research, Feb. 1, 2006, vol. 45, pp. 1575-1582.

Krishnan et al. "Oxidative Dehydrogenation of 1-Butene over Manganese Oxide Octahedral Molecular Sieves" Journal of Catalysis, Jun. 1999, vol. 184, pp. 305-315.

Lamprecht, "Fischer-Tropsch Fuel for Use by the U.S. Military as Battlefield-Use Fuel of the Future", Energy & Fuels 2007, 21, 1448-1453.

Latshaw "Dehydration of Isobutane to Isobutene in a Slurry Reactor" Department of Energy Topical Report, 84 pages, Feb. 1994.

Lopez Nieto et al. "Selective Oxidation of n-Butane and Butenes over Vanadium-Containing Catalysts" Journal of Catalysis, Jan. 2000, vol. 189, pp. 147-157.

Mazumder et al., "Oxidative Dehydrodimerization and Aromatization of Isobutene on $Bi_2O_3$-$SnO_2$ Catalysts", Applied Catalysis A: General, 245 (2003), 87-102.

McAvoy, "Notice of Allowability," 5 pages, U.S. Appl. No. 12/327,723 (mailed Mar. 9, 2012).

McAvoy, "Office Action Summary," 5 pages, U.S. Appl. No. 12/327,723 (mailed Jan. 4, 2012).

McAvoy, "Office Action Summary," 6 pages, U.S. Appl. No. 13/441,468 (mailed Aug. 16, 2012).

McAvoy, "Office Action Summary," 7 pages, U.S. Appl. No. 12/327,723 (mailed Jan. 11, 2011).

McAvoy, "Office Action Summary," 7 pages, U.S. Appl. No. 13/441,459 (mailed Jul. 20, 2012).

McAvoy, "Office Action Summary," 8 pages, U.S. Appl. No. 12/327,723 (mailed Apr. 8, 2011).

McAvoy, "Supplemental Notice of Allowability," 4 pages, U.S. Appl. No. 12/327,723 (mailed Apr. 27, 2012).

Pines and Haag, "Alumina: Catalyst and Support. IX. The Alumina Catalyzed Dehydration of Alcohols," J. Am. Chem. Soc. 83:2847-2852 (1961).

Rossberg et al., "Chlorinated Hydrocarbons," in Ullmann's Encyclopedia of Industrial Chemistry 2002, Wiley VCH, published online Jul. 15, 2006.

Rumizen, "ASTM Aviation Synthetic Fuel Specification," $3^{rd}$ International Conference on Biofuel Standards, World Biofuels Markets Congress, 19 pages (Mar. 2010).

Saad et al., "Characterization of various zinc oxide catalysts and their activity in the dehydration-dehydrogenation of isobutanol" Journal of the Serbian Chemical Society 2008, vol. 73(10), pp. 997-1009.

Sakuneka et al., "Synthetic Jet Fuel Production by Combined Propene Oligomerization and Aromatic Alkylation over Solid Phosphoric Acid", Ind. Eng. Chem. Res., 47 (2008), 1828-1834.

Savidge and Blair, "Intramolecular Carbon Isotopic Composition of Monosodium Glutamate: Biochemical Pathways and Product Source Identification," J. Agric. Food Chem. 2005, 53, p. 197-201.

Schmidt, "Fundamentals and systematics of the non-statistical distributions of isotopes in natural compounds," Naturwissenschaften 2003, 90, p. 537-552.

Solymosi et al., Aromatization of Isobutane and Isobutene Over $Mo_2C$/ZSM-5 Catalyst, Applied Catalysis A: General, 278 (2004), 111-121.

Speiser et al., "Catalytic Ethylene Dimerization and Oligomerization: Recent Developments with Nickel Complexes Containing P,N-Chelating Ligands", Accounts of Chemical Research 2005, 38, 784-793.

Subramani et al. "A Review of Recent Literature to Search for an Efficient Catalytic Process for the Conversion of Syngas to Ethanol" Energy and Fuels, Jan. 31, 2008 vol. 22, pp. 814-839.

Suresh et al., "Engineering Aspects of Industrial Liquid-Phase Air Oxidation of Hydrocarbons", Ind. Eng. Chem. Res. 39 (2000), 3958-3997.

Syu, "Biological production of 2,3-butanediol" Applied Microbiology and Biotechnology, Jan. 2001, vol. 55(1), pp. 10-18.

Taubert et al., "Dehydrodimerization of Isobutene to 2,5-Dimethyl-1,5-hexadiene over Bismuth(III)-Oxide and Various Additives", Chem. Eng. Technol., 29(4) (2006), 468-472.

Threadingham et al., "Rubber, 3. Synthetic," in Ullmann's Encyclopedia of Industrial Chemistry 2002, Wiley VCH, published online Apr. 30, 2004.

Tiwari et al. "Effect of aluminium oxide on the properties of Cu-Mo catalyst in the oxidative dehydrogenation of butene-1 to butadiene" Journal of Catalysis, Nov. 1989, vol. 120, pp. 278-281.

Toledo-Antonio et al. "Correlation between the magnetism of non-stoichiometric zinc ferrites and their catalytic activity for oxidative dehydrogenation of 1-butene" Applied Catalysis A: General, Aug. 2002, vol. 234, pp. 137-144.

UOP, "Cyclar™" (process fact-sheet).

UOP, UOP Indirect Alkylation (InAlk™) Process Mixed Olefins Application (process fact sheet).

Weber et al., "13C-Pattern of Natural Glycerol: Origin and Practical Importance," J. Agric. Food Chem. 1997, 45, p. 2042-2046.

Wyman, "Potential Synergies and Challenges in Refining Cellulosic Biomass to Fuels, Chemicals, and Power", 2003 Biotechnological Progress 19:254-62.

\* cited by examiner

Dehydration of Isobutanol

Dehydration Reactor Schematic

Equilibrium Composition of C₄ Isomers vs. Temp.

Isoprene via Prins Reaction

Dehydrogenation of n-butane

Dehydrogenation of 1-butene to 1,3-butadiene

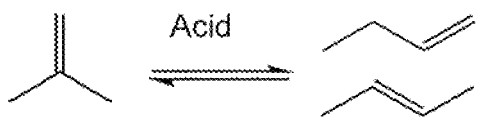
Figure 7: Skeletal Rearrangement of Isobutene
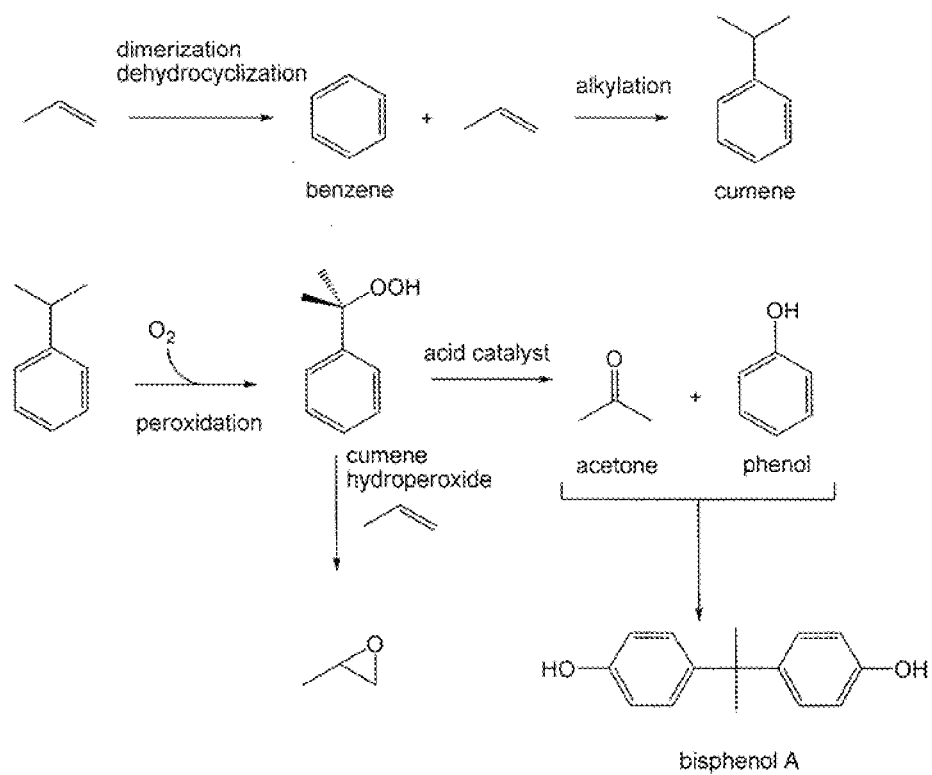
Figure 8

Integrated System to Convert Isobutanol to Renewable p-Xylene

INTEGRATED METHODS OF PREPARING RENEWABLE CHEMICALS

CROSS REFERENCE TO RELATED APPLICATIONS

This application claims priority to U.S. Provisional Appl. No. 61/293,459, filed Jan. 8, 2010, which is herein incorporated by reference in its entirety for all purposes.

BACKGROUND OF THE INVENTION

Conventional transportation fuels and chemicals (e.g., monomers, polymers, plasticizers, adhesives, thickeners, aromatic and aliphatic solvents, etc.) are typically derived from non-renewable raw materials such as petroleum. However, the production, transportation, refining and separation of petroleum to provide transportation fuels and chemicals is problematic in a number of significant ways.

For example, petroleum (e.g., crude oil and/or natural gas) production poses a number of environmental concerns. First, the history of petroleum production includes many incidents where there have been uncontrolled releases of crude petroleum during exploration and production (e.g., drilling) operations. While many of these incidents have been relatively minor in scale, there have been a number of incidents that have been significant in scale and environmental impact (e.g., BP's Deepwater Horizon incident, Mississippi Canyon, Gulf of Mexico, 2010).

World petroleum supplies are finite. Thus, as world petroleum demand has increased (84,337 M bpd worldwide in 2009; *US Energy Information Administration*), easily accessible reserves have been depleted. Accordingly, petroleum exploration and production operations are more frequently conducted in remote and/or environmentally sensitive areas (e.g., deepwater offshore, arctic regions, wetlands, wildlife preserves, etc.). Some remote locations require highly complex, technically challenging solutions to locate and produce petroleum reserves (e.g., due to low temperatures, water depth, etc.). Accordingly, the potential for large-scale environmental damage resulting from uncontrolled discharge of petroleum during such complex, technically challenging exploration and production operations is substantively increased.

In addition, when petroleum is produced in remote areas and/or areas which do not have infrastructure (e.g., refineries) to further process petroleum into useful products, the produced petroleum must be transported (e.g., via pipeline, rail, barge, ship, etc.), often over significant distances, to terminal points where the petroleum products may be refined and/of processed. Transportation of petroleum is also an operation with associated risk of accidental discharge of petroleum in the environment, with concomitant environmental damage, and there have been a number of significant incidents (e.g., Exxon's Valdez tanker spill, Prince William Sound, Ak., 1989). Furthermore, much of the world's proven petroleum reserves are located in regions which are politically unstable. Accordingly, supplies of petroleum from such regions may be uncertain since production of petroleum or transportation of petroleum products from such regions may be interrupted.

Petroleum is a complex mixture of chemical compounds. Crude petroleum comprises chemical entities from very the simple, e.g., helium and methane prevalent in natural gas, to the complex, e.g., asphaltenes and heterocyclic organic compounds prevalent in heavy, sour crude oil. Furthermore, crude petroleum is typically co-produced with varying amounts of formation water (e.g., water from the rock formation from which the petroleum was produced), often as stable emulsion, with salts, metals and other water-soluble compounds dissolved in the formation water. Crude oil may also contain varying amounts of particulate salts, metals, sediments, etc. Accordingly, crude oil streams are typically desalted, then allowed to settle and phase-separate into crude and water fractions, reducing the water content of the crude and the level of undesired components such as salts, metals, silt, sediment, etc. which may be present in the crude. Such undesired components are generally problematic in further processing and/or refining of petroleum into commercially useful fractions. For example, certain unit operations in the refining process may be sensitive to water, salt or sediment. Further, piping, storage and process vessels employed in the transport, storage and processing of petroleum is prone to corrosion, which may be accelerated and/or exacerbated by the presence of salt and/or water in the petroleum feedstock.

Desalting processes typically require the use of large quantities of water, which also may be heated, to extract salt and soluble metals from the crude oil. Further, the crude stream to be desalted is also generally heated to effect mixing with the extraction water. The resulting emulsions may then be treated with demulsifying agent and allowed to settle prior to further processing. Such desalting (and settling) may be time consuming, and may require (i) large quantities of water to extract the undesirable components, (ii) large amounts of energy to heat the water and/or crude stream(s) to effect mixing, and (iii) the use of substantial quantities of chemical agents to treat the crude (e.g., demulsifiers). As a result, large quantities of contaminated water are produced in desalting operation which must be treated to remove residual oil, dissolved salts, metals, water-soluble organics, demulsifiers, etc.

Furthermore, crude petroleum from regions, different subterranean reservoirs within a region, or even from different strata within a single field may have different chemical compositions. For example, crude oils can range from "light, sweet" oils which generally flow easily, and have a higher content of lower molecular weight hydrocarbons and low amounts of contaminants such as sulfur, to heavy, sour oils, which may contain a large fraction of high molecular weight hydrocarbons, large amounts of salts, sulfur, metals and/or other contaminants, and may be very viscous and require heating to flow. Furthermore, the relative amounts of the constituent fractions (e.g., light, low molecular weight hydrocarbons vs. heavier, higher molecular weight hydrocarbons) of the various grades or types of crude oil varies considerably. Thus, the chemical composition of the feedstock for a refinery may vary significantly, and as a result, the relative amounts of the hydrocarbon streams produced may vary as a function of the crude feed.

Once the crude feedstock is sufficiently treated to remove undesired impurities or contaminants, it can then be subject to further processing and/or refining. The crude feedstock is typically subject to an initial distillation, wherein the various fractions of the crude are separated into distillate fractions based on boiling point ranges. This is a particularly energy intensive process, as this separation is typically conducted on a vast scale, and most or all of the feedstock is typically heated in the distillation unit(s) to produce various distillate fractions. Furthermore, since the crude composition is quite complex, containing hundreds of compounds (if not more), each fraction may contain many different compounds, and the composition and yield of each distillate fraction may vary depending on the type and composition of crude feedstock. Depending on the desired product distribution on the back end of a refining operation, a number of additional refining steps may be performed to further refine and/or separate the distillate streams, each of which may require additional equipment and energy input.

For example, higher boiling fractions from an initial distillation may be subject to further distillation (e.g., under vacuum) to separate the mixture even further. Alternatively, heavy fractions from an initial distillation may be subject to "cracking" (e.g., catalytic cracking) at high temperatures to reduce the average molecular weight of the components of the feed stream. Since lighter hydrocarbon fractions (e.g., containing less than 20 carbon atoms) generally have greater commercial value and utility than heavier fractions (e.g., those containing more than 20 carbon atoms), cracking may be performed to increase the value and/or utility of a stream from an initial distillation. However, such cracking operations are typically very energy intensive since high temperatures (e.g., 500° C.) are generally required to effect the breakdown of higher molecular weight hydrocarbons into lower molecular weight components. Furthermore, the output from such cracking operations is also a complex mixture, and accordingly, may require additional separation (e.g., distillation) to separate the output stream into useful and/or desired fractions having target specifications, e.g., based on boiling point range or chemical composition.

Accordingly, the various components streams produced from petroleum refining and/or processing are generally mixtures. The homogeneity or heterogeneity of those mixtures may be a factor of the character of the crude feedstock, the conditions at which separations are conducted, the characteristics of a cracked stream, and the specifications of an end user for purity of a product stream. However, in practical terms, higher purity streams will require more rigorous separation conditions to isolate a desired compound from related compounds with similar boiling points (e.g., compounds having boiling points within 20, 10, or 5° C. of each other). Such rigorous separations generally require large process units (e.g., larger distillation columns) to separate more closely related compounds (e.g., compounds which have relatively close boiling points).

Furthermore, in addition to the above-described environmental concerns and energy/infrastructure costs associated with petroleum production and refining, there is mounting concern that the use of petroleum as a basic raw material in the production of chemical feedstocks and fuels contributes to environmental degradation (e.g., global warming) via generation and/or release of oxides of carbon. For example, burning a gallon of typical gasoline produces over 19 pounds of carbon dioxide. Because no carbon dioxide is consumed by a refinery in the manufacture of gasoline, the net carbon dioxide produced from burning a gallon of petroleum-derived gasoline is at least as great as the amount of carbon contained in the fuel, and is typically higher when the combustion of additional petroleum required to power the refinery (e.g., for separation of petroleum to produce the gasoline) and to power the transportation vehicles, pumps along pipelines, ships, etc. that bring the fuel to market is considered. Likewise, the production of basic chemicals (e.g., ethylene, propylene, butenes, butadiene, and aromatics such as benzene, toluene, and xylenes) from petroleum does not consume carbon dioxide, and the energy required to power the refinery to produce such chemicals and the transportation vehicles to deliver those chemicals also generate carbon dioxide.

In contrast to fossil fuels and petroleum derived chemicals, the net carbon dioxide produced by burning a gallon of biofuel or biofuel blend, or by producing biomass derived chemicals is less than the net carbon dioxide produced by burning a gallon of petroleum derived fuel or in producing chemicals from petroleum. In addition, biomass-derived chemical and fuel production has far fewer environmental hazards associated with it, since production of biomass-derived fuels requires no drilling operations. Further, biomass-derived chemical and fuel facilities can be located in a wide range of locations relative to petroleum refineries, essentially almost anywhere appropriate feedstocks are available (e.g., where sufficient amounts of suitable plant matter are available). Thus, the requirement for transport of feedstock can minimized, as are the associated energy costs of such transport. Further, even if transport of raw materials is needed, the environmental hazards of a spill of a typical biomass feedstock (e.g., corn) are negligible. Furthermore, biomass-derived product streams are typically far less complex mixtures than product streams from petroleum refining operations. Thus, far less energy may be required to obtain high purity product streams from biomass-based chemical production operations.

However, most biofuels and biomass-derived organic chemicals are produced from relatively expensive feedstocks (compared to petroleum), or are produced by processes which may be relatively inflexible or cannot readily adapt to changes in raw material costs or product prices. As a result, many biomass-based processes have difficulty competing economically with petroleum-based (e.g. refinery) processes.

SUMMARY OF THE INVENTION

The present invention is directed to an integrated process for producing a mixture of renewable biofuels and/or biofuel precursors, as well as a variety of different renewable chemicals from renewable ethanol and renewable isobutanol.

In various embodiments, the present invention is directed to an integrated process for preparing renewable hydrocarbons from renewable isobutanol and renewable ethanol, comprising dehydrating the renewable isobutanol, thereby forming a renewable butene mixture comprising one or more renewable linear butenes and renewable isobutene; dehydrating the renewable ethanol, thereby forming renewable ethylene; and reacting at least a portion of the renewable butene mixture and at least a portion of the renewable ethylene to form one or more renewable $C_3$-$C_{16}$ olefins.

In other embodiments, the integrated process further comprises forming renewable hydrogen by one or more of: (i) dehydrogenating at least a portion of linear butenes formed by dehydrating renewable isobutanol and/or one or more renewable $C_4$-$C_{16}$ olefins isolated from renewable $C_3$-$C_{16}$ olefins formed from reacting at least a portion of a renewable butene mixture and at least a portion of a renewable ethylene stream, thereby forming one or more renewable $C_4$-$C_{16}$ dienes and renewable hydrogen; (ii) dehydrocyclizing at least a portion of one or more renewable $C_6$-$C_{16}$ olefins isolated from the renewable $C_3$-$C_{16}$ olefins formed from reacting at least a portion of a renewable butene mixture and at least a portion of a renewable ethylene stream, thereby forming one or more renewable $C_6$-$C_{16}$ aromatics and renewable hydrogen; (iii) dehydrocyclizing at least a portion of one or more renewable $C_6$-$C_{16}$ dienes isolated from the renewable $C_4$-$C_{16}$ dienes formed by dehydrogenating at least a portion of linear butenes formed by dehydrating renewable isobutanol and/or one or more renewable $C_4$-$C_{16}$ olefins isolated from renewable $C_3$-$C_{16}$ olefins formed from reacting at least a portion of a renewable butene mixture and at least a portion of a renewable ethylene stream, to form one or more renewable $C_6$-$C_{16}$ aromatics and renewable hydrogen. The integrated process may also comprise hydrogenating at least a portion of the renewable $C_3$-$C_{16}$ olefin stream with renewable hydrogen, thereby forming a renewable saturated hydrocarbon fuel or fuel additive.

In still other embodiments, the process of the present invention further comprises controlling the total amount of renewable hydrogen produced by said dehydrogenating and/or dehydrocyclizing, so that the total amount of renewable hydrogen produced is consumed by hydrogenating the renewable $C_3$-$C_{16}$ olefins.

In other embodiments, the process of the present invention further comprises forming the one or more renewable $C_3$-$C_{16}$ olefins by disproportionation, metathesis, oligomerization, isomerization, alkylation, and combinations thereof.

The present integrated processes provide a flexible, environmentally sound method or system for producing biomass-derived chemicals, fuels and/or fuel blends. The present integrated process may provide product streams which can be readily and flexibly adapt to different biomass feedstocks, and may produce different mixtures of renewable products based on market demand. The present integrated process may also advantageously provide product streams having well-defined, predictable chemical compositions.

BRIEF DESCRIPTION OF THE DRAWINGS

FIG. 7 is a schematic of the acid-catalyzed rearrangement of isobutene

FIG. 8 is a schematic of the formation of benzene, acetone, propylene oxide, phenol, and bisphenol A from renewable propylene.

DETAILED DESCRIPTION OF THE INVENTION

Figure 1:
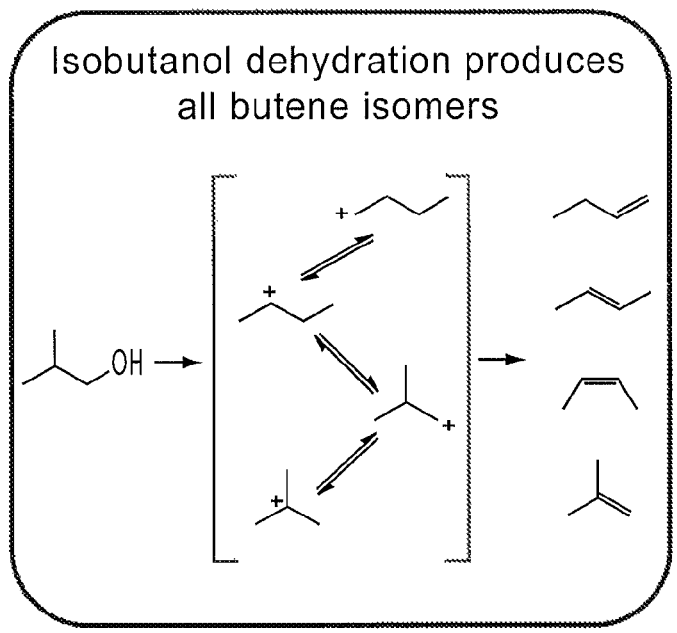
FIG. 1 is a schematic diagram of the formation of butene isomers from the dehydration of isobutanol.

All documents cited herein are incorporated by reference in their entirety for all purposes to the same extent as if each individual document was specifically and individually indicated to be incorporated by reference.

DEFINITIONS

"Renewably-based" or "renewable" denote that the carbon content of the renewable alcohol (and olefin, di-olefin, etc., or subsequent products prepared from renewable alcohols, olefins, di-olefins, etc. as described herein), is from a "new carbon" source as measured by ASTM test method D 6866-05, "Determining the Biobased Content of Natural Range Materials Using Radiocarbon and Isotope Ratio Mass Spectrometry Analysis", incorporated herein by reference in its entirety. This test method measures the $^{14}C/^{12}C$ isotope ratio in a sample and compares it to the $^{14}C/^{12}C$ isotope ratio in a standard 100% biobased material to give percent biobased content of the sample. "Biobased materials" are organic materials in which the carbon comes from recently (on a human time scale) fixated $CO_2$ present in the atmosphere using sunlight energy (photosynthesis). On land, this $CO_2$ is captured or fixated by plant life (e.g., agricultural crops or forestry materials). In the oceans, the $CO_2$ is captured or fixated by photosynthesizing bacteria or phytoplankton. For example, a biobased material has a $^{14}C/^{12}C$ isotope ratio greater than 0. Contrarily, a fossil-based material has a $^{14}C/^{12}C$ isotope ratio of about 0. The term "renewable" with regard to compounds such as alcohols or hydrocarbons (olefins, di-olefins, polymers, etc.) also refers to compounds prepared from biomass using thermochemical methods (e.g.; Fischer-Tropsch catalysts), biocatalysts (e.g., fermentation), or other processes, for example as described herein.

A small amount of the carbon atoms of the carbon dioxide in the atmosphere is the radioactive isotope $^{14}C$. This $^{14}C$ carbon dioxide is created when atmospheric nitrogen is struck by a cosmic ray generated neutron, causing the nitrogen to lose a proton and form carbon of atomic mass 14 ($^{14}C$), which is then immediately oxidized to carbon dioxide. A small but measurable fraction of atmospheric carbon is present in the form of $^{14}CO_2$. Atmospheric carbon dioxide is processed by green plants to make organic molecules during the process known as photosynthesis. Virtually all forms of life on Earth depend on this green plant production of organic molecules to produce the chemical energy that facilitates growth and reproduction. Therefore, the $^{14}C$ that forms in the atmosphere eventually becomes part of all life forms and their biological products, enriching biomass and organisms which feed on biomass with $^{14}C$. In contrast, carbon from fossil fuels does not have the signature $^{14}C$:$^{12}C$ ratio of renewable organic molecules derived from atmospheric carbon dioxide. Furthermore, renewable organic molecules that biodegrade to $CO_2$ do not contribute to global warming as there is no net increase of carbon emitted to the atmosphere.

Assessment of the renewably based carbon content of a material can be performed through standard test methods, e.g. using radiocarbon and isotope ratio mass spectrometry analysis. ASTM International (formally known as the American Society for Testing and Materials) has established a standard method for assessing the biobased content of materials. The ASTM method is designated ASTM-D6866.

The application of ASTM-D6866 to derive "biobased content" is built on the same concepts as radiocarbon dating, but without use of the age equations. The analysis is performed by deriving a ratio of the amount of radiocarbon ($^{14}C$) in an unknown sample compared to that of a modern reference standard. This ratio is reported as a percentage with the units "pMC" (percent modern carbon). If the material being analyzed is a mixture of present day radiocarbon and fossil carbon (containing very low levels of radiocarbon), then the pMC value obtained correlates directly to the amount of biomass material present in the sample.

Throughout the present specification, reference to alcohols, olefins, di-olefins, etc., and higher molecular weight materials (e.g., isooctene/isooctane, polymers, copolymers, etc.) made from such compounds is synonymous with "renewable" alcohols, "renewable" olefins, "renewable" di-olefins, etc., and "renewable" materials (e.g., "renewable" isooctene/isooctane, "renewable" polymers, "renewable" copolymers, etc.) unless otherwise indicated. Unless otherwise specified, all such chemicals produced by the integrated processes described herein are renewable unless explicitly stated otherwise.

Throughout the present specification, the terms "olefin" and "alkene" are used interchangeably to refer to a hydrocarbon having at least one carbon-carbon double bond. Alkenes or olefins having two carbon-carbon double bonds can be referred to as dienes, and if the two carbon-carbon double bonds are adjacent in the molecule (e.g., four adjacent $sp^2$ carbon atoms), the molecule can be termed a conjugated diene.

The renewable alcohols, olefins, di-olefins, polymers, aliphatic and aromatic organic compounds, etc. of the present invention have pMC values of at least about 1, 5, 10, 15, 20, 25, 30, 35, 40, 45, 50, 55, 60, 65, 70, 75, 80, 85, 90, 95, 100, inclusive of all values and subranges therebetween.

Throughout the present specification, the term "about" may be used in conjunction with numerical values and/or ranges. The term "about" is understood to mean those values near to a recited value. For example, "about 40 [units]" may mean within ±25% of 40 (e.g., from 30 to 50), within ±20%, ±15%, ±10%, ±9%, ±8%, ±7%, ±6%, ±5%, ±4%, ±3%, ±2%, ±1%, less than ±1%, or any other value or range of values therein or therebelow. Furthermore, the phrases "less than about [a value]" or "greater than about [a value]" should be understood in view of the definition of the term "about" provided herein.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc). Furthermore, all values within a given range may be an endpoint for the range encompassed thereby (e.g., the range 50-80 includes the ranges with endpoints such as 55-80, 50-75, etc.).

Throughout the present specification, the words "a" or "an" are understood to mean "one or more" unless explicitly stated otherwise. Further, the words "a" or "an" and the phrase "one or more" may be used interchangeably.

Overall Process

In various embodiments, the present invention is directed to an integrated process for preparing various renewable hydrocarbons from renewable ethanol and renewable isobutanol. The renewable ethanol and isobutanol can be sold as commodity chemicals directly, or dehydrated to their respective olefins (e.g. ethylene and isobutene and one or more renewable linear butenes—typically a mixture of isobutene, 1-butene and cis/trans-2-butene). The renewable ethylene and renewable butenes can then also either be sold directly, or further processed (e.g., separated or reacted) in a variety of different ways to produce a wide variety of renewable hydrocarbon product streams. In certain embodiments, further processing may comprise mixing the renewable ethylene and/or butenes with ethylene and/or butylene produced by conventional methods (e.g., petroleum cracking) to produce an array of hydrocarbon compounds comprising renewable carbon. Accordingly, such compounds, while not composed solely of renewable carbon, still comprise at least some renewable carbon, with concomitant environmental advantages as described herein.

For example, one renewable hydrocarbon product stream is renewable ethylene, produced from dehydration of renewable ethanol. The renewable ethylene produced thereby is generally of very high purity, and is easily separated from the unreacted feedstock of the dehydration reaction (typically aqueous ethanol and catalyst) by removal of the produced ethylene from the reaction space as a gas stream. The renewable ethylene can then be either sold directly as a feedstock, or subsequently converted to higher value renewable hydrocarbons, such as higher molecular weight olefins produced by oligomerization reactions (e.g. dimers, trimers, etc.), polymerized to form renewable polyethylene, oxidized form renewable ethylene oxide (which can be subsequently be polymerized to form renewable polyethylene oxide, or converted to other renewable polyethylene oxide derivatives), converted to dichloroethane (for subsequent conversion to vinyl chloride and polymerization thereof), used as a renewable feedstock for alkylating other olefins or aromatics (e.g., alkylation of benzene to produce ethylbenzene), etc.

Another renewable hydrocarbon product stream is renewable butene, produced from the dehydration of renewable isobutanol. The renewable butene formed thereby is typically a tunable mixture of butene isomers, which is easily separated from the isobutanol feed to the dehydration reaction, and can be sold directly as a mixture, reacted as a mixture to form other hydrocarbons (e.g., polybutenes), or the mixture of renewable butene isomers can be separated (e.g., by distillation, by selective conversion, etc.) into individual butene isomers, which can then either be sold individually as feedstocks, polymerized (e.g. to renewable polyisobutylene or butene copolymers), oligomerized (e.g., dimerized, trimerized, etc.) to form higher molecular weight olefins (e.g. isooctene or pentamethylheptenes), isomerized (e.g. isobutene isomerized to linear butenes, 1-butene isomerized to 2-butene, or 2-butene isomerized to 1-butene, etc.), dehydrogenated (e.g. to butadiene), as well as combinations of such processes, etc. In particular, isobutene dimers and trimers can be hydrogenated to provide, e.g., renewable isooctane and renewable pentamethylheptanes, both of which are useful as, e.g., renewable transportation fuels or renewable additives for transportation fuels.

In addition, the renewable olefins provided by the integrated processes described herein can also be reacted together, e.g., disproportionated, to provide olefins of varying carbon number (e.g., 3, 5, 7, etc.). For example, renewable ethylene and renewable 2-butene produced as described herein can be disproportionated using appropriate conditions (e.g., an appropriate metathesis catalyst) to provide renewable propylene. Renewable propylene produced by such a disproportionation process can be sold directly as a feedstock, or subsequently converted to other higher value renewable hydrocarbons by, e.g., oligomerization to produce higher olefins (e.g. dimers, trimers, etc.), polymerization to form polypropylene, oxidation to form propylene oxide (which can be subsequently be polymerized to form renewable polypropylene oxide, or converted to other renewable polypropylene oxide derivatives), oxidation to form acrylic acid (which may be further reacted to form a range of commercially significant acrylic esters), reaction with ammonia and oxygen to form acrylonitrile, reaction with benzene to produce acetone and phenol (e.g., via the cumene process), etc.

Similarly, disproportionation and/or oligomerization reactions of ethylene, butenes, propylene and oligomers thereof can be combined in various ways to produce a range of olefins having a desired number of carbon atoms. The various mono-olefins produced by such reactions can be dehydrogenated to form dienes or other polyenes (trienes, etc.) and renewable hydrogen as a valuable co-product. In addition, olefins and/or polyenes produced by these reactions can also be dehydrocyclized to form cyclic olefins (e.g., cyclohexene) or aromatics (e.g., benzene, xylenes), which also produces renewable hydrogen. Furthermore, the reactivity of olefins is suited to selective introduction of heteroatoms into the above-described olefins (e.g., oxygen, nitrogen, halogens, etc.), allowing access to a broad array of derivatives.

Thus, beginning with simple, renewable ethanol and isobutanol feedstocks, the integrated process of the present invention can provide essentially all of the commercially important hydrocarbons currently produced in petrochemical refineries (e.g., ethylene, propylene, butenes, butadiene, xylenes such as p-xylene, toluene, and benzene), and when coupled with additional processes, can produce virtually any fuel or chemical. In particular, the present invention provides a method for the production of benzene and xylene, commodity chemicals which serve as the building blocks from a vast array of intermediates and finished products. Furthermore, when the ethanol and isobutanol feedstocks are renewable, produced from biomass or other biological sources, the integrated process of the present invention can produce renewable hydrocarbons corresponding to the petroleum-derived hydrocarbons produced in a conventional petroleum refinery in a more environmentally sound and sustainable fashion. Further still, even in cases where the use of solely renewable feedstocks is not feasible and/or economical, supplementing traditional petroleum-derived hydrocarbon feedstocks (e.g., ethylene, butenes, etc.) with renewable feedstocks in integrated chemical processing and/or manufacturing operations can still provide substantive advantages (e.g., reduced environmental impact, carbon footprint, etc.) relative to traditional, "petroleum-only" operations.

In contrast to the present methods, petroleum-derived ethylene, butenes and/or propylene are typically produced in catalytic cracking of higher molecular weight hydrocarbons, as component in a complex mixture of hydrocarbons. Such mixtures typically include, among a range of product compounds, low molecular weight olefins such as propylene, butene, and butadiene, which may be difficult to separate due to their similar boiling points. Accordingly, purifying such a stream to produce a high-purity ethylene, propylene, butenes, or butadiene fractions is typically an energy intensive process. In fact, mixtures of ethylene, propylene, butene and butadiene are often sold directly as liquefied mixtures by refineries, as a commodity, rather than separating the individual fractions, due to the costs of equipment and energy required to separate the various components of such mixtures. However, if desired, the present integrated processes can provide such a mixture analogous to that provided by refinery cracking processes, thus supplying a typical refinery product for end users who rely on such mixed feedstocks. Furthermore, mixtures of hydrocarbons produced by the present methods typically have a well-defined composition due to the limited number of possible products associated with each individual process or reactive step. Accordingly, the present integrated methods may provide higher purity products requiring less additional processing and/or energy to separate. Alternatively, the present integrated process may provide mixed streams with simpler, well-defined compositions.

The relative amounts of product outputs produced in the processes described herein can be flexibly adjusted in various ways to adjust to, e.g., changing market demand for specific product streams or to maximize the overall value of the products produced. For example, the relative amounts of ethanol and isobutanol supplied to the process of the present invention can be adjusted, or the relative amounts of, e.g., ethylene and isobutene (and/or linear butenes, etc.) supplied to various unit operations can be adjusted to vary the product mix, and thereby maximize the economic value of the products produced. Since the catalysts described herein for producing renewable ethanol and renewable isobutanol use similar biomass raw material, the relative output from a given unit input of biomass can be adjusted as desired to a higher or lower fraction of either ethanol or isobutanol. As a result, varying demand for products produced downstream can be accommodated by adjusting relative production of ethanol and isobutanol (and intermediates and/or products subsequently formed therefrom).

For example, if market demand and/or market price for ethylene (or products formed therefrom) is high, the relative amount of ethanol feedstock can be increased, and accordingly, the amount of ethylene produced via dehydration of ethanol can be increased. Similarly, if market demand and/or market price for butylene(s) (or products formed therefrom) is high, the relative amount of isobutanol feedstock can be increased, and accordingly, the amount of butylene(s) produced via dehydration of isobutanol can be increased. In another case, if market demand and/or market price for propylene (or products prepared from propylene) increases, the relative amounts of renewable ethanol and isobutanol fed into the process can be adjusted to optimize the relative amounts of ethylene and 2-butene feedstocks for subsequent disproportionation to propylene. Similarly, in situations where fuel prices are high and/or fuel demand is high, the amount of isobutanol relative to ethanol fed into the process of the present invention can be increased to maximize production of isooctene and/or pentamethylheptenes (dimer and trimer of isobutylene), and optionally the relative amount of olefins fed to dehydrocyclization could be increased in order to supply the necessary hydrogen to reduce the isooctene and/or pentamethylheptenes to the respective isooctane and pentamethylheptanes.

Alternatively, if it is desirable to maximize the production of aromatics and dienes such as butadiene, the process can be adjusted to maximize production of butadiene and aromatics such as benzene and xylenes (and/or products downstream such as styrene, cumene, etc.), and the excess hydrogen produced from dehydrogenation of linear butenes to butadiene or aromatic-forming cyclodehydrogenations can be sold or utilized to hydrogenate isooctene and/or pentamethylheptenes to isooctane (e.g., for gasoline) and/or pentamethylheptanes (e.g., for jet fuel). Thus, the amount and composition of feedstocks fed to the present integrated process, and the relative quantities of produced product in the various unit operations described herein can be increased or decreased to maximize the overall value of the products produced while ensuring complete utilization of the renewable carbon and optionally hydrogen produced in the integrated process.

In certain embodiments, the process of the present invention utilizes most or all of all the carbon in the ethanol and isobutanol feedstock, and most or all of the renewable hydrogen produced by dehydrogenation and/or dehydrocyclization reactions, to form a renewable saturated hydrocarbon fuel or fuel active product stream and one or more additional high-value product streams. Within the constraint of complete utilization of carbon and hydrogen produced in the process, the amount of saturated hydrocarbon fuel or fuel additive and the selection and amount of other high-value product streams can be adjusted to meet variations in market demand and market value for different product streams.

Production of Alcohols

The processes of the present invention for making renewable compositions, as described herein, typically begin with the formation of renewable alcohols (e.g., renewable ethanol and renewable isobutanol), e.g., from biomass. The term "formation from biomass" includes any combination of methods including fermentation, thermochemical (e.g., Fischer-Tropsch), photosynthesis, etc. Renewable alcohol (e.g., ethanol and isobutanol) streams can be prepared from biomass, by the same method, or by different methods, or portions of the ethanol and/or isobutanol can be prepared by a combination of different methods. A range of renewable alcohols, e.g., ethanol, 1-butanol, 2-butanol, isobutanol, tert-butanol, pentanols, etc. (and the corresponding renewable olefins or other chemicals) may be produced and employed in the integrated processes described herein, When renewable ethanol and renewable isobutanol are formed by fermentation, the feedstock for the fermentation process can be any suitable fermentable feedstock known in the art, for example sugars derived from agricultural crops such as sugarcane, corn, etc. Alternatively, the fermentable feedstock can be prepared by the hydrolysis of biomass, for example lignocellulosic biomass (e.g. wood, corn stover, switchgrass, herbiage plants, ocean biomass, etc.). The lignocellulosic biomass can be converted to fermentable sugars by various processes known in the art, for example acid hydrolysis, alkaline hydrolysis, enzymatic hydrolysis, or combinations thereof. In such processes, the carbohydrate component of the biomass (e.g. cellulose and hemicellulose) are broken down by hydrolysis to their constituent sugars, which can then be fermented by suitable microorganisms as described herein to provide ethanol or isobutanol.

Typically, woody plants comprise about 40-50% cellulose, 20-30% hemicellulose, and 20-28% lignin, with minor amounts of minerals and other organic extractives. The cellulose component is a polysaccharide comprising glucose monomers coupled with $\beta$-1,4-glycoside linkages. The hemicellulose component is also a polysaccharide, but comprising various five-carbon sugars (usually xylose and arabinose), six-carbon sugars (galactose, glucose, and mannose), and 4-O-methyl glucuronic acid and galacturonic acid residues. The cellulose and hemicellulose components are hydrolyzed to fermentable five- and six-carbon sugars which can then be used as a feedstock for the fermentation as described herein. Residual carbon compounds, lignin (a highly branched polyphenolic substance), and organic extractives (e.g., waxes, oils, alkaloids, proteins, resins, terpenes, etc.) can be separated from the sugars at various stages of the hydrolysis process and utilized in various ways, for example, burned has a fuel to provide energy/heat for the fermentation process and/or for subsequent processes (e.g., dehydration, oligomerization, dehydrogenation, etc.).

In one embodiment, the ethanol and isobutanol are both formed by one or more fermentation steps as described herein. Any suitable microorganism can be used to prepare renewable ethanol and butanols. Ethanol can be produced by microorganisms known in the art such as *Saccharomyces cerevisiae*. Butanols can be produced, for example, by the microorganisms described in U.S. Patent Publication Nos. 2007/0092957, 2008/0138870, 2008/0182308, 2007/0259410, 2007/0292927, 2007/0259411, 2008/0124774, 2008/0261230, 2009/0226991, 2009/0226990, 2009/0171129, 2009/0215137, 2009/0155869, 2009/0155869, 2008/02745425, etc. Additionally, butanols and other higher alcohols are produced by yeasts during the fermentation of sugars into ethanol. These fusel alcohols are known in the art of industrial fermentations for the production of beer and wine and have been studied extensively for their effect on the taste and stability of these products. Recently, production of fusel alcohols using engineered microorganisms has been reported (U.S. Patent Application No. 2007/0092957, and *Nature* 2008 (451) 86-89).

Renewable ethanol and renewable isobutanol prepared by fermentation are, in most embodiments, produced in fermentors and/or under conditions optimal for fermentation of the respective alcohol. That is, renewable ethanol is produced in one or more fermentors optimized for production of ethanol and operated under conditions optimized for the production of ethanol (e.g., using microorganisms which produce high yields of ethanol, a fermentable feedstock with suitable nutrients optimal for ethanol-producing microorganisms, temperature conditions and ethanol recovery unit operations optimized for ethanol production, etc.). Likewise, renewable isobutanol is produced in one or more fermentors under conditions optimized for the production of isobutanol (e.g., using microorganisms which produce high yields of isobutanol, a fermentable feedstock with suitable nutrients optimal for isobutanol-producing microorganisms, temperature conditions and isobutanol recovery unit operations optimized for isobutanol production, etc.). In particular embodiments, ethanol is produced in a conventional ethanol fermentation plant and isobutanol is produced in an ethanol fermentation plant retrofitted for the production of isobutanol, for example as described in US 2009/0171129.

In one embodiment, the retrofitted ethanol plant includes an optional pretreatment unit, multiple fermentation units, and a beer still to produce isobutanol. The isobutanol is produced by optionally pretreating a feedstock (e.g., ground corn) to form fermentable sugars in the pretreatment unit. A suitable microorganism, as described herein, is cultured in a fermentation medium comprising the fermentable sugars in one or more of the fermentation units to produce isobutanol. The isobutanol can be recovered from the fermentation medium as described herein, and as described in US 2009/0171129.

Renewable ethanol and butanols can also be prepared using various other methods such as conversion of biomass by thermochemical methods, for example by gasification of biomass to synthesis gas followed by catalytic conversion of the synthesis gas to alcohols in the presence of a catalyst containing elements such as copper, aluminum, chromium, manganese, iron, cobalt, or other metals and alkali metals such as lithium, sodium, and/or potassium (*Energy and Fuels* 2008 (22) 814-839). The various alcohols, including ethanol and butanols can be separated from the mixture by distillation and used to prepare renewable ethylene or renewable butenes, or compounds derived from renewable ethylene and/or butenes as described herein. Alcohols other than ethanol and isobutanol can be recovered and utilized as feedstocks for other processes, burned as fuel or used as a fuel additive, etc.

Alternatively, renewable ethanol and butanols can be prepared photosynthetically, e.g., using cyanobacteria or algae engineered to produce isobutanol, isopentanol, and/or other alcohols (e.g., *Synechococcus elongatus* PCC7942 and *Synechocystis* PCC6803; see Angermayr et al., *Energy Biotechnology with Cyanobacteria*, Curr Opin Biotech 2009 (20) 257-263; Atsumi and Liao, *Nature Biotechnology* 2009 (27) 1177-1182; and Dexter et al., *Energy Environ. Sci.* 2009 (2), 857-864, and references cited in each of these references). When produced photosynthetically, the "feedstock" for producing the resulting renewable alcohols is light, water and $CO_2$ provided to the photosynthetic organism (e.g., cyanobacteria or algae).

Higher alcohols other than butanols or pentanols produced during fermentation (or other processes as described herein for preparing renewable ethanol and butanols) may be removed from the ethanol or butanol prior to carrying out subsequent unit operations (e.g., dehydration). The separation of these higher alcohols from the butanol(s) (e.g. isobutanol) or pentanol(s) (e.g. 1-pentanol, 2-pentanol, 3-pentanol, branched or cyclic pentanols, etc.) can be effected using known methods such as distillation, extraction, etc. Alternatively, these higher alcohols can remain mixed in the butanol(s) or pentanol(s), and can be removed after subsequent processing. For example, any higher alcohols mixed in with isobutanol can be dehydrated with the isobutanol stream to the corresponding olefins, then separated from the mixed butenes. The determination of whether to remove such higher alcohols prior to dehydration, or to remove the corresponding olefin after dehydration (or the corresponding dehydrogenation byproducts/co-products) generally depends on the relative ease and cost of the respective separations and the relative value of the byproducts/co-products. In some cases, the amounts of such by-products may be low enough that removal is uneconomic and a product olefin stream may be used directly with such minor impurities if a subsequent product is tolerant to such impurities. For example, subsequent the polymerization of a product mixed butene stream (and the specification of a product polymer produced thereby) may be such that minor amounts of, e.g., pentenes or other olefins, may be acceptable, and separation of those minor components may be unnecessary. Alternatively, in certain cases, higher alcohols such as pentanols (e.g., 1-pentanol, 2-pentanol, 3-pentanol, branched or cyclic pentanols, etc.) may be produced in sufficient quantities for use in the present integrated processes. For example, higher alcohols, e.g., linear pentanols in sufficient amounts and subject to subsequent reaction/processing to provide an additional feedstock (e.g., pentenes, pentadienes, etc.) for the present integrated processes. Other higher alcohols may similarly produced, separated, processed, reacted, etc. as desired.

Isolation of Alcohols from Fermentation

When the renewable ethanol and isobutanol are prepared by fermentation, the ethanol can be removed from the fermentor by methods known in the art, for example steam stripping, distillation, pervaporation, etc. (see, e.g., Perry & Chilton, CHEMICAL ENGINEER'S HANDBOOK, 4$^{th}$ Ed.).

Isobutanol can also be removed from the fermentor by various methods, for example fractional distillation, solvent extraction (e.g., with a renewable solvent such as renewable oligomerized hydrocarbons, renewable hydrogenated hydrocarbons, renewable aromatic hydrocarbons, etc. prepared as described herein), gas stripping, adsorption, pervaporation, etc., or by combinations of such methods, prior to dehydration. In certain embodiments, ethanol and butanol are removed from the fermentor in the vapor phase under reduced pressure (e.g., as an azeotrope with water as described in U.S. Pat. Appl. Pub. No. 2009/0171129). In some such embodiments, the fermentor itself is operated under reduced pressure without the application of additional heat (other than that used to provide optimal fermentation conditions for the microorganism) and without the use of distillation equipment, and the produced isobutanol is removed as an aqueous vapor (or azeotrope) from the fermentor. In other such embodiments, the fermentor is operated under approximately atmospheric pressure or slightly elevated pressure (e.g., due to the evolution of gases such as $CO_2$ during fermentation) and a portion of the feedstock containing the isobutanol is continuously recycled through a flash tank operated under reduced pressure, whereby the isobutanol is removed from the headspace of the flash tank as an aqueous vapor or water azeotrope. These latter embodiments have the advantage of providing for separation of the isobutanol without the use of energy intensive or equipment intensive unit operations (e.g., distillation), as well as continuously removing a metabolic by-product of the fermentation, thereby improving the productivity of the fermentation process. The resulting wet isobutanol can be dried and then dehydrated, or dehydrated wet (as described herein), then subsequently dried.

The production of renewable isobutanol by fermentation of carbohydrates typically co-produces small (<5% w/w) amounts of 3-methyl-1-butanol and 2-methyl-1-butanol and much lower levels of other fusel alcohols. One mechanism by which these by-products form is the use of intermediates in hydrophobic amino acid biosynthesis by the isobutanol-producing metabolic pathway that is engineered into the host microorganism. The genes involved with the production of intermediates that are converted to 3-methyl-1-butanol and 2-methyl-1-butanol are known and can be manipulated to control the amount of 3-methyl-1-butanol produced in these fermentations (see, e.g., Connor and Liao, *Appl Environ Microbiol* 2008 (74) 5769). Removal of these genes can decrease 3-methyl-1-butanol and/or 2-methyl-1-butanol production to negligible amounts, while overexpression of these genes can be tuned to produce any amount of 3-methyl-1-butanol in a typical fermentation. Alternatively, the thermochemical conversion of biomass to mixed alcohols produces both isobutanol and these pentanols. Accordingly, when biomass is converted thermochemically, the relative amounts of these alcohols can be adjusted using specific catalysts and/or reaction conditions (e.g., temperature, pressure, etc.).

Dehydration to Ethylene and Butenes

Renewable ethanol and butanols obtained by biochemical or thermochemical production routes as described herein can be converted into their corresponding olefins by reacting the alcohols over a dehydration catalyst under appropriate conditions (see e.g. FIG. 1). Typical dehydration catalysts that convert alcohols such as ethanol and isobutanol into ethylene and butene(s) include various acid treated and untreated alumina (e.g., γ-alumina) and silica catalysts and clays including zeolites (e.g., β-type zeolites, ZSM-5 or Y-type zeolites, fluoride-treated β-zeolite catalysts, fluoride-treated clay catalysts, etc.), sulfonic acid resins (e.g., sulfonated styrenic resins such as Amberlyst® 15), strong acids such as phosphoric acid and sulfuric acid, Lewis acids such boron trifluoride and aluminum trichloride, and many different types of metal salts including metal oxides (e.g., zirconium oxide or titanium dioxide) and metal chlorides (e.g., Latshaw BE, Dehydration of Isobutanol to Isobutylene in a Slurry Reactor, Department of Energy Topical Report, February 1994).

Figure 2:
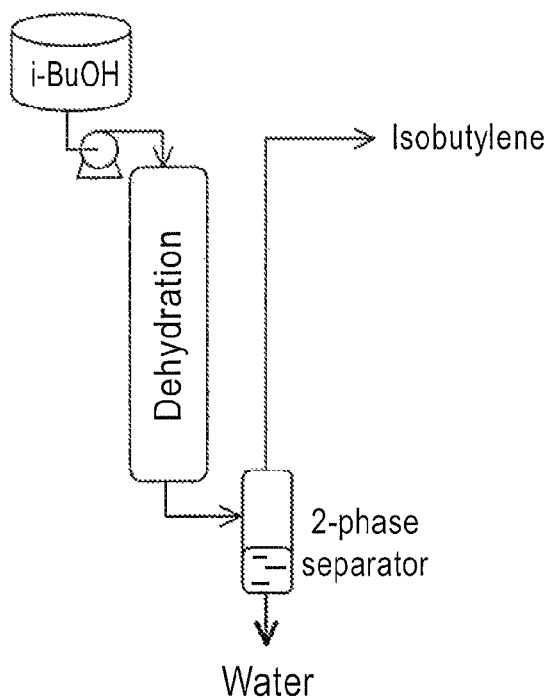
FIG. 2 is a schematic of a unit operation for dehydrating isobutanol to isobutene (isobutylene).

Dehydration reactions can be carried out in both gas and liquid phases with both heterogeneous and homogeneous catalyst systems in many different reactor configurations (see, e.g., FIG. 2). Typically, the catalysts used are stable to the water that is generated by the reaction. The water is usually removed from the reaction zone with the product. The resulting alkene(s) either exit the reactor in the gas or liquid phase, depending upon the reactor conditions, and may separated and/or purified downstream or further converted in the reactor to other compounds (e.g., isomers, dimers, trimers, etc.) as described herein. The water generated by the dehydration reaction may exit the reactor with unreacted alcohol and alkene product(s) and may be separated by distillation or phase separation. Because water is generated in large quantities in the dehydration step, the dehydration catalysts used are generally tolerant to water and a process for removing the water from substrate and product may be part of any process that contains a dehydration step. For this reason, it is possible to use wet (e.g., up to about 95% or 98% water by weight) alcohol as a substrate for a dehydration reaction, then remove water introduced with alcohol in the reactor feed stream with the water generated by the dehydration reaction during or after the dehydration reaction (e.g., using a zeolite catalyst such as those described U.S. Pat. Nos. 4,698,452 and 4,873,392). Additionally, neutral alumina and zeolites can dehydrate alcohols to alkenes but generally at higher temperatures and pressures than the acidic versions of these catalysts. In certain embodiments, the alkene(s) produced in the dehydration reaction are isolated after the dehydration step, before being used as feedstocks for subsequent process steps (e.g., oligomerization, dehydrogenation, disproportionation, etc.). Depending on the particular configuration of the process, isolation of the alkenes after formation in the dehydration reactor can offer certain advantages, for example when the dehydration is carried out in the gas phase, while subsequent process steps are carried out in the liquid phase. However, in certain other embodiments of the process of the present invention, the alkenes can be used directly from the product stream of the dehydration reactor, without isolation (e.g., when the dehydration and the subsequent process steps are carried out under similar temperature and pressure conditions and/or when such subsequent steps are relatively insensitive to water).

Renewable ethylene may be produced directly by the dehydration of renewable ethanol. However, when 1-butanol, 2-butanol, or isobutanol are dehydrated, a mixture of four $C_4$ olefins—1-butene, cis-2-butene, trans-2-butene, and isobutene—can be formed. The exact concentration in a product stream of each butene isomer is determined by the thermodynamics of formation of each isomer. Accordingly, the reaction conditions and catalysts used can be manipulated to affect the distribution of butene isomers in the product stream. Thus, one can obtain butene mixtures enriched in a particular isomer. However, production of a single butene isomer by dehydration is generally difficult. For example, dehydration of isobutanol at 280° C. over a γ-alumina catalyst can be optimized to produce up to 97% isobutene despite an expected equilibrium concentration of ~57% at that temperature (see FIG. 3). However, there is currently no known method for cleanly dehydrating isobutanol to 99+% isobutene (Saad L and Riad M, *J Serbian Chem Soc* 2008 (73) 997).

The dehydration conditions for isobutanol can be varied in the process of the present invention to provide different butene isomer compositions suitable for producing a desired product mixture. For example, if it is desirable to increase the level of propylene produced by the present process (e.g., by disproportionation of ethylene and 2-butene, as described herein), isobutanol dehydration reaction conditions can be adjusted (e.g., reactor temperature, pressure, residence time, catalyst identity, etc.) to increase the relative amounts of 2-butene in the dehydration product stream.

Alternatively, the dehydration reaction can be combined in various ways with an isomerization reaction (using suitable catalysts and conditions as described herein) to effectively achieve a desired butene isomer distribution. For example, if increased amounts of 2-butene are desired, the 1-butene and isobutene isomers can be recycled one or more times at various stages in the process (e.g., after dehydration of isobutanol, and/or after any other unit operations utilizing a feedstock containing 1-butene or isobutene) to an isomerization reaction to produce additional 2-butene, thereby effectively increasing the amount of 2-butene produced.

Propylene by Metathesis

Propylene is conventionally produced by cracking higher hydrocarbons, and as a byproduct in other processes in petroleum refineries. Renewable propylene could be produced by dehydration of renewable propanols such as isopropanol or n-propanol (e.g. derived from renewable acetone provided by so-called "ABE" fermentation processes, or from propanol produced from biomass by thermochemical processes), but such "ABE" processes are generally relatively inefficient, and the resulting renewable propanol is accordingly not cost competitive with petrochemically derived propanol (e.g., produced by hydroformylation of petroleum derived ethylene). However, renewable propylene can be more efficiently produced by the disproportionation of renewable ethylene and renewable 2-butene. As described herein, ethylene can be readily prepared by dehydration of ethanol, and 2-butene can be prepared by the dehydration of isobutanol under suitable conditions, and/or by the isomerization of renewable isobutene or 1-butene produced by the dehydration of isobutanol.

The specific unit operations employed in the preparation of renewable propylene will depend on the nature of the starting materials and desired ultimate products. For example, renewable propylene can be prepared by separately dehydrating ethanol and butanol, followed by disproportionation of at least a portion of the ethylene and butene(s) produced as described herein (e.g., the remaining portion of the ethylene and butene(s) used in other unit operations), or by the dehydration of mixtures of isobutanol and ethanol to a mixture of ethylene and butylenes, at least a portion of which is then disproportionated in the presence of the appropriate metathesis catalyst to provide propylene. Since dehydration of isobutanol typically produces a mixture of butene isomers, and optimal conditions for dehydrating isobutanol and ethanol are typically somewhat different, in various embodiments the dehydration of isobutanol and ethanol are carried out separately (e.g., in separate dehydration reactors, or at different times in the same dehydration reactor). In particular embodiments, the dehydration of isobutanol and ethanol are carried out in one or more separate isobutanol dehydration reactors and one or more separate ethanol dehydration reactors, and the resulting ethylene and 2-butene are then reacted in one or more metathesis reactors in the presence of an appropriate metathesis catalyst.

Depending upon the specific mixture of butenes formed after dehydration of isobutanol, and the value of particular intermediates or products, a portion of the various butenes can be subjected to various additional unit operations. For example, a portion of the unreacted isobutene can be isomerized to linear butenes (1- and 2-butenes) and the linear butenes (particularly 2-butenes) can be recycled back to the disproportionation step, or the isobutene can be converted to, e.g., tort-butyl ethers or ten-butanol by reaction with alcohols or water, oligomerized and hydrogenated to higher alkanes/alkenes suitable for use in fuels (e.g., isooctane/isooctene), dehydrocyclized to aromatics (e.g., xylenes such as o-xylene, p-xylene or m-xylene), etc. The isomerization of isobutene can be carried out in a separate isomerization step (e.g., in a separate isomerization reactor), or can occur in-situ during the disproportionation reaction by appropriate selection of catalyst in the metathesis reactor.

In some embodiments, renewable propylene is prepared using a method similar to that described in U.S. Pat. No. 7,214,841, in which renewable butenes (e.g., a mixture comprising 1-butene, 2-butenes, and/or isobutene) and renewable ethylene, prepared as described herein, are reacted in the presence of a metathesis catalyst. Since isobutene may also react with renewable 1- or 2-butenes in the presence of a metathesis catalyst (producing, e.g., mixed pentenes and hexenes), in various embodiments isobutene is removed from the butene mixture prior to the metathesis step to minimize formation of pentenes and hexenes. However, pentenes and hexenes are easily separated from ethylene and propylene, and can be used as chemical intermediates for further unit operations in the process of the present invention, or as fuel blend stocks, etc. Accordingly, in some embodiments the isobutene is not removed from the metathesis reaction feedstock, and the resulting pentenes and hexenes are subsequently removed and utilized as described herein, while ethylene can be recycled to the metathesis reaction as feedstock (and the propylene can be recovered). Any isobutene remaining in the metathesis product mixture can be removed and recycled to a separate rearrangement step (e.g., to produce linear butenes) or diverted to other processes (e.g., oligomerization, oxidation, etc. to produce biofuels, acrylates, aromatics, etc.) as described herein.

In various embodiments, renewable propylene is formed by reacting an approximately 1.3:1 molar mixture of renewable ethylene and renewable 2-butene in a metathesis reactor in the presence of a suitable metathesis catalyst as described herein. The approximately 1.3:1 molar mixture of renewable ethylene and renewable 2-butene can be formed by mixing a suitable portion of the renewable ethylene formed by dehydration of renewable ethanol and a portion of the renewable 2-butene isolated from the mixture of butene isomers formed by dehydration of renewable isobutanol. The renewable 2-butene can be obtained by separation from the mixture of butene isomers formed after dehydration of isobutanol, using suitable methods such as fractional distillation, absorption, etc. In other embodiments, the molar ratio of renewable ethylene and renewable 2-butene can be adjusted depending on the composition of the metathesis feedstock stream(s) and/or the metathesis reaction conditions (e.g., temperature, pressure, residence time, etc.) to maximize production of a desired metathesis product (e.g., propylene) or to adjust the composition of the product stream for subsequent unit operations. For example, when the feedstock comprises a mixture of propylene, isobutene, and linear butenes, it may be desirable to increase the molar ratio of 2-butenes in the feedstock to compensate for side-reactions which can reduce the amount of 2-butenes available for reaction with ethylene (e.g., to maximize propylene production). Alternatively, if metathesis conditions (e.g., addition of an isomerization catalyst such as magnesium oxide) are selected which promote isomerization of 1-butenes and/or isobutene to 2-butenes in the metathesis reactor, the feedstock can comprise lower levels of 2-butenes, so that optimal levels of 2-butenes are provided by 2-butene initially present in the feedstock and 2-butenes produced in-situ in the metathesis reaction by isomerization of isobutene and/or 1-butene.

In still other embodiments, the mixed butenes can be oligomerized over an acidic ion exchange resin under conditions which selectively convert isobutene to isooctene (e.g., using the methods of Kamath et al., *Ind Engr Chem Res* 2006 (45) 1575-1582), but leave the linear butenes substantially unreacted, thereby providing a substantially isobutene-free mixture of linear butenes (e.g., containing less than about 10%, 5%, 4%, 3%, 2%, 1% of isobutene, or any other value or range of values therein or therebelow). After separation of isooctene from the mixed linear butenes, the substantially isobutene-free renewable linear butenes can then be combined with renewable ethylene and reacted in the presence of a metathesis catalyst to form renewable propylene.

The disproportionation/metathesis of ethylene and linear butenes (e.g., 1- and/or 2-butene) can be carried out in the presence of one or more suitable metathesis catalysts, optionally including one or more components which may catalyze the rearrangement of isobutene to linear butenes (particularly 2-butenes) as described herein. A non-limiting list of suitable metathesis catalysts include, for example, oxides, hydroxides, or sulfides of metals such as tungsten, molybdenum, rhenium, niobium, tantalum, vanadium, ruthenium, rhodium, iridium, iron, potassium, chromium, and osmium. These metal oxides/hydroxides/sulfides can be supported on a high surface-area (e.g., 10 m$^2$/g or more) inorganic carrier known in the catalyst art, such as silica, γ-alumina, titania, etc. The metathesis catalyst can also contain a promoter compound to increase catalyst activity and/or specificity, such as lithium, sodium, potassium, cesium, magnesium, calcium, strontium, barium, zinc, yttrium compounds (e.g., elemental forms as well as oxides, hydroxides, nitrates, acetates, etc., as described in Banks R L and Kukes S G, *J Molec Cat* 1985 (28) 117-1311; U.S. Pat. Pub. No. 2008/0312485; and U.S. Pat. Nos. 4,575,575, and 4,754,098), or an inorganic compound containing a promoter, such as hydrotalcite, or in particular embodiments, tungsten oxide on silica and magnesium oxide (e.g., as described in U.S. Pat. No. 7,214,841). In other embodiments, the renewable linear butenes (produced as described herein by the dehydration of renewable isobutanol) are reacted with renewable ethylene in the presence of a catalyst comprising rhenium oxide on alumina.

Suitable metathesis reaction conditions include those described in U.S. Pat. No. 3,261,879: temperatures ranging from about 250° F. to about 550° F., pressures ranging from about 0-1500 psig, WHSV values ranging from about 0.5 to 20 hr$^{-1}$, a minimum 30% molar excess ethylene (e.g., moles ethylene at least about 1.3 times moles butenes). Alternatively, suitable metathesis conditions include those described in U.S. Pat. Appl. Pub. No. 2008/0312485: a catalyst comprising a mixture of tungsten oxide on silica and hydrotalcite, reaction temperature of about 200° C., and a reaction pressure of about 3.5 MPa.

In most embodiments, the renewable butenes and ethylene in the metathesis feedstock are purified to remove impurities which may "poison" the metathesis catalyst. For example, purification may include removing water; oxygenates such as carbon dioxide, alcohols, aldehydes, acids, etc.; nitrogen or nitrogen-containing compounds; sulfur-containing compounds such as hydrogen sulfide, ethyl sulfide, diethyl sulfide, methyl ethylsulfide; alkynes such as acetylene and methylacetylene; dienes such as butadiene, etc. in some embodiments, purification may include removing isobutene (as described herein). In various embodiments, the levels of such impurities in the metathesis feedstock are maintained below about 10 ppm, in most embodiments less than 1 ppm. Purification can be carried out using conventional methods, for example the methods described in U.S. Pat. Nos. 3,261,875 and 7,214,841, or U.S. Pat. Appl. Pub. No. 2008/0312485, in which the metathesis feedstock is passed over an absorbent bed comprising alumina, zeolites, magnesium and other metal oxides. In most embodiments, a "poisoned" metathesis catalyst can be regenerated in air at about >1000° F. In particular embodiments the metathesis catalyst is periodically regenerated by heating the catalyst in the presence of oxygen (e.g., air) as described herein. For example, the process of the present invention can employ two or more metathesis reactors such that at least one of the metathesis reactors can be regenerated while the other metathesis reactors are in operation, thereby permitting continuous operation of the process.

Isobutene and Linear Butenes

As described herein, the dehydration of isobutanol typically provides a mixture of butene isomers, including isobutene and linear butenes. Depending upon the dehydration conditions used, the mixture of butenes in an isobutanol dehydration product stream can contain varying amounts of isobutene. For example, if the dehydration is carried out at lower temperatures, typically a higher percentage of the butene product stream comprises isobutene (see FIG. 3). Accordingly, if higher levels of isobutene production are desirable (e.g., for the production of polyisobutylene, butyl rubber, other butene copolymers, xylenes, etc.), the process conditions of the isobutanol dehydration can be adjusted to increase the percentage of isobutene produced in the isobutanol dehydration product stream. The remaining linear butenes can be isomerized (e.g., in a separate isomerization reactor) to form additional isobutene, which can then be combined with the isobutene produced from dehydration, or diverted to other processes, e.g., oligomerization, dehydrogenation, dehydrocyclization, isomerized to linear butenes for disproportionation with ethylene to form propylene, etc.

Alternatively, if higher levels of linear butenes are desirable (e.g., for disproportionation with ethylene to form propylene, dehydrogenation to form butadiene, etc.), the isobutanol dehydration process conditions can be adjusted to increase the proportion of linear butenes formed (e.g., by increasing the dehydration process temperature), and the isobutene can be separated from the isobutanol dehydration product stream and isomerized (e.g., in a separate isomerization reactor) to form additional linear butenes, which can be combined with the initially formed linear butenes. Alternatively, if the desired product is butadiene, the mixture of linear butenes and isobutene can be dehydrogenated to form a mixture of isobutene and butadiene. Since isobutene is substantially unreactive to dehydrogenation conditions for forming butadiene from linear butenes, the isobutene remains unreacted in the product stream, and can be readily separated from the butadiene. The unreacted isobutene can then be recycled and isomerized to form additional linear butenes, or diverted to other process steps.

Butadiene

Di-olefins (dienes) such as butadiene are conventionally produced in petrochemical refineries by the cracking reactions that generate $C_4$-containing olefin streams for petrochemical use. If additional di-olefins are required, they can be produced by dehydrogenation of the $C_4$ mono-olefins. For example, butadiene may be produced by passing raffinate-2 over a dehydrogenation catalyst.

Figure 4:
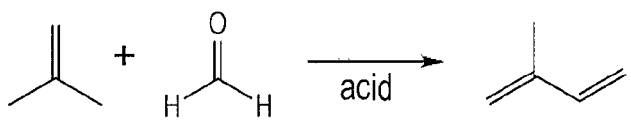
FIG. 4 is a schematic of a method of preparing $C_5$ dienes (e.g., isoprene) from $C_4$ olefins (e.g., isobutene) by the Prins reaction.

Dehydrogenation catalysts convert saturated carbon-carbon bonds in organic molecules into unsaturated double bonds (see FIG. 4). Typical dehydrogenation catalysts include mixtures of metal oxides with varying degrees of selectivity towards specific olefins. For example, in certain oxidative dehydrogenations, iron-zinc oxide mixtures favor 1-butene dehydrogenation while cobalt-iron-bismuth-molybdenum oxide mixtures favor 2-butene dehydrogenation (see, e.g., lung et al., *Catalysis Letters* 2008 (123), 239). Other examples of dehydrogenation catalysts include vanadium- and chrome-containing catalysts (see, e.g., Toledo-Antonio et al., *Applied Catalysis A* 2002 (234) 137), ferrite-type catalysts (see, e.g., Lopez Nieto et al., *J Catalysis* 2000 (189) 147), manganese-oxide doped molecular sieves (see, e.g., Krishnan V V and Suib S L, *J Catalysis* 1999 (184) 305), copper-molybdenum catalysts (see, e.g., Tiwari et al., *J Catalysis* 1989 (120) 278), and bismuth-molybdenum-based catalysts (see, e.g., Batist et al., *J Catalysis* 1966 (5) 55).

Figure 5:
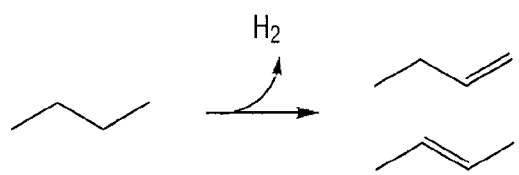
FIG. 5 is a schematic of the dehydrogenation of n-butane.

Dehydrogenation of an olefin to a di- or polyolefin can occur if the olefin molecule can accommodate one or more additional double bonds. For example, 1-butene can be dehydrogenated to butadiene (see FIG. 5). Dehydrogenation catalysts are also capable of rearranging olefinic bonds in a molecule to accommodate a second olefin bond, generally when skeletal rearrangement is not required (e.g., rearrangement by one or more hydrogen shifts), but these catalysts typically do not catalyze skeletal rearrangements (e.g., breaking and reforming C—C bonds) under dehydrogenating conditions. For example, 2-butene can be dehydrogenated to butadiene but isobutene is not typically dehydrogenated to butadiene in the same process unless the reaction conditions/catalysts are selected to both promote skeletal rearrangement and dehydrogenation. Alternatively, one or more process units may be employed, wherein a stream comprising isobutene may be subject to isomerization conditions to promote the formation of linear butenes (e.g., as described herein) to effect skeletal rearrangement, then subsequently subject to dehydrogenation conditions to maximize production of butadiene form a mixed butene stream.

Two major types of dehydrogenation reactions are conventionally used to produce olefins from saturated materials (see, e.g., Buyanov R A, *Kinetics and Catalysis* 2001 (42) 64). A first type, endothermic dehydrogenation, typically uses a dehydrogenation catalyst (e.g., chromia-alumina-based, spinel supported platinum-based, phosphate-based, and iron oxide-based catalysts), high heat (typically 480-700° C.), and a reactor configuration (typically fixed-bed and fluidized-bed reactors) that favors the formation of hydrogen gas to drive the reaction forward, and also employs dilution of the feedstock with gases such as helium, nitrogen, or steam to lower the partial pressure of any hydrogen that is formed in the reaction. Alternatively, the reaction may be conducted under reduced pressure (e.g., from 0.1 to 0.7 atm) to effect reduction of the partial pressure of hydrogen in the reaction, promoting the formation of products. In a second type of hydrogenation, exothermic dehydrogenation, the catalysts typically function in the absence of oxygen, minimizing the formation of oxidized products (e.g., methacrolein and methacrylate, when the feedstock comprises butenes). Oxidative dehydrogenation typically employs mixed metal oxide-based dehydrogenation catalysts (typically containing molybdenum, vanadium, or chromium), lower temperatures (300-500° C.), and a fixed- or fluidized-bed reactor configuration. The process may include the addition of oxygen to the reaction to drive the reaction. Introduced oxygen reacts with produced hydrogen to form water, thus reducing the partial pressure of hydrogen in the reactor and favoring the formation of additional products. Both types of dehydrogenation reactions are applicable to the invention described herein. In some embodiments wherein hydrogen production is desired, endothermic dehydrogenation may be used and reactions conditions may be optimized to maximize hydrogen capture (e.g., for subsequent use in hydrogenation reactions or unit operation as described herein).

The selectivity of dehydrogenation catalysts towards olefins that can accommodate a second olefinic bond can be used to prepare dienes (e.g., butadiene), or alternatively used as a method of purifying the olefin mixture (e.g. by facilitating separation of a diene from unreactive mono-olefins). For example, as described herein, the dehydration of isobutanol typically produces isobutene and both 1- and 2-butenes. Treatment of this product mixture with a dehydrogenation catalyst selectively converts the 1- and 2-butenes—but not isobutene—to butadiene. It is possible that some skeletal rearrangement of the isobutene occurs during the dehydrogenation reaction, but this rearranged material generally is dehydrogenated to form butadiene. After complete dehydrogenation (which may require recycling unreacted butenes back to the dehydrogenation feedstock), the butadiene and unreacted isobutene can be readily separated by extractive distillation of the butadiene, to produce high purity (about 80-100%, e.g., >about 80%, >about 85%, >about 90%, >about 95%, >about 98%, >about 99%, or >about 99.8%) isobutene and butadiene streams suitable e.g. for use as a monomer feedstock for polymerization.

Figure 6:
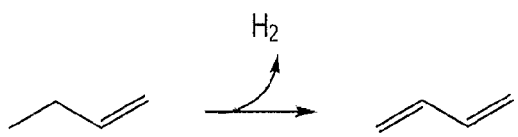
FIG. 6 is a schematic of the dehydrogenation of 1-butene to 1,3-butadiene.

Renewable linear butenes are readily dehydrogenated to renewable butadiene. Accordingly, in the process of the present invention, a portion of the linear butenes produced by dehydration of renewable isobutene can be dehydrogenated to 1,3-butadiene. Under typical linear butene dehydrogenation conditions, isobutene is relatively inert. Accordingly, in various embodiments of the process, butadiene can be produced by dehydrogenation of mixtures of butenes containing both linear butenes and isobutene. In some embodiments, it may be desirable to remove isobutene from the dehydration product/dehydrogenation feedstock prior to the dehydration reaction (e.g., such that the dehydration feedstock contains essentially only linear butenes). When a mixture of linear butenes and isobutene is dehydrogenated, the dehydrogenation product stream comprises butadiene, unreacted isobutene, and optionally unreacted linear butenes (e.g., produced under low conversion conditions). In some embodiments, at least a portion of the unreacted linear butenes can be recycled back to the dehydrogenation reactor to further convert linear butenes to butadiene (thereby increasing the overall yield of butadiene), and/or a portion of the unreacted linear butenes can be reacted with at least a portion of the ethylene to form propylene (as described herein). The unreacted isobutene can be separated from butadiene, and at least a portion of the unreacted isobutene can be recycled to a separate isomerization step (e.g., producing linear butenes as shown in FIG. 6) or portions of the unreacted isobutene can be diverted to other processes (e.g., oligomerization, oxidation, etc. to produce biofuels, acrylates, aromatics, etc.) as described herein. If the unreacted isobutene is isomerized to linear butenes, at least a portion of these linear butenes can be recycled back to a dehydrogenation step to produce additional butadiene, or alternatively diverted to other processes such as disproportionation with ethylene to produce additional propylene, alkylation of aromatics, etc.

In still other embodiments, the mixed butenes can be oligomerized over an acidic ion exchange resin under conditions which selectively convert isobutene to isooctene (e.g. using the methods of Kamath R S et al, Industrial Engineering and Chemistry Research 2006, 45, 1575-1582), but leave the linear butenes essentially unreacted, thereby providing a substantially isobutene-free mixture of linear butenes (containing e.g., less than about 1% isobutene, or less than about 0.9%, less than about 0.8%, less than about 0.7%, less than about 0.6%, less than about 0.5%, less than about 0.4%, less than about 0.3%, less than about 0.2%, or less than about 0.1%, including ranges and subranges thereof). Some or all of the essentially isobutene-free renewable linear butenes can then be reacted in the presence of a dehydrogenation catalyst to form renewable butadiene. In still other embodiments, isobutene can be removed from a mixed butene stream by, e.g., selective oxidation of isobutene in the mixed stream to form, e.g., tert-butanol and/or methyl tert-butyl ether.

Figure 3:
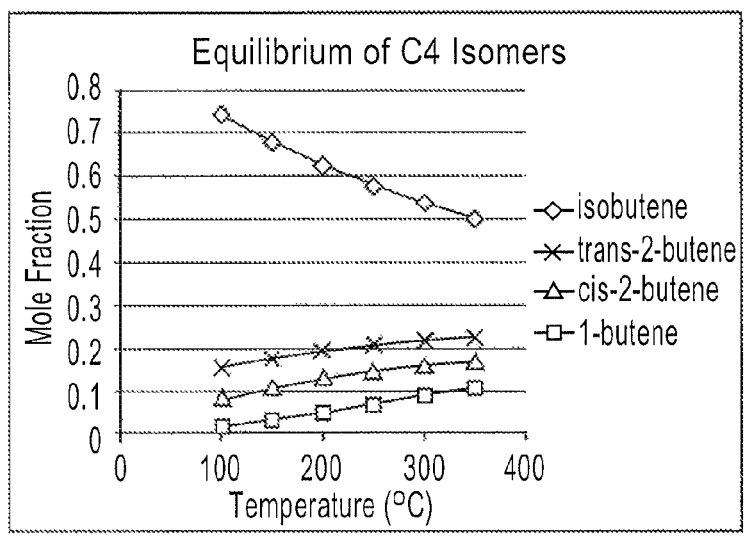
FIG. 3 is a plot of butene isomer equilibrium composition as a function of dehydration temperature.

In another embodiment, the amount of 1- and 2-butenes produced in the dehydration of isobutanol can be increased up to the equilibrium amount accessible at the reaction temperature (see, e.g., FIG. 3). For example, in some embodiments, dehydration catalysts are selected such that at 350° C., the dehydration of isobutanol produces a mixture comprising about 50% isobutene and about 50% of 1- and 2-butenes. At least a portion of the resulting mixture can be treated with a dehydrogenation catalyst to produce butadiene from isobutanol at up to about 50% yield.

In various embodiments the isobutene can be removed from the mixture of linear butenes prior to dehydrogenation, or alternatively, if the dehydrogenation conditions and catalyst are selected to minimize any undesired side reactions of the isobutene, the isobutene can removed from the product stream after the dehydrogenation reaction step. In other embodiments, a portion or all of the isobutene can be diverted to form other valuable hydrocarbons (e.g., oligomerized to form isooctenes/isooctanes for biofuels, dehydrocyclized to form aromatics for fuels, phthalates, etc.). The isobutene can also be rearranged to linear butenes (1- and 2-butenes), which can then be recycled back to the dehydrogenation reaction step to form additional butadiene, thereby increasing the effective yield of butadiene to above 50% relative to feed isobutanol. If all of the isobutene is recycled, the effective yield of butadiene in various processes of the present invention can approach about 100%. However, as some cracking and "coking" may occur during the dehydrogenation, butadiene yields for the process of the present invention can be about 90% or more (e.g., about 95% or more, or about 98% or more, or any other value or range of values therein or thereabove). The rearrangement of isobutene can be carried out in a separate isomerization step (e.g., in a separate isomerization reactor) after removing the butadiene from the dehydrogenation product, or can be carried out in-situ during the dehydrogenation reaction by appropriate selection of catalyst (or by use of a suitable catalyst mixture) in the dehydrogenation reactor. For example, dehydration catalysts can be selected which also catalyze rearrangement of isobutene to linear isobutenes, or the dehydration catalyst can be mixed with an isomerization catalyst. A few representative acid catalysts suitable for rearranging isobutene include zeolites such as CBV-3020, ZSM-5, β Zeolite CP 814C, ZSM-5 CBV 8014, ZSM-5 CBV 5524 G, and YCBV 870; fluorinated alumina; acid-treated silica; acid-treated silica-alumina; acid-treated titania; acid-treated zirconia; heteropolyacids supported on zirconia, titania, alumina, silica; and combinations thereof.

In particular embodiments, the isobutene is substantially removed from the product stream after the dehydration reaction step in order to provide a feed stream for the dehydrogenation reaction step which is substantially free of isobutene (e.g., the butene component of the dehydrogenation feed stream comprises substantially only linear butenes). By "substantially removed" we mean that isobutene has been removed from the indicated feed or product stream such that after removal, the isobutene in the feed or product stream comprises less than about 5% (e.g., less than about 4%, less than about 3%, less than about 2%, or less than about 1%, or any other value or range of values therein or therebelow) of the butenes in the indicated feed or product stream. By "substantially only" in reference to the composition of the dehydrogenation feed stream, we mean that the linear butenes comprise at least about 95% (e.g., at least about 96%, at least about 97%, at least about 98%, at least about 99%, or any other value or range of values therein or thereabove) of the butenes in the dehydrogenation feed stream.

In one embodiment, renewable butadiene may be prepared from renewable isobutanol produced by fermentation as described herein. The isobutanol thus produced is then dehydrated under conditions (as described herein) to maximize the yield of linear butenes (e.g., heterogeneous acidic catalysts such as γ-alumina at about 350° C.). The resulting mixture of ~1:1 linear butenes/isobutene is then contacted with a dehydrogenation catalyst (e.g., chromium-oxide treated alumina, platinum- and tin-containing zeolites and alumina, cobalt- and molybdenum-containing alumina, etc. at about 450-600° C.) to form a mixture of butadiene and unreacted isobutene. In a specific embodiment, the dehydrocyclization catalyst is a commercial catalyst comprising chromium oxide on an alumina support. The remaining isobutene can then be isomerized to linear butenes as described herein, and recycled for dehydrogenation in order to produce additional butadiene (thereby increasing the effective yield of butadiene), or used as a raw material for other processes or materials as described herein.

Higher Olefins $C_5$ and higher molecular weight olefins can also be prepared by the process of the present invention from renewable isobutanol and/or renewable ethanol by various methods, using a variety of different reactions used individually or in combination. For example, renewable butenes can be converted to renewable $C_5$ olefins by, for example by hydroformylation by reacting renewable butenes (e.g., renewable isobutene) with formaldehyde (which can be renewable formaldehyde, e.g., prepared from methanol produced from biomass by thermochemical processes) or CO and $H_2$, in the presence of an acidic catalyst (e.g., via the Prins reaction, see FIG. 6). Renewable pentenes, hexenes and higher molecular weight olefins and can also be prepared as co-products from the metathesis of ethylene and butene mixtures as described herein (e.g., by the disproportionation of isobutene and 1-butene to form ethylene and methylpentene(s), the disproportionation of 2 equivalents of isobutene to form dimethylbutene(s), etc.). By varying the relative amounts of ethylene and the various butene isomers fed to the metathesis reaction and the metathesis reaction conditions (e.g., temperature, pressure, catalyst, residence time, etc., the metathesis product stream can be accordingly adjusted to provide desired amounts of ethylene, propylene, butenes, and $C_5$ and higher olefins. In particular, higher concentrations of isobutene and/or 1-butene in the metathesis feedstock would favor higher levels of $C_5$ and higher molecular weight olefins.

Renewable $C_5$ olefins (e.g., isopentene, 3-methyl-1-butene and 2-methyl-2-butene, etc.) can then be converted to, e.g., isoprene using a dehydrogenation catalyst, under conditions similar to those used to convert butenes to butadiene as described above.

Alternatively, or in addition to the processes for preparing olefins described herein, higher molecular weight olefins can be prepared by oligomerization of lower molecular weight olefins. The term "oligomerization" or "oligomerizing" refer to processes in which activated olefins are combined with the assistance of a catalyst to form larger molecules called oligomers. Oligomerization refers to the combination of identical olefins with one another (e.g., ethylene, isobutene, propylene, pentenes, hexenes, etc.) as well as coupling of different alkenes (e.g., isobutene and propylene), or the combination of an unsaturated oligomer with an olefin. For example, isobutene can be oligomerized by an acidic catalyst to form eight-carbon oligomers (dimers) such as isooctene (e.g., trimethylpent-1-enes and trimethylpent-2-enes) and/or twelve-carbon oligomers (trimers) such as 2,2,4,6,6-pentamethylhept-3-ene, 2,4,4,6,6-pentamethylhept-1-ene. Similarly, oligomers of other monomers can produce higher molecular weight oligomers. In other embodiments, controlled oligomerization of propylene can produce dimers (e.g., hexenes), trimers (e.g., nonenes), etc. Similarly, pentenes, hexenes, or other monomers may be combined in a controlled fashion to provide oligomers having a desired number of carbon atoms. Furthermore, mixed cross-coupling or oligomerization is also possible. For example, propylene and butenes may be oligomerized to provide, e.g., heptenes, decenes, etc.

Heterogeneous or homogenous oligomerization catalysts can be used in the process of the present invention (see, e.g., G. Busca, "Acid Catalysts in Industrial Hydrocarbon Chemistry" *Chem Rev* 2007 (107) 5366-5410. Of the many methods for oligomerizing alkenes, the most relevant processes for the production of fuels and fine chemicals generally employ acidic solid phase catalysts such as alumina and zeolites (see, e.g., U.S. Pat. Nos. 3,997,621; 4,663,406; 4,612,406; 4,864,068; and 5,962,604).

Various methods can be used for controlling the molecular weight distribution of the resulting oligomers, including methods which form primarily dimers including isooctene (see, e.g., U.S. Pat. No. 6,689,927), trimers (see, e.g., PCT Pat. Appl. Pub. No. WO 2007/091862), and tetramers and pentamers (see, e.g., U.S. Pat. No. 6,239,321). Typical methods for controlling oligomer molecular weight include the addition of alcohols such as t-butanol and diluents such as paraffins. Additionally, higher molecular weight oligomers and polymers can be formed using similar catalysts reacting under different conditions. For example, low molecular weight polyisobutylene (up to 20,000 Daltons) can be produced using a boron trifluoride complex catalyst (see, e.g. U.S. Pat. No. 5,962,604).

If a mixture of different olefins produced in any of the processes described herein is oligomerized, the resulting oligomer mixture comprises the corresponding addition products formed by the addition of two or more olefins, which can be the same or different. For example if a mixture of propene and butenes is oligomerized, the product can comprise "binary" or "dimer" addition products such as hexenes, heptenes, octenes; "ternary" or "trimer" addition products such as nonenes, decenes, undecenes, dodecenes, etc.

The renewable unsaturated aliphatic compounds prepared by oligomerization in the process of the present invention generally have, on average, one carbon-carbon double bond per molecule. However, by selecting appropriate reaction conditions (e.g., catalyst identity, residence time, temperature, pressure, etc.), the oligomers formed can have two or more carbon-carbon double bonds, e.g., via dehydrodimerization. On average, the product of the oligomerizing step of the process of the present invention has less than about two double bonds per molecule. In some embodiments, the product oligomer has less than about 1.5 double bonds per molecule. In most embodiments, the unsaturated aliphatic compounds (alkenes) have on average one double bond. Any of the olefins produced by the process of the present invention can be converted to other compounds, for example hydrogenated to form the corresponding saturated hydrocarbons, oxidized to the corresponding alcohol, aldehyde, carboxylic acid, homologated with heteroatoms, etc. using methods known in the art for transforming carbon-carbon double bonds to other functional groups.

The term "oligomerization" can also include reactions of olefins with aromatic hydrocarbons in the presence of an oligomerization catalyst (also termed "alkylation"). Catalysts specifically intended or optimized for the alkylation of aromatics are also termed alkylation or alkylating catalysts, and catalysts specifically intended or optimized for oligomerization of alkenes are termed oligomerization catalysts. Oligomerization and alkylation can, in some embodiments, be carried out simultaneously in the presence of a single catalyst capable of catalyzing both reactions, or in other embodiments, can be carried out as separate reactions using separate oligomerization and alkylation catalysts. For example, benzene can be reacted with isobutylene in the presence of an oligomerization catalyst as described herein to form t-butylbenzene or di-t-butylbenzenes. Similarly, toluene can be reacted in the presence of an oligomerization catalyst and isobutylene to form t-butylmethylbenzenes, etc.

The alkylation of aromatics can be carried out using industrially available catalysts such as mineral acids (e.g., phosphoric acid) and Friedel-Crafts catalysts (e.g., $AlCl_3$-HCl), for example, to alkylate renewable benzene (prepared as described herein) with renewable ethylene or renewable propylene to produce renewable ethyl benzene and cumene, respectively. Renewable ethyl benzene and cumene can then be used as starting materials for the production of renewable phenol and renewable styrene, e.g., using the methods described in *Catalysis Review* 2002, (44) 375. Alternatively, solid acid catalysts such as zeolite-based catalysts can be used to catalyze the direct alkylation of renewable benzene with renewable propylene or ethylene.

For more highly reactive olefins (reactivity typically increases with increasing length of the olefin chain) oligomerization of the olefin can compete with alkylation of the aromatic, and thus in some embodiments, high aromatic to olefin ratios may be used to minimize formation of olefin oligomers (where such oligomers are undesired) and favor production of alkylated aromatics. Renewable benzene, toluene and xylene can be alkylated with renewable propylene or isobutylene to produce heavier aromatic compounds that are suitable for renewable jet fuel (see, e.g., *Ind. Eng. Chem. Res.* 2008 (47) 1828).

Furthermore, since aromatic alkylation conditions are typically similar to oligomerization conditions, both steps can be performed in one reactor or one reaction zone by reacting a stream of renewable aromatics with renewable alkenes in the presence of a suitable catalyst to provide a mixture of olefin oligomers and alkyl aromatics suitable for use in transportation fuels (e.g., "Jet A" type fuel). Under excess olefin conditions (e.g., low aromatic/olefin ratios), both aromatic alkylation and oligomerization will take place. Alternatively, it is well known that alcohols can also act as alkylating agents under acid catalytic conditions. Accordingly, in other embodiments, aromatics can be alkylated with renewable ethanol or renewable isobutanol under excess alcohol conditions (e.g., dehydration of the alcohol and subsequent oligomerization occur in the presence of aromatics, resulting in alkylation of aromatics). In still other embodiments, oligomerization/aromatic alkylation with propylene or butenes and one or more aromatics can be carried in the presence of an acid catalyst in one reaction zone or in one reactor having two or more reaction zones. In particular embodiments, ethanol or isobutanol can be used as alkylating agents for aromatics in the presence of an acid catalyst in one reaction zone.

Aromatics

Renewable aromatic compounds can be produced from renewable alcohols and olefins, for example, using the methods described in U.S. Pat. Nos. 3,830,866, 3,830,866, and 6,600,081. In particular, renewable aromatics can be readily produced from renewable olefins by dehydrocyclization. For example, renewable propylene dimers ($C_6$ olefins) produced as described herein can dehydrocyclized to form renewable benzene. Similarly; renewable butene dimers produced as described herein can be dehydrocyclized to $C_8$ aromatics such as xylenes (particularly p-xylene as described in U.S. Ser. No. 12/899,285) and ethylbenzene. Since olefins are more reactive than the primarily saturated alkanes traditionally used in petroleum refineries to produce aromatics, milder reaction conditions can be used in the processes of the present invention, resulting in improved selectivity for a desired single product (e.g., p-xylene). Alkyl substituted aromatics can alternatively be prepared by alkylation of unsubstituted or substituted aromatics (e.g., benzene or toluene) with low molecular weight olefins (e.g., ethylene) using an appropriate alkylation catalyst.

In the present integrated process(es), the selectivity for p-xylene in an aromatic fraction relative to other aromatic products can be greater than about 90% (e.g., greater than about 95%, greater than about 98%, or any other value or range of values therein or thereabove), using, for example, renewable isooctene as a starting material. The resulting product contains only negligible amounts of renewable benzene and toluene, and predominately comprises xylene(s), from which renewable p-xylene can be recovered at very high purity (e.g., greater than about 90%, greater than about 95%, greater than about 98%, or any other value or range of values therein or thereabove). As previously described herein, appropriate conditions (e.g., catalyst identity, temperature, pressure, residence time, etc.) may be selected to favor formation of, e.g., p-xylene over other xylene isomers.

In alternative embodiments of the process of the present invention, renewable aromatics—benzene, toluene, and xylene (BTX)—may be produced by the dehydrocyclodimerization and dehydration of renewable alkanes, e.g. isobutane, prepared from renewable alcohols, e.g. isobutanol, reacted with a hydrotreating catalyst. The hydrodeoxygenation process can be carried out over, e.g., Co/Mo, Ni/Mo or both catalysts in the presence of hydrogen at moderate temperatures (e.g., ~150° C.). When isobutanol is used as a starting material in this reaction, the reaction may be highly selective (~90%) for isobutane with high (e.g., more than 95%) conversion.

The renewable alkenes, e.g., propylene or isobutylene, formed by the process of the present invention can also be aromatized using various catalysts, for example zeolite catalysts, e.g. H-ZSM-5 (*Ind. Eng. Chem. Process Des. Dev.* 1986 (25) 151) or GaH-ZSM-5 (*Applied Catalysis* 1988 (43) 155), which sequentially oligomerize the feed olefins, cyclize the oligomerized olefins to naphthenes, and dehydrate the naphthenes to the corresponding aromatic compounds. Alternatively, a metal oxide catalyst can be used in presence of molecular oxygen. This latter type of catalyst dimerizes the olefin to the corresponding diene, which is further cyclized to the corresponding aromatic compound. Because such aromatization conditions are more severe than oligomerization conditions, these two processes are generally carried out as separate process steps.

In some embodiments, the production of renewable aromatics from renewable propylene or isobutylene is achieved according to one of the following processes:

Aromatization of light olefins using zeolites, e.g. H-ZSM-5 or GaH-ZSM-5:

$C_3 \rightarrow C_6\text{-}C_8$ Aromatics

$C_4 \rightarrow C_6\text{-}C_8$ Aromatics

Oxidative dehydrodimerization of light olefins using metal oxide/$O_2$:

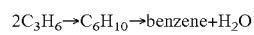

$2C_3H_6 \rightarrow C_6H_{10} \rightarrow \text{benzene} + H_2O$

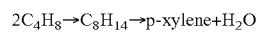

$2C_4H_8 \rightarrow C_8H_{14} \rightarrow \text{p-xylene} + H_2O$

Dimerization of isobutylene to isooctene followed by its aromatization using eta-alumina doped with Cr, Zr, and other elements:

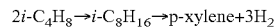

$2i\text{-}C_4H_8 \rightarrow i\text{-}C_8H_{16} \rightarrow \text{p-xylene} + 3H_2$ In most embodiments, however, it is desirable to dehydrocyclize under reducing conditions in order to produce hydrogen as a co-product. The hydrogen produced in the dehydrocyclization reaction can then be used to reduce olefins, particularly isooctene or trimethylheptenes, to the corresponding saturated hydrocarbons which are useful as transportation fuels or fuel additives.

Hydrogenation

Many hydrogenation catalysts are effective, including (without limitation) those containing as the principal component iridium, palladium, rhodium, nickel, ruthenium, platinum, rhenium, compounds thereof, combinations thereof, and the supported versions thereof.

When the hydrogenation catalyst is a metal, the metal catalyst may be a supported or an unsupported catalyst. A supported catalyst is one in which the active catalyst agent is deposited on a support material e.g. by spraying, soaking or physical mixing, followed by drying, calcination, and if necessary, activation through methods such as reduction or oxidation. Materials frequently used as supports are porous solids with high total surface areas (external and internal) which can provide high concentrations of active sites per unit weight of catalyst. The catalyst support may enhance the function of the catalyst agent; and supported catalysts are generally preferred because the active metal catalyst is used more efficiently. A catalyst which is not supported on a catalyst support material is an unsupported catalyst.

The catalyst support can be any solid, inert substance including, but not limited to, oxides such as silica, alumina, titania, calcium carbonate, barium sulfate, and carbons. The catalyst support can be in the form of powder, granules, pellets, or the like. A preferred support material of the present invention is selected from the group consisting of carbon, alumina, silica, silica-alumina, titania, titania-alumina, titania-silica, barium, calcium, compounds thereof and combinations thereof. Suitable supports include carbon, $SiO_2$, $CaCO_3$, $BaSO_4 TiO_2$, and $Al_2O_3$. Moreover, supported catalytic metals may have the same supporting material or different supporting materials.

In one embodiment, the support is carbon. Further useful supports are those, including carbon, that have a surface area greater than 100-200 $m^2/g$. Other useful supports are those, such as carbon, that have a surface area of at least 300 $m^2/g$. Commercially available carbons which may be used include those sold under the following trademarks: Bameby & Sutcliffe™, Darco™, Nuchar™, Columbia JXN™, Columbia LCK™, Calgon PCB™, Calgon BPL™, Westvaco™, Norit™ and Barnaby Cheny NB™. The carbon can also be commercially available carbon such as Calsicat C, Sibunit C, or Calgon C (commercially available under the registered trademark Centaur®).

Particular combinations of catalytic metal and support system suitable for use in the methods of the present invention include nickel on carbon, nickel on $Al_2O_3$, nickel on $CaCO_3$, nickel on $TiO_2$, nickel on $BaSO_4$, nickel on $SiO_2$, platinum on carbon, platinum on $Al_2O_3$, platinum on $CaCO_3$, platinum on $TiO_2$, platinum on $BaSO_4$, platinum on $SiO_2$, palladium on carbon, palladium on $Al_2O_3$, palladium on $CaCO_3$, palladium on $TiO_2$, palladium on $BaSO_4$, palladium on $SiO_2$, iridium on carbon, iridium on $Al_2O_3$, iridium on $SiO_2$, iridium on $CaCO_3$, iridium on $TiO_2$, iridium on $BaSO_4$, rhenium on carbon, rhenium on $Al_2O_3$, rhenium on $SiO_2$, rhenium on $CaCO_3$, rhenium on $TiO_2$, rhenium on $BaSO_4$, rhodium on carbon, rhodium on $Al_2O_3$, rhodium on $SiO_2$, rhodium on $CaCO_3$, rhodium on $TiO_2$, rhodium on $BaSO_4$, ruthenium on carbon, ruthenium on $Al_2O_3$, ruthenium on $CaCO_3$, ruthenium on $TiO_2$, ruthenium on $BaSO_4$, and ruthenium on $SiO_2$.

Raney metals or sponge metals are one class of catalysts useful for the present invention. A sponge metal has an extended "skeleton" or "sponge-like" structure of metal, with dissolved aluminum, and optionally contains promoters. The sponge metals may also contain surface hydrous oxides, absorbed hydrous radicals, and hydrogen bubbles in pores. Sponge metal catalysts can be made by the process described in U.S. Pat. No. 1,628,190, the disclosure of which is incorporated herein by reference.

In various embodiments, the sponge metals include nickel, cobalt, iron, ruthenium, rhodium, iridium, palladium, and platinum. Sponge nickel or sponge cobalt are particularly useful as catalysts. The sponge metal may be promoted by one or more promoters selected from the group consisting of Group IA (lithium, sodium, and potassium), IB (copper, silver, and gold), IVB (titanium and zirconium), VB (vanadium), VIB (chromium, molybdenum, and tungsten), VIIB (manganese, rhenium), and VIII (iron, cobalt, nickel, ruthenium, rhodium, palladium, osmium, iridium, and platinum) metals. The promoter can be used in an amount useful to give desired results. For example, the amount of promoter may be any amount less than 50% by weight of the sponge metal, 0 to 10% by weight, 1 to 5% by weight, or any other value or range of values therein.

Sponge nickel catalysts contain mainly nickel and aluminum. The aluminum is typically in the form of metallic aluminum, aluminum oxides, and/or aluminum hydroxides. Small amounts of other metals may also be present either in their elemental or chemically bonded form, such as iron and/or chromium, and may be added to the sponge nickel to increase activity and selectivity for the hydrogenation of certain groups of compounds. In certain embodiments, chromium and/or iron promoted sponge nickel is employed as a catalyst.

Sponge cobalt catalysts also contain aluminum and may contain promoters. In certain embodiments, the promoters are nickel and chromium, for example in amounts of about 2% by weight based on the weight of the catalyst. Examples of suitable sponge metal catalysts include Degussa BLM 112W, W. R. Grace Raney® 2400, Activated Metals A-4000™, and W. R. Grace Raney® 2724.

As stated above, useful catalytic metals include component iridium, palladium, rhodium, nickel, ruthenium, platinum, rhenium; and useful support materials include carbon, alumina, silica, silica-alumina, titania, titania-alumina, titania-silica, barium, calcium, particularly carbon, $SiO_2$, $CaCO_3$, $BaSO_4$ and $Al_2O_3$. A supported catalyst may be made from any combination of the above named metals and support materials. A supported catalyst may also, however, be made from combinations of various metals and/or various support materials selected from subgroup(s) of the foregoing formed by omitting any one or more members from the whole groups as set forth in the lists above. As a result, the supported catalyst may in such instance not only be made from one or more metals and/or support materials selected from subgroup(s) of any size that may be formed from the whole groups as set forth in the lists above, but may also be made in the absence of the members that have been omitted from the whole groups to form the subgroup(s). The subgroup(s) formed by omitting various members from the whole groups in the lists above may, moreover, contain any number of the members of the whole groups such that those members of the whole groups that are excluded to form the subgroup(s) are absent from the subgroup(s). For example, it may be desired in certain instances to run the process in the absence of a catalyst formed from palladium on carbon.

The optimal amount of the metal in a supported catalyst depends on many factors such as method of deposition, metal surface area, and intended reaction conditions, but in many embodiments can vary from about 0.1 wt % to about 20 wt % of the whole of the supported catalyst (catalyst weight plus the support weight). In particular embodiments, the catalytic metal content range is from about 0.1 wt % to about 10 wt % by weight of the whole of the supported catalyst. In yet other embodiments, the catalytic metal content range is from about 1 wt % to about 7 wt % by weight of the whole of the supported catalyst. Optionally, a metal promoter may be used with the catalytic metal in the method of the present invention. Suitable metal promoters include: 1) those elements from groups 1 and 2 of the periodic table; 2) tin, copper, gold, silver, and combinations thereof; and 3) combinations of group 8 metals of the periodic table in lesser amounts.

Temperature, solvent, catalyst, pressure and mixing rate are all parameters that may affect hydrogenation. The relationships among these parameters may be adjusted to effect the desired conversion, reaction rate, and selectivity in the reaction of the process.

In one embodiment, the hydrogenation temperature is from about 25° C. to 350° C. (e.g., from about 50° C. to about 250° C., or any other value or range of values therein), and in certain embodiments, from about 50° C. to 200° C. The hydrogen pressure can be about 0.1 to about 20 MPa, or about 0.3 to 10 MPa, and in certain embodiments from about 0.3 to about 4 MPa. The reaction may be performed neat or in the presence of a solvent. Useful solvents include those known in the art of hydrogenation such as hydrocarbons, ethers, and alcohols (where the alcohols and ethers, or hydrocarbon solvents can be renewable). In particular embodiments, alcohols such as lower alkanols like methanol, ethanol, propanol, butanol, and pentanol are useful. Selectivities in the range of at least 70% are attainable in the process of the present invention, for example selectivities of at least 85%, at least 90%, or any other value or range of values therein or thereabove. Selectivity is the weight percent of the converted material that is a saturated hydrocarbon where the converted material is the portion of the starting material that participates in the hydrogenation reaction.

Upon completion of the hydrogenation reaction, the resulting mixture of products may be separated by a conventional method, such as for example, by distillation, by crystallization, or by preparative liquid chromatography.

Products

Embodiments of the present invention also relate to renewable hydrocarbon feedstocks and products produced according to the integrated processes described herein. Certain exemplary renewable hydrocarbon feedstocks produced according to the present processes, and products formed therefrom according to the integrated methods described herein, are described below.

Ethylene

The renewable ethylene produced by the processes of the present invention can be used to prepare other hydrocarbons such as propylene, styrene (e.g., by alkylation of benzene) etc. as described herein. Alternatively, at least a portion of the ethylene can be used to prepare other value-added products such as polyethylene (e.g., polyethylene homopolymers and copolymers, waxes, etc.); ethylene oxide (which itself can be used to prepare other products such as polyethylene oxide polymers and copolymers, ethylene glycol, ethylene oxide-containing specialty chemicals such as surfactants, detergents, etc.); halogenated hydrocarbons such as ethylene dichloride, ethylene chloride, ethylene dibromide, chloroethylene, trichloroethylene, and polymers and copolymers derived from these halogenated hydrocarbons (e.g. PVC, PVdC, etc.); propanal (e.g., by hydroformylation) or propylene (e.g. by metathesis as described herein).

Propylene

The renewable propylene produced by the process of the present invention can be used to prepare a variety of renewable products including renewable polypropylene, renewable ethylene propylene rubbers; renewable propylene oxide and renewable polymers prepared from renewable propylene oxide such as polypropylene oxide and polypropylene oxide/polyethylene oxide copolymers, polypropylene oxide polyols for polyurethanes, etc.; renewable aldehydes and ketones such as propanal, acetone, butyraldehyde, isobutyraldehyde, etc.; 2-ethylhexanol and 2-ethylhexanoic acid; aromatics such as cumene and phenol; monomers such acrylic acid, acrylonitrile, and adiponitrile (and derivatives thereof such adipic acid, 1,6-diaminohexane), etc.

Renewable polypropylene can be prepared directly from renewable propylene prepared as described herein using methods and polymerization catalysts known in the art (for example, catalysts and methods described by Hansjorg Sinn and Walter Kaminsky, "Ziegler-Natta Catalysis", *Advances in Organometallic Chemistry* 1980 (18) 99-148 and U.S. Pat. No. 7,563,836). The resulting renewable polypropylene can have any suitable tacticity (e.g., atactic, isotactic, syndiotactic, eutactic) depending on the nature of the catalyst used and polymerization conditions. In addition, renewable propylene prepared as described herein can be copolymerized with other suitable monomers such as ethylene and/or other olefins to prepare thermoplastic polymers (e.g., thermoplastic elastomers), at least a portion of which may be renewable. For example, copolymers prepared with the renewable propylene prepared as described herein can be prepared by the methods described in U.S. Pat. No. 5,272,236.

Renewable polypropylene is particularly useful as a replacement for petroleum derived polypropylene, which is used for a wide variety of products including backing and non-woven fiber sheets used in diapers, as a component of hot melt adhesives (e.g., co-monomers in polyolefin hot melt adhesives), as a component of pressure sensitive adhesives, in extruded/thermoformed/injection molded products, fibers, blown films, cast films, foams, etc., as components and/or copolymers in packaging (films, caps and closures, bottles, containers, etc.), fibers (e.g., nonwoven sheets, carpet fibers, textiles, tape and strapping, staple fibers, bulk and continuous filament, etc.), as components of toys, housewares (e.g., plastic utensils, cups, storage containers, etc.), packing and insulating foams, automotive components (e.g., interior and exterior trim, bumper fascia, etc.), tools (e.g., handles, power tool enclosures, knobs, etc.), electronic enclosures (e.g., mobile phones, TVs, battery cases, etc.), ropes and cables, wire cladding, pipes, etc.

Alternatively, or in addition, renewable polypropylene prepared as described herein can be used to prepare other monomers such as propylene oxide. Renewable propylene oxide can be prepared by a variety of methods, including oxidation with cumene hydroperoxide (e.g., as described in EP 1382602 or U.S. Pat. No. 7,273,941) or oxidation with hydrogen peroxide (e.g. in the presence of a titanium or vanadium silicalite catalyst as described in U.S. Pat. No. 7,273,941 or WO 97/47613). Other methods for oxidizing propylene to propylene oxide known in the art can also be used. The renewable propylene oxide thus formed can then be polymerized or copolymerized using conventional methods (e.g., via base-catalyzed polymerization with a base such as KOH, with a salen cobalt catalyst, etc., using a monofunctional initiator such as an alcohol, ethylene glycol, etc., or a polyfunctional initiator such as glycerol, pentaerythritol, sorbitol, etc.) to provide at least partially renewable polypropylene oxide or at least partially renewable polypropylene oxide copolymers (e.g., ethylene oxide/propylene oxide copolymers).

If cumene hydroperoxide is used as the oxidizing agent to prepare propylene oxide, the cumene hydroperoxide itself can be prepared from renewable propylene and integrated into the process of the present invention as described herein. For example, renewable cumene hydroperoxide can be prepared by the oxidation of renewable cumene, which in turn can be prepared from by various combinations of olefin oligomerization, dehydrocyclization, and/or alkylation steps as described herein. For example, renewable propylene can be dimerized, then dehydrocyclized to form renewable benzene, which can then be alkylated with an additional equivalent of renewable propylene to firm renewable cumene (e.g., as described in U.S. Pat. No. 2,860,173 and U.S. Pat. No. 4,008, 290). Alternatively, renewable propylene can be trimerized and dehydrocyclized directly to form renewable cumene (e.g., similar to the methods described in *Ind. Eng. Chem. Process Des. Dev.* 1986 (25) 151; *Applied Catalysis* 1988 (43) 155; or as described in U.S. Pat. No. 3,879,486). The product renewable cumene can then be oxidized to renewable cumene hydroperoxide using known methods.

Renewable cumene hydroperoxide can be used as an oxidizing agent to oxidize renewable propylene to propylene oxide (e.g., as described in EP 1382602), and/or decomposed to form renewable phenol and renewable acetone (e.g., using the method described in U.S. Pat. No. 5,254,751 or U.S. Pat. No. 2,663,735). In some embodiments, the production of renewable cumene hydroperoxide from renewable propylene can be integrated with a process for preparing renewable propylene oxide, renewable phenol, and renewable acetone (e.g., by preparing renewable cumene by the oligomerization-cyclodehydrogenation-alkylation of renewable propylene, then oxidizing the renewable cumene to form renewable cumene hydroperoxide, then contacting additional renewable propylene with the renewable cumene hydroperoxide to form renewable propylene oxide, and decomposing renewable cumene hydroperoxide to form renewable phenol and renewable acetone), as exemplified in FIG. 8.

The renewable acetone prepared by the decomposition of renewable cumene hydroperoxide can then be used, e.g., as a precursor for methylmethacrylate monomer (via reaction with hydrogen cyanide), a precursor for bisphenol A (via reaction with phenol, e.g., renewable phenol produced in the decomposition of renewable cumene hydroperoxide), or used directly as a renewable industrial solvent. In addition to renewable bisphenol A, the renewable phenol produced by the decomposition of renewable cumene hydroperoxide can be used as a synthetic intermediate in the preparation of, e.g., aspirin, herbicides, cosmetics, sunscreens, etc., and/or as a monomer in the preparation of synthetic resins (phenol/formaldehyde resins such as Bakelite, etc.).

Renewable propylene prepared by the methods disclosed herein can also be converted to oxidized monomers such as renewable acrylic acid, for example by reacting propylene in the vapor phase in the presence of a solid phase catalyst, such as those disclosed in WO 2009/017074, e.g., a two-stage reaction over two different catalyst beds: in the first stage, propylene is oxidized to acrolein using a bismuth molybdate catalyst in a strongly exothermic reaction (at about 370° C.); in the second stage, the acrolein gas is further oxidized to acrylic acid in the gas phase over a molybdenum vanadium oxide catalyst. Alternatively, the renewable propylene can be converted to acrylic acid using the methods of U.S. Pat. No. 6,281,384 (e.g., using a bismuth molybdate multicomponent metal oxide catalyst such as $Mo_{12}CO_{3.5}Bi_{1.1}Fe_{0.8}W_{0.5}Si_{1.4}K_{0.05}O_x$ or a molybdenum vanadate multimetal oxide such as $Mo_{12}V_{4.8}Sr_{0.5}W_{2.4}Cu_{2.2}O_x$); in the presence of a mixed metal oxide catalyst, water, and oxygen using the method of the EP 1201636; or by oxidation in the presence of a mixed metal oxide catalyst as described in JP 07-053448 or WO2000/09260. The resulting renewable acrylic acid can then be polymerized or copolymerized to form renewable polyacrylic acid and polyacrylic acid copolymers, polymerized and crosslinked to form superabsorbent gels e.g. for diapers, esterified to form at least partially renewable acrylic esters (or fully renewable if esterified with renewable alcohols). The at least partially renewable acrylic esters can likewise be polymerized or copolymerized to renewable acrylate ester polymers or copolymers.

Renewable methacrylates can also be formed from renewable propylene, for example by oxycarbonylation of renewable propylene, e.g., using the catalytic process of U.S. Pat. No. 3,907,882 in which the propylene, CO and $O_2$ are reacted in the presence of a rhenium compound prepared from rhenium (V) chloride, aluminum chloride, lithium chloride, and sodium acetate. Analogously to renewable acrylic acid as described herein, renewable methacrylic acid can be esterified and/or polymerized (or copolymerized) to form an at least partially renewable methacrylic acid (ester) polymer or copolymer.

Renewable acrylonitrile can be prepared, e.g., by reacting renewable propylene in the presence of an ammoxidation catalyst (e.g., a multicomponent metal oxide catalyst comprising Bi, Mo, P, and/or Fe oxides), oxygen and ammonia, for example as described in EP 1201636, U.S. Pat. No. 4,230,640, U.S. Pat. No. 4,267,385, U.S. Pat. No. 3,911,089, and U.S. Pat. No. 5,134,105. The resulting renewable acrylonitrile can then be polymerized or copolymerized (e.g., to form renewable polyacrylonitrile).

Renewable acrylonitrile can also be electrochemically dimerized to form adiponitrile, for example using the methods described in GB 1089707 and U.S. Pat. No. 4,155,818, or catalytically dimerized using the methods described in U.S. Pat. No. 4,841,087 (e.g., wherein 1,4-dicyanobutene is reduced to adiponitrile). The resulting renewable adiponitrile can be hydrolyzed to form renewable adipic acid and/or reduced to form renewable hexamethylene diamine (1,6-diaminohexane). The renewable adipic acid or renewable hexamethylene diamine can be polymerized separately with, respectively an appropriate diamine or diacid (or synthetic equivalents thereof), or polymerized together to form completely renewable nylon 6,6. Alternatively, the renewable adipic acid and hexamethylene diamine can be used in the preparation of other valuable and useful materials such as polyurethanes or plasticizers, as crosslinking agents (e.g., for epoxy resins), etc.

The renewable propylene prepared by the integrated methods described herein can also be converted to renewable acetone or propanal by oxidation using known methods, or converted to renewable $C_4$ aldehydes, alcohols, and/or acids by hydroformylation, e.g., using the methods of U.S. Pat. No. 3,274,263 or U.S. Pat. No. 2,327,066.

Figure 9:
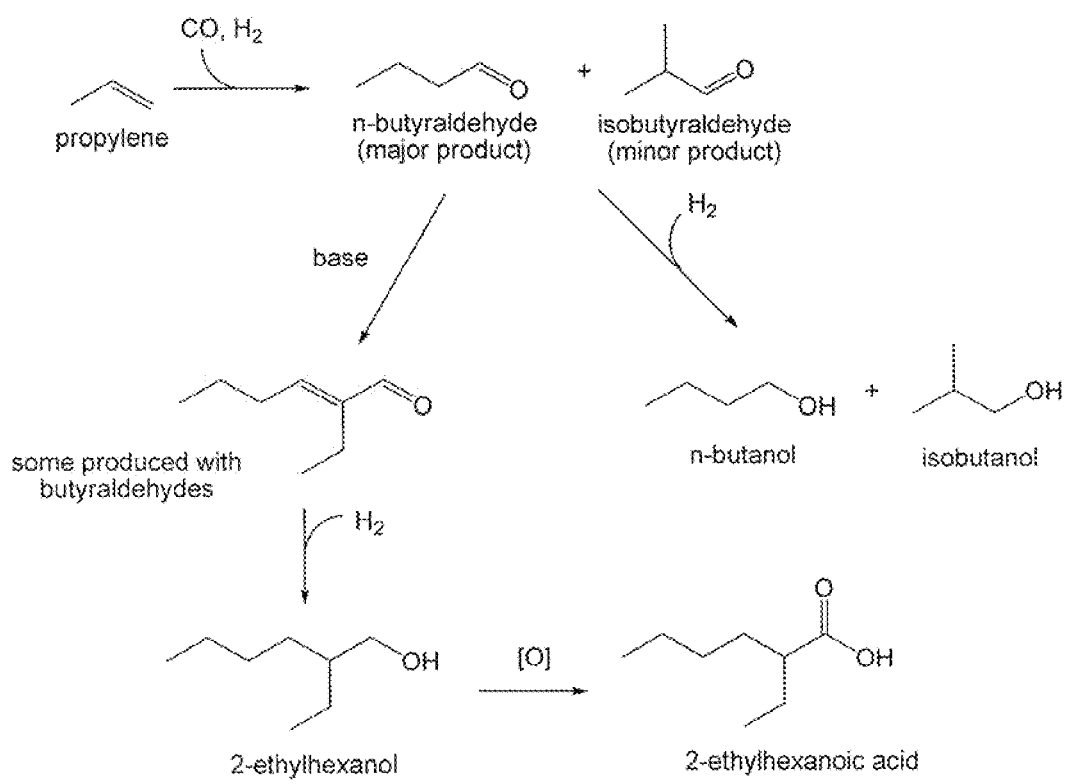
FIG. 9 is a schematic of the formation of butyraldehyde, isobutyraldehyde, n-butanol, isobutanol, 2-ethylhexanol, and 2-ethylhexanoic acid from propylene and ethylene.

Higher alcohols and acids such as 2-ethylhexanol or 2-ethylhexanoic acid can also be prepared from renewable propylene using similar methods, for example by reacting renewable polypropylene, carbon monoxide, hydrogen and acetic acid (e.g., prepared by oxidation of renewable ethanol) in the presence of a suitable catalyst (e.g., cobalt acetate) using the methods of U.S. Pat. No. 2,691,674. 2-Ethylhexanol acetate can be selectively prepared under such conditions at temperatures of about 250° C. to about 290° C. at pressures of about 500-1500 atmospheres and $CO/H_2$ ratios of 0.75-1.5. The renewable 2-ethylhexanol acetate can be hydrolyzed to regenerate acetic acid used in the reaction, and the resulting 2-ethylhexanol can be oxidized to 2-ethylhexanoic acid using known methods. Alternatively, 2-ethylhexanol can be prepared by base-catalyzed aldol condensation of n-butyraldehyde using the method of U.S. Pat. No. 5,144,089. In various embodiments, renewable $C_4$ and $C_6$ aldehydes, alcohols, acids and acid derivatives (e.g., amides, nitriles, acid chlorides, esters, etc.) can be prepared from renewable propylene by known processes such as hydroformylation, and/or base catalyzed aldol condensation, and/or reduction, and/or oxidation of the appropriate intermediates as shown in FIG. 9.

The resulting renewable $C_4$ and $C_6$ aldehydes, alcohols, acids and acid derivatives can be used for various applications, for example in the synthesis of phthalate ester plasticizers (2-ethylhexanol), industrial solvents (butanols), specialty chemicals (metal salts of 2-ethylhexanoic acid), etc.

In still other embodiments, renewable ethylene, butenes, propylene and/or higher olefins produced by the present integrated methods may be oligomerized, e.g., as described in U.S. Ser. No. 12/327,723 to provide renewable transportation fuels, e.g., gasoline, jet fuels and/or diesel fuels.

$C_4$ Oxidized Hydrocarbons

As described above, the process of the present invention provides isobutanol from biomass or $CO_2$ by, e.g., fermentation or thermochemical methods. Renewable isobutanol can be converted to other butanol isomers by, for example, rearrangement of isobutanol, and/or can be converted to various butyraldehydes, butyric acids and/or butyric acid derivatives by appropriate oxidation or reaction of the corresponding alcohol. However, in some cases (for example to ensure complete utilization of the renewable propylene) it may be desirable to convert a certain portion of the renewable propylene provided by the methods of the present invention to various renewable $C_4$ aldehydes, alcohols, and/or acids by hydroformylation.

Butenes

As discussed herein, renewable isobutene and linear butenes produced by the process of the present invention can be used as starting materials to produce higher molecular weight renewable olefins and alkanes useful as renewable fuels and fuel additives, or as monomers for the production of polymers and copolymers, such as polybutene and polyisobutylene suitable for use in a variety of applications, for example chemical intermediates for the preparation of engine oil, fuel additives, and greases; an intermediate in the preparation of dispersants such as polybutenyl succinic anhydride; as intermediates in the preparation of sealants and adhesives; modifiers for polymers such as tackifiers for polyethylene and for adhesive polymers; and in hydrogenated form as components of cosmetic formulations.

Butadiene

The renewable butadiene thus obtained can then be converted, for example, to a wide variety of renewable polymers and co-polymers by most known methods of polymerization and used in a multitude of commercial applications. As described herein, renewable butadiene can be polymerized or copolymerized with other monomers (which themselves may be renewable monomers or monomers obtained from conventional, non-renewable sources). For example, very low molecular weight polymers and copolymers of butadiene, called telomers or liquid polybutadiene, can be prepared by anionic polymerization using initiators such as n-butyl lithium, often with co-initiators such as potassium tert-butoxide or tert-amines as described in U.S. Pat. No. 4,331,823 and U.S. Pat. No. 3,356,754. These low molecular weight oligomers (e.g., MW 500-3000) can be used in pressure sensitive adhesives and thermosetting rubber applications. Butadiene can also be co- and ter-polymerized with vinyl pyridine and/or other vinyl monomers (e.g. renewable vinyl monomers) in an emulsion process to form polymers useful in floor polishes, textile chemicals and formulated rubber compositions for automobile tires. Butadiene can also be anionically polymerized with styrene (e.g., renewable styrene) and vinyl pyridine to form triblock polymers as taught in U.S. Pat. No. 3,891,721 useful for films and other rubber applications.

Butadiene and styrene can be sequentially, anionically polymerized in non-polar solvents such as hexane, to form diblock and triblock polymers, also called SB elastomers, ranging from rigid plastics with high styrene content to thermoplastic elastomers with high butadiene content. These polymers are useful for transparent molded cups, bottles, impact modifiers for brittle plastics, injection molded toys as well as components in adhesives. Solution polybutadiene can be prepared from butadiene, also by anionic polymerization, using initiators such as n-butyl lithium in non-polar solvents without utilizing a comonomer. These elastomers are non-crosslinked during the polymerization and can be used as impact modifiers in high impact polystyrene and bulk polymerized ABS resins, as well as in adhesives and caulks. Solution polymerized polybutadiene can also be compounded with other elastomers and additives before vulcanization and used in automobile tires. Emulsion (latex) polymerization can also be used to convert butadiene and optionally, other monomers such a styrene, methyl methacrylate, acrylic acid, methacrylic acid, acrylonitrile, and other vinyl monomers, to polymers having both unique chemical structure and designed physical structure suitable for specific end use applications.

Emulsion polymerization utilizes water as the continuous phase for the polymerization, surfactants to stabilize the growing, dispersed polymer particles and a compound to generate free radicals to initiate the polymerization. Styrene-butadiene emulsion rubber used for automobile tires can be made by this process. Renewable vinyl acids such as acrylic acid and methacrylic acid (as described herein) can be copolymerized in the styrene butadiene rubber. Low levels (0.5-3%) of vinyl acids improve the stability of the latex and can be beneficial in formulated rubber products such as tires, especially when containing polar fillers. Higher levels of acid in rubber latexes, often called carboxylated latex, are used beneficially in paper coating. Latex polymerization is also used to produce rubber toughened plastics and impact modifiers. Impact modifiers made by latex polymerization are also called core-shell modifies because of the structure that is formed while polymerizing the monomers that comprise the polymer.

MBS resins are made by a sequential emulsion process where butadiene (B) and styrene (S) are first polymerized to form the rubber particle core, typically 0.1-0.5 micrometers in diameter, and then methyl methacrylate (M) is polymerized to form a chemically grafted shell on the outer surface of the SB rubber core, for example as taught in U.S. Pat. No. 6,331,580. This impact modifying material is isolated from the latex and blended with plastics to improve their toughness. If acrylonitrile (A) is used in place of the methyl methacrylate, with slight variations in the process, such as disclosed in U.S. Pat. No. 3,509,237 and U.S. Pat. No. 4,385,157, emulsion ABS is the product. Each of these components in ABS (including acrylonitrile) may be renewable, produced by the methods described herein. ABS is used in injection molding and extrusion processes to produce toys, automobile parts, electronic enclosures and house wares. Nitrile rubber is produced in a similar emulsion polymerization process when butadiene and acrylonitrile are copolymerized together to produce a polar elastomer that is very resistant to solvents. Higher butadiene content in the elastomer provides a softer, more flexible product while higher acrylonitrile content results in more solvent resistance. The rubber is isolated from the latex by coagulation and can be fabricated into gloves, automotive hoses, and gaskets where its high resistance to solvents is an advantage.

Renewable butadiene prepared by the process described herein can also be converted to renewable 1,4-butanediol (BDO) and/or renewable tetrahydrofuran (THF), for example using the process described in JP 10-237017 and JP 2001002600 (illustrated below in Scheme 1), in which butadiene is reacted with acetic acid and oxygen in the presence of a palladium catalyst (liquid phase at about 70° C. and 70 bar, using a promoter such as Sb, Bi, Se or Te) to form 1,4-diacetoxy-2-butene, which is then hydrogenated (liquid phase, at about 50° C. and 50 bar over a conventional hydrogenation catalyst such as Pd/C) to 1,4-diacetoxybutane. Acidic hydrolysis of the 1,4-diacetoxybutane (e.g., using an acidic ion exchange resin) provides BDO and THF in high yield.

SCHEME 1:

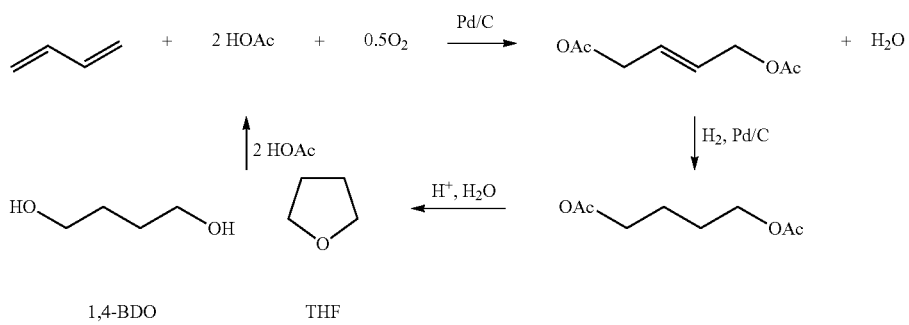

1,4-BDO    THF

Renewable BDO and THF can be converted to a variety of renewable products. For example renewable BDO can be reacted with a suitable diisocyanates to form renewable Lycra™ and Spandex™ products, as well as thermoplastic urethane elastomers. Renewable BDO can also be used to form renewable polybutylene terephthalate by reacting renewable BDO with terephthalic acid or terephthalate esters, or can be copolymerized with renewable aliphatic diacids such as adipic acid or succinic acid to form renewable aliphatic polyesters such as polybutylene adipate or polybutylene succinate. In some embodiments the terephthalic acid or terephthalate esters can be renewable, prepared by oxidation of renewable xylene made, e.g., by the method described in U.S. Ser. No. 12/327,723 and U.S. 61/295,886. Renewable BDO can also be used to prepare renewable γ-butyrolactone (GBL), renewable pyrrolidone solvents such as N-methylpyrrolidinone (NMP), renewable N-vinylpyrrolidinone (NVP), etc. as illustrated below in Scheme 2:

SCHEME 2:

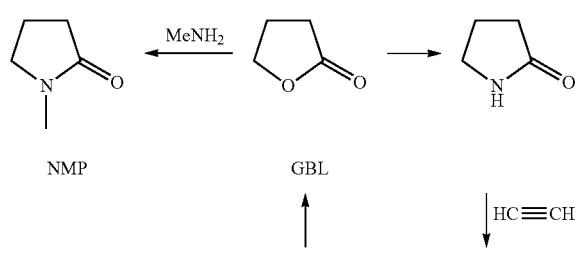

NMP    GBL

-continued

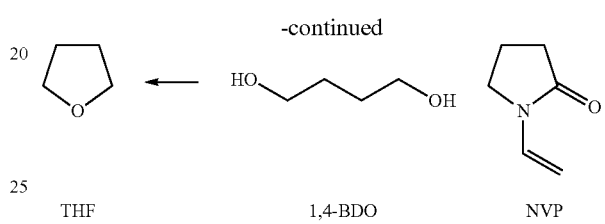

THF    1,4-BDO    NVP

Renewable GBL and NMP can be used as solvents, and renewable NVP can be used in personal care products such as hairspray.

Renewable butadiene prepared by the processes described herein can also be used to form renewable dodecanedioic acid (DDDA), or renewable lauryllactam by forming the oxime of the intermediate cyclododecanone, then rearranging the oxime to lauryllactam (e.g., using the method of U.S. Pat. No. 6,649,757). The lauryllactam can then be polymerized to form renewable nylon-12, as shown below in Scheme 3:

SCHEME 3:

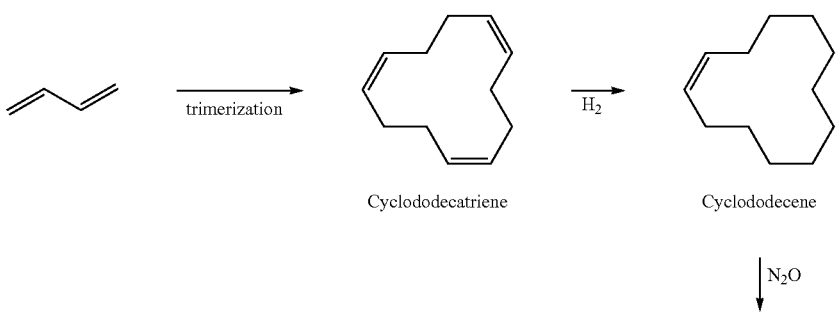

Cyclododecatriene    Cyclododecene

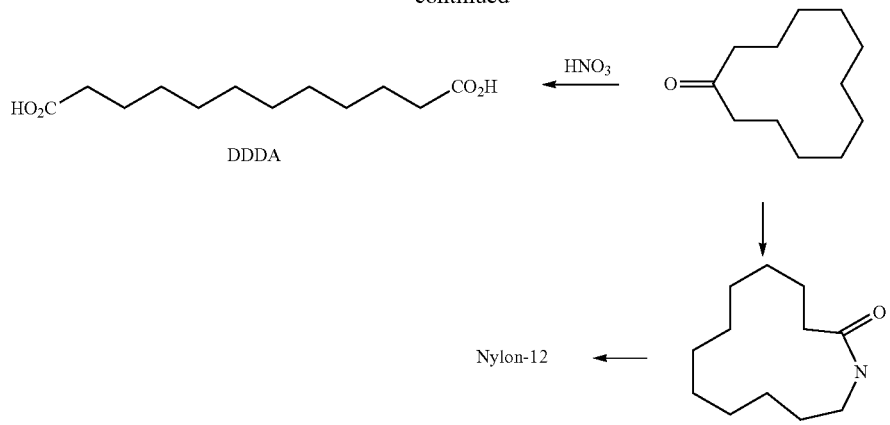

Renewable butadiene prepared by the processes described herein can also be used to prepare renewable chloroprene, which can be polymerized to provide renewable synthetic rubbers. Renewable chloroprene can be prepared by chlorinating renewable butadiene (e.g., free radical, gas phase chlorination with $Cl_2$ at 250° C. and 1-7 bar to give a mixture of cis and trans-1,4-DCB as well as 3,4-DCB). At butadiene conversions of 10-25%, the selectivity to this mixture of DCBs can be 85-95%. 3,4-dichloro-1-butene (3,4-DCB) can be dehydrochlorinated to form chloroprene (e.g., using dilute alkaline catalysts at 85° C.), as shown below in Scheme 4. The 1,4-DCB by-products can be isomerized to 3,4-DCB using a copper catalyst. In addition, by distilling off the 3,4-DCB during the reaction (b.p. 123° C. vs. 155° C. for the 1,4-isomers), the equilibrium of the reaction can be shifted to provide a selectivity of 95-98%.

SCHEME 4:

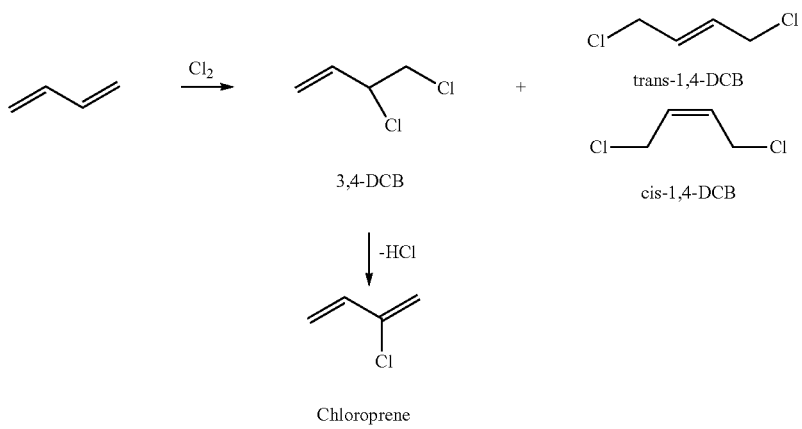

Renewable butadiene prepared by the processes described herein can also be used to prepare renewable nylon-6,6 (Scheme 5). For example, renewable nylon-6,6 can be prepared by reacting renewable butadiene with HCN in the presence of a zero valent nickel catalyst to provide adiponitrile. Adiponitrile can be hydrogenated to form hexamethylenediamine (HMD), and hydrolyzed to form adipic acid. The HMD and adipic acid can then be polymerized to form nylon-6,6.

SCHEME 5:

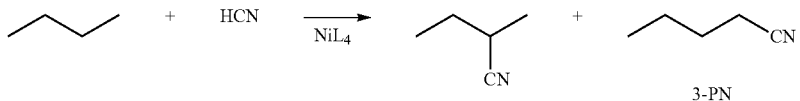

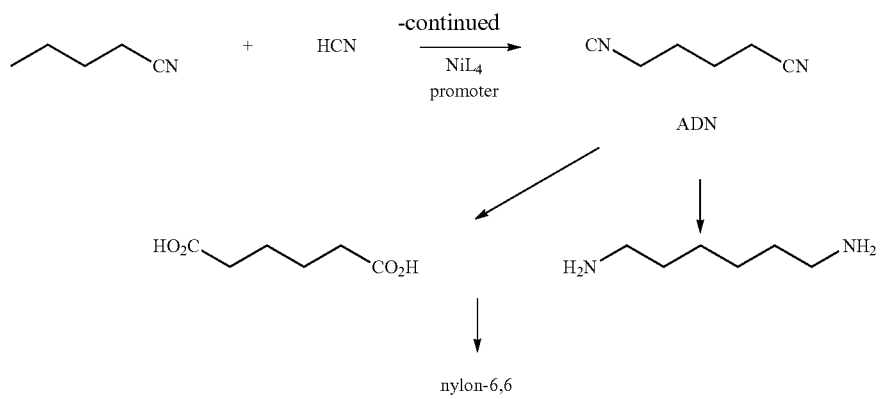

Alternatively, as shown in Scheme 6, renewable adiponitrile can be hydrocyanated and cyclized to renewable caprolactam (CL), e.g., using a doped Raney Ni (using the method of U.S. Pat. No. 5,801,286) and cyclized to CL in the presence of water (using the method of U.S. Pat. No. 5,693,793). The renewable caprolactam can then be polymerized to form renewable nylon-6 using methods known in the art.

SCHEME 6:

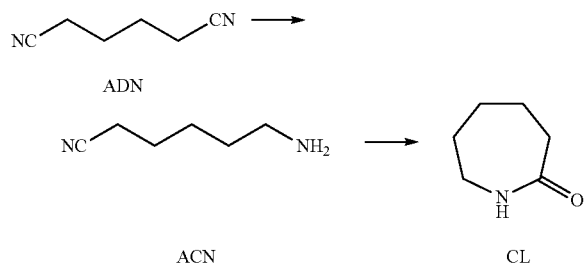

Renewable butadiene prepared by the processes described herein can also be used to prepare renewable sulfolene and sulfolane using the method illustrated in Scheme 7:

Scheme 7:

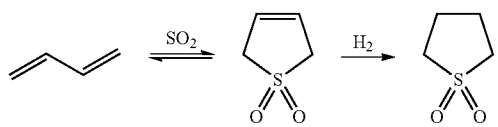

Renewable butadiene prepared by the processes described herein can also be used to prepare renewable styrene, renewable polystyrene, and renewable styrenic polymers (e.g., renewable SBR rubbers). Renewable styrene can be prepared, for example by dimerizing renewable butadiene to form vinylcyclohexene, which can be dehydrogenated in a stepwise fashion to form ethyl benzene (e.g., using the method of WO 2003/070671), then styrene (e.g., using the method of U.S. Pat. No. 4,229,603). Alternatively, vinylcyclohexene can be dehydrogenated directly to styrene. The renewable styrene can be homopolymerized to form renewable polystyrene, copolymerized with renewable butadiene to form SBR rubber, etc.

Renewable butadiene prepared by the processes described herein can also be used to prepare renewable ethylidene norbornene (ENB) for producing completely renewable or partially renewable ethylene-propylene-diene rubber (depending on whether renewable ethylene and/or propylene are used). Renewable ethylene can be prepared by dehydrogenating renewable ethanol (e.g. produced by fermentation or thermochemical methods), and renewable propylene can be prepared, for example by the methods described in U.S. 61/155,029. Renewable ENB can be prepared, for example, by reacting renewable butadiene and dicyclopentadiene in a four-step process. In the first step, dicyclopentadiene is decoupled to cyclopentadiene and reacted with renewable butadiene via Diels-Alder condensation to vinylnorbornene (VNB). This is followed by distillation to obtain refined VNB, which is catalytically isomerized (U.S. Pat. No. 4,720,601) to ENB.

Renewable butadiene prepared by the processes described herein can also be thermally dimerized to form renewable 1,5-cyclooctadiene (COD) using the methods of, e.g., U.S. Pat. No. 4,396,787. Renewable COD can be used in the preparation of renewable ethylene oligomerization catalysts such as Ni(COD)$_2$. Butadiene can also be dimerized to produce 1-octene and 1-octanol.

In other embodiments, the dehydration of 3-methyl-1-butanol produces a mixture of methyl butenes and small amounts of other pentenes which upon treatment with a dehydrogenation catalyst forms primarily isoprene from methylpentenes (e.g. 2-methyl-1-butene, 2-methyl-2-butene, 3-methyl-1-butene), for example 3-methyl-1-butene, and other pentadienes, such as 1,3-pentadiene, from other pentenes. The pentadienes are separated from each other by distillation. Dehydration catalysts and conditions are optimized to produce varying amounts of specific olefins, and their resulting di-olefins upon treatment with a dehydrogenation catalyst.

The purification of isobutene as described above produces renewable isobutene that meets all current industrial specifications and can be used to manufacture all chemicals and materials currently produced, e.g., from conventional petroleum-based isobutene. For example, renewable or partially renewable polyisobutylene, butyl rubber, methyl methacrylate, isoprene, and other chemicals can be produced by the methods of the present invention. Renewable isobutene can also be oxidized under suitable conditions to provide methacrylic acid and methacrylic acid esters (Scheme 8). Isobutene can be oxidized over suitable metal oxide catalysts (e.g., using the methods described in JP 2005-253415) at temperatures of about 300-500° C. to methacrolein (MAL) which is then further oxidized to methacrylic acid (MMA)

(WO 2003053570) at temperatures of about 350-500° C. The resultant methacrylic acid can be further esterified to methylmethacrylate. The oxidation of isobutene to MMA may also be accomplished in a single step (e.g. as described in WO2003053570).

SCHEME 8:

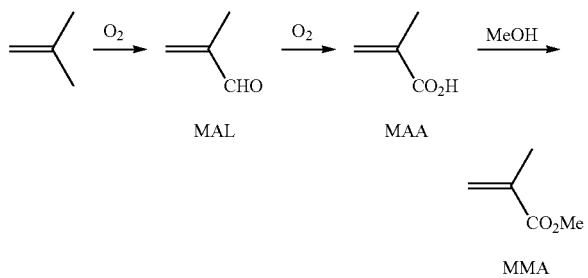

MAL    MAA    MMA

An alternative process for the preparation of MMA is by the oxidative esterification of MAL to MMA (e.g., as described in U.S. Pat. No. 4,518,796) using catalysts such as Pd/Pb/Mg—Al$_2$O$_3$ (e.g., as described in JP 2006306731) and Pd$_5$Bi$_2$Fe/CaCO$_3$ (Scheme 9.

SCHEME 9:

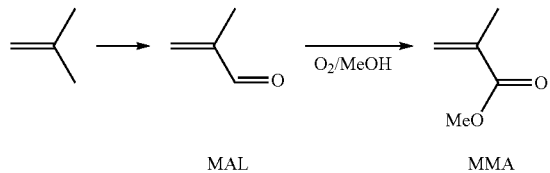

MAL    MMA

Additionally, all materials currently produced from butadiene such as synthetic rubbers and nylon can be manufactured from the renewable butadiene produced by the dehydrogenation of renewable butenes according to the present invention. For example, butadiene is used directly as a monomer and co-monomer for the production of synthetic rubber. It is also converted into "oxidized" monomers such as 1,4-butanediol, adiponitrile, and adipic acid as described herein for the production of polyester and nylon materials (e.g., adipic acid is produced by the hydrocarboxylation of butadiene in the presence of a suitable catalyst, CO and water; e.g., adiponitrile is produced by the hydrocyanation of butadiene in the presence of a suitable catalyst). The production of renewable isoprene from the dehydrogenation of methylbutenes or the hydroformylation and dehydration of renewable isobutene allows the preparation of renewable or partially renewable versions of all chemicals and materials produced from isoprene, especially synthetic rubber and other polymers.

One of the major industrial uses of isobutene is in the production of butyl rubber primarily for use in automobile tires. Butyl rubber is a high performance polymer comprised of high purity isobutene crosslinked with di-olefins such as butadiene or isoprene (e.g., U.S. Pat. No. 2,984,644; Dhaliwal G K, Rubber Chemistry and Technology 1994 (67) 567). Typically, 1-3% of di-olefin is blended with isobutene and co-polymerized in the presence of a polymerization catalyst such as aluminum chloride and other metal salts.

In some embodiments, renewable isoprene is produced by contacting 3-methyl-1-butanol or 2-methyl-1-butanol with a dehydration catalyst and a dehydrogenation catalyst, under conditions similar to those described herein for preparing renewable butadiene. The renewable isoprene thus formed may then blended with renewable isobutene, obtained by the methods described above or by conventional methods such as hydration of isobutylene to t-butanol and subsequent dehydration to isobutene, to form a renewable monomer feedstock for the production of renewable butyl rubber. Petroleum-based isoprene and isobutene can also used with the renewable isoprene and/or isobutene to produce butyl rubber that is partially renewable. In addition to blending purified isoprene with purified isobutene to produce butyl rubber, a renewable blend of isobutene and isoprene can be produced by contacting a mixture of isobutanol and 3-methyl-1-butanol (or 2-methyl-1-butanol) with a dehydration catalyst to form isobutylene and 3-methyl-butenes (or 2-methyl-butenes) and then contacting this olefin mixture with a dehydrogenation catalyst to form isobutene and isoprene. By-products such as butadiene and other C$_5$ olefins and di-olefins are removed by extractive distillation to give mixtures containing only isobutene and isoprene. The amount of isoprene in the mixture can be Controlled by manipulating the 3-methyl-1-butanol producing pathway in the host microorganism or the appropriate selection of catalyst in the thermochemical conversion of biomass. In some embodiments, the 3-methyl-1-butanol (or 2-methyl-1-butanol) concentration is tuned to 1-3% of the isobutanol produced such that the resulting isobutene/isoprene mixture can be directly used to produce butyl rubber. Alternatively, in other embodiments a higher concentration of 3-methyl-1-butanol is produced to form a mixture of isobutene and isoprene that is then diluted with pure isobutene to optimize butyl rubber production. The isoprene produced from 3-methyl-1-butanol (or 2-methyl-1-butanol) containing isobutanol is also separately removed and blended with isobutene to the appropriate concentration. Alternatively, the butadiene produced by the dehydrogenation of 1- and 2-butenes is used as a cross-linking agent in a butyl rubber product.

In view of the foregoing description, it will be appreciated that starting from simple renewable ethanol and isobutanol feedstocks, essentially any product currently derived or produced from petroleum feedstocks can be produced by the present integrated processes. Exemplary methods of producing certain renewable mono- and polyolefins, unsubstituted and substituted aromatics, derivatives thereof (e.g., acids, esters, acid derivatives, heterosubstituted compounds, etc.) and polymers and products therefrom have been described. It will be appreciated that methods and/or transformation as described herein for one compound are generally analogous and applicable to other, similar compounds and that such transformations and products are within the scope of the present integrated methods.

The present integrated processes will now be further described with reference to the following, non-limiting examples.

Example 1

Production of Isobutanol from Lignocellulosics

A cellulosic material consisting of 45% cellulose, 25% hemicellulose, 22% lignin and 8% other materials is pretreated to yield a slurry of 8% insoluble cellulose with about 4% insoluble lignin, 1% glucose, 40 g/L xylose, 2 g/L mannose, 2 g/L galactose, 1 g/L arabinose, 5 g/L acetic acid in solution. The slurry is fed into an agitated saccharification and fermentation vessel and charged with cellulase enzyme sufficient to hydrolyze 80% of the cellulose 72 hours. A microorganism known to ferment glucose, xylose, mannose, galactose and arabinose to isobutanol is added to the fermentation, and the vessel is agitated for 72 hours. Isobutanol produced by the fermentation is separated from the fermentation broth by distillation. The first isobutanol-containing distillation cut contains 20% w/w isobutanol and 80% w/w water that condenses to form two phases—a light phase containing 85% isobutanol and 15% water and a heavy phase containing 8% isobutanol and 92% water. The light phase is distilled a second time and two low-water cuts of isobutanol are obtained. One cut is comprised of 99.5% isobutanol and 0.5% water while the second cut is comprised of 98.8% isobutanol, 1% 3-methyl-1-butanol, and 0.2% water.

Example 2

Dehydration of Isobutanol

Isobutanol obtained in Example 1 was fed through a preheater and to a fixed-bed tubular reactor packed with a commercial dehydration catalyst (BASF AL3996). The internal reactor temperature was maintained at 300° C. and the reactor pressure was atmospheric. The WHSV of the isobutanol was 6 hf$^{-1}$. Primarily isobutene and water were produced in the reactor and separated in a gas-liquid separator at 20° C.; the water had 1% of unreacted isobutanol and conversion was 99.8%. GC-MS of the gas phase effluent indicated it was 96% isobutene, 2.5% 2-butene (cis and trans) and 1.5% 1-butene.

Example 3

Dehydration of Isobutanol

Isobutanol obtained in Example 1 is fed through a preheater and to a fixed-bed tubular reactor packed with a commercial dehydration catalyst (e.g., an X-type zeolite). The internal reactor temperature is maintained at 370° C. and the reactor pressure is atmospheric. The WHSV of the isobutanol is 3 hr$^{-1}$. A mixture of $C_4$ olefins and water are produced in the reactor and separated in a gas-liquid separator at 20° C.; the water has <1% of unreacted isobutanol and conversion is >99.8%. GC-MS of the gas phase effluent indicates it is 50% isobutene, 40% 2-butene (cis and trans) and 10% 1-butene.

Example 4

Co-Dehydration of Ethanol and Isobutanol 60 g of a commercial γ-alumina dehydration catalyst (BASF AL-3996) is loaded into a fixed-bed tubular reactor. A feed mixture is prepared by mixing 250 mL of ethanol with 750 mL of isobutanol. The feed mixture is pumped through a preheater and onto the catalyst bed at a feed rate of 2.5 mL/min. The internal reactor temperature is maintained at 350° C., the pressure was atmospheric, and the weight hourly space velocity (WHSV) of the mixed alcohol feed is ~2/hr. The products are separated in a gas-liquid separator. The water contains 0.9 wt % ethanol and 0.3 wt % isobutanol indicating conversions of 99% and 99.9% respectively. The gas-phase effluent is 35% ethylene and 65% butenes (molar basis). The butenes are found to be 55% isobutene, 13% 1-butene, 12% cis-2-butene, and 20% trans-2-butene.

Example 4A

Dehydration of Dry Isobutanol

Dry isobutanol (<1 wt % water) obtained in Example 1 was fed through a preheater to a fixed-bed tubular reactor packed with a commercial γ-alumina dehydration catalyst (BASF AL-3996). The internal reactor temperature was maintained at 325° C. and the reactor pressure was atmospheric. The WHSV of the isobutanol was 5 hr$^{-1}$. Primarily isobutene and water were produced in the reactor, and were separated in a gas-liquid separator at 20° C.; the water had <1% of unreacted isobutanol and the conversion was >99.8%. GC-FID analysis of the gas phase effluent indicated it was 95% isobutene, 3.5% 2-butene (cis and trans) and 1.5% 1-butene.

Example 5

Purification of Isobutene by Dehydrogenation of Butenes

A mixed butene stream from Example 2, containing 96% isobutene, 2.5% 2-butenes (cis and trans), and 1.5% 1-butene is mixed with air at a relative feed rate of 10:1 butenes:air. The resultant mixture is 1.9% oxygen and 3.6% linear butenes. The mixture is preheated to 400° C. and fed at a GHSV of 300 hr$^{-1}$ to a fixed-bed tubular reactor loaded with 2 catalyst beds in sequence; the first contains $ZnFe_2O_4$ and the second contains $CO_9Fe_3BiMoO_{51}$. The effluent from the reactor is dried over a molecular sieve column to remove water. Nitrogen and oxygen are removed by passing the $C_4$ stream through a gas-liquid separator at −78° C. (dry ice bath). The $C_4$ product is analyzed via GC-MS. The composition is found to be 96% isobutene, 3.9% butadiene, and 0.1% linear butenes. butadiene is stripped from the gas stream by extraction with acetonitrile. The resultant stream is 99.9% isobutene and 0.1% linear butenes with trace butadiene (<0.01%).

Example 6

Purification of Isobutene by Dehydrogenation of Butenes

A mixed butene stream from Example 3, containing 50% isobutene, 40% 2-butenes (cis and trans), and 10% 1-butene is mixed with air at a relative feed rate of 4:5 butenes:air. The resultant mixture is 11.7% oxygen and 22.2% linear butenes. The mixture is preheated to 400° C. and fed at a GHSV of 300 hr$^{-1}$ to a fixed-bed tubular reactor loaded with 2 catalyst beds in sequence; the first contains $ZnFe_2O_4$ and the second contains $CO_9Fe_3BiMoO_{51}$. The effluent from the reactor is dried over a molecular sieve column to remove water. Nitrogen and oxygen are removed by passing the $C_4$ stream through a gas-liquid separator at −78° C. (dry ice bath). The $C_4$ product is analyzed via GC-MS. The composition is found to be 50% isobutene, 49.9% butadiene, and 0.1% linear butenes. butadiene is stripped from the gas stream by extraction with acetonitrile. The resultant stream is 99.9% isobutene and 0.1% linear butenes with trace butadiene (<0.01%).

Example 7

Preparation of Butadiene from Butenes 120 sccm of nitrogen and 120 sccm of 2-butene (mixture of cis and trans) was fed through a preheater and to a fixed-bed tubular reactor packed with 15 g of a commercial $Cr_2O_3$ on alumina dehydrogenation catalyst (BASF Snap catalyst). The internal reactor temperature was maintained at 600° C. and the reactor pressure was atmospheric. The WHSV of the 2-butene was about 1 hf. GC-FID of the gas phase effluent indicated it was 74% linear butenes (mixture of 1-, cis-2-, and trans-2-), 16% butadiene, 2.5% n-butane, and 7.5% $C_1$-$C_3$ hydrocarbons. The resulting conversion of 2-butene was 26% (ignoring rearrangement to 1-butene) with a selectivity to butadiene of 61.5% based on % carbon.

Example 9

Integrated Preparation of Butadiene from Isobutanol

Renewable wet isobutanol (containing 15% water and ~4% ethanol) obtained from fermentation was fed through a preheater and to a fixed-bed tubular reactor packed with a commercial γ-alumina dehydration catalyst (BASF Snap catalyst). The internal reactor temperature was maintained at 400° C. and the reactor pressure was atmospheric. The WHSV of the isobutanol was ~0.1 $hr^{-1}$. The products were separated in a gas-liquid separator at 20° C., where relatively pure water was removed as the liquid product. The gas phase product was dried over a molecular sieve bed. GC-FID of the gas phase effluent from the dehydration reactor was 82% isobutylene, 13% linear butenes (mixture of 1-butene, and cis- and trans-2-butene), 4.5% ethylene, and 0.5% propylene. The flow of the gas-phase stream was ~120 sccm. This stream was combined with 120 sccm of nitrogen and was fed through a preheater and to a fixed-bed tubular reactor packed with 15 g of a commercial $Cr_2O_3$ on alumina dehydrogenation catalyst. The internal reactor temperature was maintained at 600° C. and the reactor pressure was atmospheric. The WHSV of the mixed butene stream was about 1 $hr^{-1}$. GC-FID of the gas phase effluent indicated it was 78.5% isobutylene with 2.5% isobutane, 7.5% linear butenes, 3.7% ethylene with 0.6% ethane, 2.9% butadiene, and the remaining 4.4% was methane and propylene. This indicates an approximate yield of 22% butadiene based on linear butenes fed to the dehydrogenation reactor.

Example 10

Preparation of Propylene from Ethylene and 2-Butenes

A metathesis catalyst is prepared by dissolving 0.83 g of ammonium metatungstate in 100 mL of distilled water, stirring the resulting solution with 5 g of silica gel (300 $m^2$/g, pore volume 1 mL/g), evaporating the water, then calcining the resulting solid in air at 550° C. for 6 hours. The resulting supported tungsten oxide catalyst is then mixed with hydrotalcite at a weight ratio of about 1:5 tungsten oxide catalyst/hydrotalcite. A metathesis reactor is then prepared by adding the tungsten oxide catalyst/hydrotalcite catalyst to a fixed-bed tubular reactor.

An ethylene guard column is prepared by loading a fixed-bed tubular reactor sequentially with approximately equal amounts of hydrotalcite and γ-alumina, and a butene guard column is prepared by loading a fixed-bed tubular reactor sequentially with the tungsten oxide catalyst (prepared as described above) and approximately twice the amount (by weight) of hydrotalcite.

The disproportionation reaction is carried out by first purging the guard columns and metathesis reactor with an approximately 100 mL/min flow of N2 at atmospheric pressure. The purged reactor and guard columns are then heated to 500° C. with continuing N2 flow for 1 hr. The guard columns and reactors are maintained at 500° C.; then approximately 100 mL/min of H2 gas at atmospheric pressure is added to the N2 purge, and maintained for 2 hrs. The reactor is then cooled to 200° C., and the guard columns cooled to 50° C., and the flow of N2 and 112 is reduced to 50 mL/min. After purification in the respective guard columns, liquefied renewable 2-butene is then introduced into the butene guard column at a rate of 0.10 g/min, and liquefied renewable ethylene is introduced into the ethylene guard column at a flow rate of 64.5 mL/min and a pressure of 3.5 MPa. The ethylene, 2-butene, and H2 (7.0 mL/min, 3.5 MPa) were then charged into the metathesis reactor (after preheating to 200° C.). The butene conversion rate obtained by subtracting the total amount of trans-2-butene, cis-2-butene and 1-butene contained in the outlet gas from the metathesis reactor is 71%. The propylene selectivity based on butene is 90%. Small amounts of propane, pentene and hexene are also produced.

Example 11

Oligomerization of Isobutene

The product stream from Example 4a was dried over molecular sieves, compressed to 60 psig, cooled to 20° C. so that the isobutene was condensed to a liquid and pumped with a positive displacement pump into a fixed-bed oligomerization reactor packed with a commercial ZSM-5 catalyst (CBV 2314). The reactor was maintained at 175° C. and a pressure of 750 psig. The WHSV of the isobutene-rich stream was 15 $hr^{-1}$. The reactor effluent stream was 10% unreacted butenes, 60% isooctenes (primarily 2,4,4-trimethylpentenes), 28% trimers, and 2% tetramers.

Example 12

Oligomerization of Isobutene

The product stream from Example 4a is co-fed with 50% isobutane to a compressor, condensed and pumped into a fixed-bed oligomerization reactor packed with Amberlyst 35 (strongly acidic ionic exchange resin available from Rohm & Haas). The reactor is maintained at 120° C. and a pressure of 500 psig. The WHSV of the isobutene-rich stream is 100 $hr^{-1}$. The product stream is about 50% isobutane (diluents), about 3% unreacted butenes, about 44% isooctenes (primarily 2,4,4-trimethylpentenes), and about 3% trimers.

Example 13

Dehydrocyclization of Isooctene

Isooctene from Example 11 was distilled to remove trimers and tetramers and then fed at a molar ratio of 1.3:1 mol nitrogen diluent gas to a fixed bed reactor containing a commercial chromium oxide doped alumina catalyst (BASF D-1145E ⅛"). The reaction was carried out at atmospheric pressure and a temperature of 550° C., with a WHSV of 1.1 $hr^{-1}$. The reactor product was condensed and analyzed by GC-MS. Of the xylene fraction, p-xylene was produced in greater than 80% selectivity. Analysis by method ASTM D6866-08 showed p-xylene to contain 96% biobased material.

Example 14

Hydrogenation of Isooctene

Palladium on carbon (0.5% Pd/C, 2 g) catalyst was charged into a 2000 mL stainless steel batch reactor equipped with stirrer. 1000 mL of a hydrocarbon fraction comprising isooctene isomers was charged into the reactor. The reactor was then flushed with nitrogen and pressurized with 100 psig hydrogen. The reaction mixture was stirred for one hour and the temperature was increased from ambient temperature to 80-100° C. The reactor was subsequently cooled down to ambient temperature and excess hydrogen remaining in the reactor was released, and the reactor purged with a small amount of nitrogen. The product was filtered off from the catalyst and GC analysis of the product showed 100% hydrogenation.

Example 15

Oxidation of Renewable P-Xylene to Terephthalic Acid

A 300 mL Pan reactor was charged with glacial acetic acid, bromoacetic acid, cobalt acetate tetrahydrate, and p-xylene, obtained from Example 13, in a 1:0.01:0.025:0.03 mol ratio of glacial acetic acid:bromoacetic acid: cobalt acetate tetrahydrate: p-xylene. The reactor was equipped with a thermocouple, mechanical stirrer, oxygen inlet, condenser, pressure gauge, and pressure relief valve. The reactor was sealed and heated to 150° C. The contents were stirred and oxygen was bubbled through the solution. A Pressure of 50-60 psi was maintained in the system and these reaction conditions were maintained for 4 h. After 4 h, the reactor was cooled to room temperature. Terephthalic acid was filtered from solution and washed with fresh glacial acetic acid.

Example 16

Purification of Renewable Terephthalic Acid

Terephthalic acid from Example 15 was charged to a 300 mL Pan reactor with 10% Pd on carbon catalyst in a 4.5:1 mol ratio of terephthalic acid:10% Pd on carbon. Deionized water was charged to the reactor to make a slurry containing 13.5 wt. % terephthalic acid. The reactor was equipped with a thermocouple, mechanical stirrer, nitrogen inlet, hydrogen inlet, pressure gauge, and pressure relief valve. The Parr reactor was sealed and flushed with nitrogen. The Parr reactor was then filled with hydrogen until the pressure inside the reactor reached 600 psi. The reactor was heated to 285° C. and the pressure inside the vessel reached 1000 psi. The contents were stirred under these conditions for 6 h. After 6 h, contents were cooled to room temperature and filtered. The residue was transferred to a vial and N,N-dimethylacetamide was added to the vial in a 5:1 mol ratio of N,N-dimethylacetamide:terephthalic acid. The vial was warmed to 80° C. for 30 minutes to dissolve the terephthalic acid. The contents were filtered immediately; Pd on carbon was effectively removed from the terephthalic acid. Crystallized terephthalic acid filtrate was removed from the collection flask and was transferred to a clean filter where it was washed with fresh N,N-dimethylacetamide and dried. A yield of 60% purified terephthalic acid was obtained.

Example 17

Polymerization of Terephthalic Acid to Make Renewable Pet

Purified terephthalic acid (PTA) obtained from Example 16 and ethylene glycol are charged to a 300 mL Parr reactor in a 1:0.9 mol ratio of PTA:ethylene glycol. Antimony (III) oxide is charged to the reactor in a 1:0.00015 mol ratio of PTA:antimony (III) oxide. The reactor is equipped with a thermocouple, mechanical stirrer, nitrogen inlet, vacuum inlet, condenser, pressure gauge, and pressure relief valve. The Parr reactor is sealed, flushed with nitrogen, heated to a temperature of 240° C., and pressurized to 4.5 bar with nitrogen. Contents are stirred under these conditions for 3 h. After 3 h, the temperature is increased to 280° C. and the system pressure is reduced to 20-30 mm by connecting the reactor to a vacuum pump. Contents are stirred under these conditions for 3 h. After 3 h, the vacuum valve is closed and the contents of the reactor are flushed with nitrogen. The reactor is opened and contents are immediately poured into cold water to form PET pellets.

Example 18

Preparation of Diisobutylene from Isobutanol

Isobutanol produced by fermentation was separated from the fermentation broth by distillation. The isobutanol, which contains 16% water, was passed through a chemical reactor containing a commercial γ-alumina catalyst heated to 310° C. at ~10 psig and a WHSV of 6 $hr^{-1}$. The water drained from the bottom of the reactor contained less than 0.1 M isobutanol, and isobutylene (gas) was collected with >99% conversion. The isobutylene gas was dried by passing it through molecular sieves, and was then fed into a second reactor containing a ZSM-5 catalyst maintained at 140-160° C., ambient pressure, and WHSV=1.5 $hr^{-1}$ to give ~60% conversion to a mixture of about 80% of diisobutylene isomers and about 20% triisobutylene isomers and minor quantities of higher molecular weight products.

Example 19

Preparation of Isododecane from Isobutanol

Isobutanol produced by fermentation (e.g. according to Example 1) was separated from the fermentation broth by distillation. The isobutanol, which contains 16% water, was passed through a chemical reactor containing acidic commercial γ-alumina catalyst heated to 310° C. at ~10 psig and a WHSV of 6 $hr^{-1}$. The water drained from the bottom of the reactor contained less than 0.1 M isobutanol, and isobutylene (gas) was collected with >99% conversion. The isobutylene gas was dried by passing it through molecular sieves, and was then fed into a second reactor containing Amberlyst® 35, maintained at 100-120° C., ambient pressure, and WHSV=2.5 $hr^{-1}$ to give ~90% conversion to a mixture of about 15% of diisobutylene isomers, 75% triisobutylene isomers and 10% tetramers. The liquid product was pumped to a trickle-bed hydrogenation reactor packed with a commercial 0.5% Pd on alumina catalyst and co-fed with 10% excess hydrogen. Hydrogenation of >99% of the olefins occurred at 150° C., 150 psig, and WHSV=3 $hr^{-1}$. The saturated hydrocarbon product was collected with an overall process yield of ~90%.

Example 20

Preparation of Gasoline from Dimers and Trimers of Isobutylene

A mixture of about 80% diisobutylene isomers and about 20% triisobutylene isomers and minor quantities of higher molecular weight products was fed into a hydrogenation reactor containing a 0.5% Pd on alumina catalyst maintained at 150° C. and 150 psi to give a saturated hydrocarbon product, which was distilled at atmospheric pressure to give three fractions containing diisobutylene, triisobutylene and small quantities of higher molecular weight products. The three fractions can be separated and used in aviation gasoline and auto gasoline.

Example 21

Preparation of Methylundecene from Isobutylene 90 g of renewable isobutylene was loaded into a 350 mL batch reactor with 10 g of a ZSM-5 catalyst (Si:Al ratio=80) that had been treated with 2,4,6-trimethyl pyridine. The sealed reactor was heated to 220° C. and allowed to react for approximately 40 hours. 75 mL of product was collected and a sample was analyzed by GC/MS. The composition was approximately 30% $C_{12}$ or larger molecules and the primary compounds were isomers of methylundecene.

Example 22

Preparation of Diesel Fuel from Methylundecene

The unsaturated product from Example 21 was loaded into a 350 mL batch reactor containing 1 g of 5% Pd/C catalyst. The reactor was flushed with nitrogen and pressurized with 200 psig of hydrogen. The reactor was heated to 100° C. and held at this temperature for 1 hour. 70 mL of product was collected and analyzed by GC/MS. The product was found to be fully saturated. 70 mL of this hydrogenated mixture was then distilled to concentrate the $C_{12}$+ fraction (e.g., the fraction containing $C_{12}$ or higher hydrocarbons). Approximately 50 mL of the mixture was distilled off (primarily $C_8$ hydrocarbons), leaving 20 mL of $C_{12}$+ hydrocarbons. The flash point of the final product was measured as 51° C. and the derived cetane number was measured by ASTM D6890-07 as 68. The product was determined to meet the ASTM specifications for #1 diesel fuel.

Example 23

Jet Fuel from Isobutylene

Renewable isobutylene was trimerized using a fixed bed continuous flow system equipped with a tube furnace housing SS 316 reactor (OD 5/16 in×12 in), gas flow meters, an HPLC pump, a back pressure regulator, and a gas-liquid separator. In a typical trimerization procedure, the reactor was loaded with β Zeolite CP 814C (Zeolyst International) and isobutylene was fed at WHSV 1-3 $hr^{-1}$ at a reaction temperature of 140-180° C., at atmospheric pressure. The isobutylene conversion was 85% with a product distribution of about 29% dimer isomers, 58% trimer isomers, and 11% tetramer isomers. The hydrogenation of the resulting oligomer blend was carried out at 150° C. and 150 psi $H_2$ to give a hydrocarbon product which was fractionated to provide a blend of saturated $C_{12}$ (trimers) and $C_{16}$, (tetramers) hydrocarbons that were used as a jet fuel feedstock.

Example 24

Preparation of BTEX from Isobutylene

A fixed bed continuous flow system equipped with a tube furnace housing SS 316 reactor (OD 5/16 in×12 in), gas flow meters, an HPLC pump, back pressure regulator, and a gas-liquid separator was loaded with ZSM-5 CBV 8014 Zeolite catalyst. The catalyst was calcined at 540° C. under $N_2$ for 8 hrs before the reaction was started. Isobutylene (e.g., prepared as described herein) was fed into the reactor at WHSV 1.0 $hr^{-1}$ and the reaction conditions were maintained at 400-550° C. and atmospheric pressure. Aromatic products were formed in about 45% yield and the selectivity for BTEX (e.g., benzene, toluene, ethylbenzene and xylene) was 80%. The aromatic product was separated and used in fuels and other products.

Example 25

Preparation of BTEX and Hydrogen from Diisobutylene

A fixed bed continuous flow reactor was loaded with ZSM-5 CBV 8014 Zeolite catalyst. Prior to initiating the reaction, the catalyst was calcined at 540° C. under $N_2$ for 8 hrs. Isobutylene was fed into the reactor at a WHSV of 1.6 $h^{-1}$ while the reaction conditions were maintained at 400-550° C. and atmospheric pressure. Aromatic products were formed in about 38% yield and with a selectivity for BTEX of 80%. The aromatic products were isolated and used in fuels and other products. Hydrogen also was produced as a byproduct of the reaction; about 3 moles of hydrogen were produced for each mole of aromatic ring formed.

Example 26

Integrated Oligomers Production from Isobutylene

Isobutanol produced by fermentation (e.g., as described herein) was separated from the fermentation broth by distillation. The isobutanol, which contains 16% water, was passed through a chemical reactor containing pelleted SPA catalyst heated to 350° C. at 1 atmosphere. Water was drained from the bottom of the reactor and isobutylene was collected with 99% conversion. The isobutylene gas was dried by passing it through molecular sieves, and was then fed into a second reactor containing Amberlyst® 35 (Rohm and Haas) catalyst maintained at 120-140° C. and ambient pressure to give 90% conversion to a mixture of about 27% of diisobutylene isomers and about 70% triisobutylene isomers, and minor quantities of higher molecular weight products.

Example 27

Integrated Saturated Oligomers Production from Isobutylene

Isobutanol produced by fermentation (e.g., as described herein) was separated from the fermentation broth by distillation. The isobutanol, which contains 16% water, was passed through a chemical reactor containing pelleted SPA catalyst heated to 350° C. at 1 atmosphere. Water was drained from the bottom of the reactor and isobutylene was collected with 99% conversion. The isobutylene gas was dried by passing it through molecular sieves, and then fed into a second reactor containing Amberlyst® 35 (Rohm and Haas) catalyst maintained at 120-140° C. and ambient pressure to give 90% conversion to a mixture of about 27% of diisobutylene isomers and about 70% triisobutylene isomers and minor quantities of higher molecular weight products. This oligomers blend was then fed into a third reactor to hydrogenate the olefins over 0.5% Pd supported in alumina at 150° C. and 150 psi $H_2$. The resulting product was fractionated to isolate a blend of isobutylene trimers and tetramers that were used as a jet fuel feedstock.

Example 28

Integrated Production of P-Xylene from Isobutanol

Figure 10:
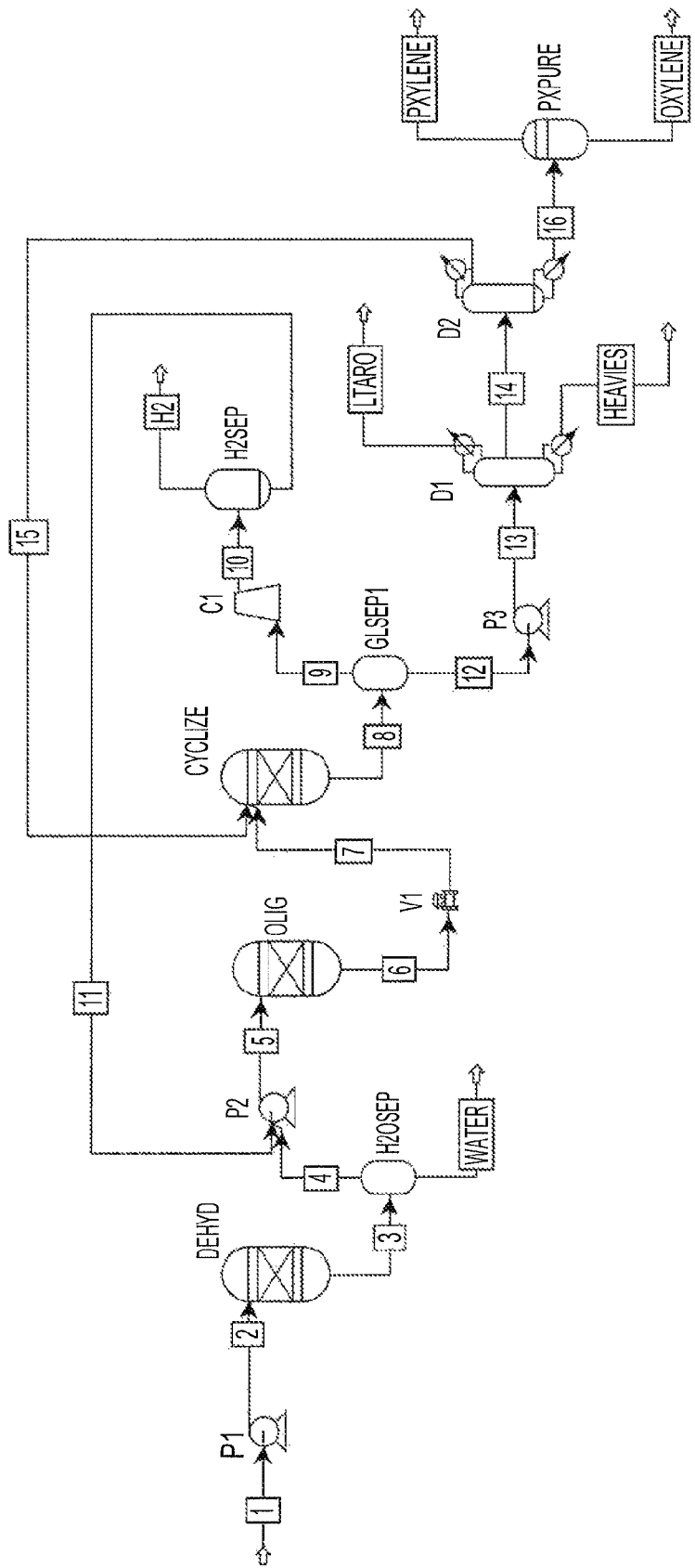
FIG. 10 is a schematic of an integrated process for converting renewable isobutanol to renewable p-xylene.

Renewable isobutanol is converted to renewable p-xylene using a process illustrated in FIG. 10. Renewable isobutanol (e.g., as described herein) is fed wet (15 wt % water) through a preheater into a fixed-bed catalyst reactor packed with a commercial y-alumina catalyst (BASF AL-3996) at a WHSV of 10 $hr^{-1}$. The dehydration reactor is maintained at 290° C. at a pressure of 60 psig. The effluent (3) from the dehydration reactor is fed to a liquid/liquid separator, where water is removed. Analysis of the organic phase (4) shows that it is 95% isobutylene, 3% linear butenes, and 2% unreacted isobutanol. The organic phase is combined with a recycle stream (11) containing isobutane, isooctane, and unreacted butenes and fed to a positive displacement pump (P2) where it is pumped to an oligomerization reactor packed with HZSM-5 catalyst (CBV 2314) at a WHSV of 100 $hr^{-1}$. The reactor is maintained at 170° C. at a pressure of 750 psig. The effluent (6) from the oligomerization reactor is analyzed and shown to contain 60% unreacted feed (isobutane, isooctane, and butenes), 39% isooctene, and 1% trimers. The effluent from the oligomerization reactor is combined with recycled isooctene (15) and fed through a preheater and to a fixed bed reactor containing a commercial chromium oxide doped alumina catalyst (BASF D-1145E ⅛") at a WHSV of 1 $hr^{-1}$. The dehydrocyclization reactor is maintained at 550° C. and 5 psia. The yield of xylenes from the reactor relative to $C_8$ alkenes in the feed is 42% with a selectivity to p-xylene of 90%. The effluent (8) is separated with a gas-liquid separator. The gas-phase is compressed (C1) to 60 psig causing the isobutane and butenes to condense. A second gas-liquid separator is used to recover the hydrogen (and small quantities of methane or other light hydrocarbons). The $C_4$ liquids are recycled (11) and combined with the organic phase from the dehydration reactor (4). The liquid product (12) from the dehydrocyclization reactor is fed to a series of distillation columns slightly above atmospheric pressure by a pump (P3). Any by-product light aromatics (benzene and toluene) and heavy compounds ($C_{9+}$ aromatics or isoolefins) are removed. A side stream (14) rich in xylenes and iso-$C_8$ compounds are fed to a second distillation column. The C8 compounds (isooctene and isooctane) are recycled (15) to the feed of the dehydrocyclization reactor. The xylene fraction (16) is fed to a purification process resulting in a 99.99% pure p-xylene product and a small byproduct stream rich in o-xylene.

The embodiments described herein and illustrated by the foregoing examples should be understood to be illustrative of the present invention, and should not be construed as limiting. On the contrary, the present disclosure embraces alternatives and equivalents thereof, as embodied by the appended claims.

We claim:
1. An integrated process for preparing renewable hydrocarbons, comprising:
  (a) providing renewable isobutanol and renewable ethanol;
  (b) dehydrating the renewable isobutanol, thereby forming a renewable butene mixture comprising one or more renewable linear butenes and renewable isobutene;
  (c) dehydrating the renewable ethanol, thereby forming renewable ethylene;
  (d) reacting at least a portion of the renewable butene mixture and at least a portion of the renewable ethylene to form one or more renewable $C_3$-$C_{16}$ olefins;
  (e) forming renewable hydrogen by one or more of:
    (e1) isolating and dehydrogenating at least a portion of the linear butenes formed in step (b) and/or one or more renewable $C_4$-$C_{16}$ olefins formed in step (d) thereby forming one or more renewable $C_4$-$C_{16}$ dienes and renewable hydrogen;
    (e2) isolating and dehydrocyclizing at least a portion of one or more renewable $C_6$-$C_{16}$ olefins formed in step (d), thereby forming one or more renewable $C_6$-$C_{16}$ aromatics and renewable hydrogen;
    (e3) isolating and dehydrocyclizing at least a portion of one or more renewable $C_6$-$C_{16}$ dienes formed in step (e1) to form one or more renewable $C_6$-$C_{16}$ aromatics and renewable hydrogen; and
  (f) hydrogenating at least a portion of the renewable $C_3$-$C_{16}$ olefins with the renewable hydrogen formed in step (e), thereby forming a renewable saturated hydrocarbon fuel or fuel additive, wherein the amount of said dehydrogenating and/or dehydrocyclizing in step (e), and/or the amount of hydrogenating in step (f) are controlled so that the amount of renewable hydrogen formed in step (e) is essentially completely consumed in step (f).

2. The integrated process of claim 1, wherein the one or more renewable linear butenes comprise 2-butene.

3. The integrated process of claim 1, wherein said reacting of step (d) comprises one or more reactions selected from the group consisting of disproportionation, metathesis, oligomerization, isomerization, alkylation, dehydrodimerization, dehydrocyclization, and combinations thereof.

4. The integrated process of claim 1, wherein said reacting of step (d) comprises dimerizing at least a portion of the renewable isobutene, thereby forming a renewable isobutene dimer mixture comprising at least one $C_8$ hydrocarbon selected from the group consisting of a 2,4,4-trimethylpentene, a 2,5-dimethylhexene, and 2,5-dimethylhexadienes, and combinations thereof.

5. The integrated process of claim 1, wherein said reacting of step (d) comprises trimerizing at least a portion of the renewable isobutene, thereby forming a renewable isobutene trimer mixture comprising 2,2,4,6,6-pentamethylheptane.

6. The integrated process of claim 1, wherein said reacting of step (d) comprises tetramerizing at least a portion of the renewable isobutene, thereby forming a renewable isobutene tetramer mixture, wherein the renewable isobutene tetramer mixture comprises 2,2,4,6,6,8,8-heptamethylnonene.

7. The integrated process of claim 1, wherein said reacting of step (d) comprises isomerizing at least a portion of the renewable isobutene of step (b) to form an isobutene isomerization mixture comprising renewable 2-butene, wherein said reacting of step (d) further comprises disproportionating at least a portion of the renewable ethylene formed in step (c) and at least a portion of the renewable 2-butene formed by isomerizing at least a portion of the renewable isobutene of step (b), thereby forming renewable propylene.

8. The integrated process of claim 2, wherein said reacting of step (d) comprises disproportionating at least a portion of the renewable ethylene formed in step (c) and at least a portion of the renewable 2-butene formed in step (b), thereby forming renewable propylene.

9. The integrated process of claim 2, wherein said reacting of step (d) comprises disproportionating at least a portion of the renewable ethylene formed in step (c), and at least a portion of the renewable 2-butene formed in step (b) and renewable 2-butene formed by isomerizing the renewable isobutene formed in step (b), thereby forming renewable propylene.

10. The integrated process of claim 1, wherein step (e) comprises step (e1).

11. The integrated process of claim 10, wherein the one or more renewable $C_4$-$C_{16}$ dienes formed in step (e1) comprise butadiene.

12. The integrated process of claim 1, wherein step (e) comprises step (e2).

13. The integrated process of claim 12, wherein the one or more renewable $C_6$-$C_{16}$ aromatics formed in step (e2) comprise renewable p-xylene.

14. The integrated process of claim 1, wherein step (e) comprises step (e1) and step (e2).

15. The integrated process of claim 1, wherein step (e) comprises step (e1) and step (e3).

16. The integrated process of claim 1, wherein step (e) comprises step (e1), step (e2), and step (e3).

17. The integrated process of claim 4, wherein at least a portion of the renewable isobutene dimer mixture is hydrogenated in step (f), whereby the renewable saturated hydrocarbon fuel or fuel additive comprises isooctane, wherein the renewable isobutene dimer mixture is hydrogenated in step (f), whereby the renewable saturated hydrocarbon fuel or fuel additive comprises isooctane.

18. The integrated process of claim 5, wherein at least a portion of the renewable isobutene trimer mixture is hydrogenated in step (f), whereby the renewable saturated hydrocarbon fuel or fuel additive comprises one or more pentamethylheptanes, wherein the renewable isobutene trimer mixture is hydrogenated in step (f), whereby the renewable saturated hydrocarbon fuel or fuel additive comprises one or more pentamethylheptanes.

19. The integrated process of claim 1, wherein said reacting of step (d) further comprises mixing said renewable butene mixture and/or said renewable ethylene with at least a portion of a non-renewable butene and/or a butene mixture and/or non-renewable renewable ethylene to form one or more $C_3$-$C_{16}$ olefins, and at least a portion of said one or more $C_3$-$C_{16}$ olefins are renewable.

* * * * *